United States Patent
Cho et al.

(10) Patent No.: US 10,355,214 B2
(45) Date of Patent: Jul. 16, 2019

(54) COPOLYMER AND ORGANIC SOLAR CELL COMPRISING SAME

(71) Applicants: LG CHEM, LTD., Seoul (KR); DAEGU GYEONGBUK INSTITUTE OF SCIENCE AND TECHNOLOGY, Daegu (KR)

(72) Inventors: Keun Cho, Daejeon (KR); Youngu Lee, Daegu (KR); Jaechol Lee, Daejeon (KR); Jinseck Kim, Daejeon (KR); Songrim Jang, Daejeon (KR); Junghyun Park, Daejeon (KR); Honggi Kim, Daegu (KR)

(73) Assignees: LG Chem, Ltd. (KR); Daegu Gyeongbuk Institute of Science and Technology (KR)

( * ) Notice: Subject to any disclaimer, the term of this patent is extended or adjusted under 35 U.S.C. 154(b) by 229 days.

(21) Appl. No.: 15/125,961

(22) PCT Filed: Mar. 27, 2015

(86) PCT No.: PCT/KR2015/003059
§ 371 (c)(1),
(2) Date: Sep. 13, 2016

(87) PCT Pub. No.: WO2015/147598
PCT Pub. Date: Oct. 1, 2015

(65) Prior Publication Data
US 2018/0166633 A1 Jun. 14, 2018

(30) Foreign Application Priority Data
Mar. 27, 2014 (KR) .................. 10-2014-0035801

(51) Int. Cl.
*C08L 65/00* (2006.01)
*C08K 3/04* (2006.01)
(Continued)

(52) U.S. Cl.
CPC ........ *H01L 51/0043* (2013.01); *C07D 495/04* (2013.01); *C07D 519/00* (2013.01);
(Continued)

(58) Field of Classification Search
CPC ............. H01L 51/0043; H01L 51/0035; H01L 51/0036; H01L 51/4253; H01L 51/424;
(Continued)

(56) References Cited

U.S. PATENT DOCUMENTS

2006/0223977 A1 10/2006 Zahn et al.
2012/0298193 A1 11/2012 Ihn et al.

FOREIGN PATENT DOCUMENTS

JP 2010-202554 A 9/2010
JP 2012241197 12/2012
(Continued)

OTHER PUBLICATIONS

Uakron "http://gozips.uakron.edu/~wwschlo/POLYFiles/POLY102.pdf" (Year: 2018).*
(Continued)

*Primary Examiner* — Jeffrey T Barton
*Assistant Examiner* — Michael Y Sun
(74) *Attorney, Agent, or Firm* — Myers Bigel, P.A.

(57) ABSTRACT

The present specification relates to a copolymer and an organic solar cell comprising the same.

16 Claims, 28 Drawing Sheets

(51) Int. Cl.

| | |
|---|---|
| *C08G 61/12* | (2006.01) |
| *C08L 41/00* | (2006.01) |
| *H01L 51/00* | (2006.01) |
| *H01L 51/42* | (2006.01) |
| *C07D 495/04* | (2006.01) |
| *C07D 519/00* | (2006.01) |
| *G01R 33/46* | (2006.01) |

(52) U.S. Cl.
CPC ......... *C08G 61/123* (2013.01); *C08G 61/126* (2013.01); *C08K 3/045* (2017.05); *C08L 41/00* (2013.01); *C08L 65/00* (2013.01); *H01L 51/0035* (2013.01); *H01L 51/0036* (2013.01); *H01L 51/424* (2013.01); *H01L 51/4253* (2013.01); *C08G 2261/12* (2013.01); *C08G 2261/149* (2013.01); *C08G 2261/1412* (2013.01); *C08G 2261/1424* (2013.01); *C08G 2261/1426* (2013.01); *C08G 2261/212* (2013.01); *C08G 2261/3243* (2013.01); *C08G 2261/334* (2013.01); *C08G 2261/344* (2013.01); *C08G 2261/364* (2013.01); *C08G 2261/91* (2013.01); *C08L 2203/204* (2013.01); *G01R 33/46* (2013.01); *Y02E 10/549* (2013.01)

(58) Field of Classification Search
CPC .... C08L 41/00; C08L 65/00; C08L 2203/204; C08K 3/045; C07D 495/04; C07D 519/00; G01R 33/46; Y02E 10/549; C08G 61/126; C08G 61/123; C08G 2261/212; C08G 2261/91; C08G 2261/364; C08G 2261/344; C08G 2261/334; C08G 2261/12; C08G 2261/149; C08G 2261/1426; C08G 2261/1424; C08G 2261/1412; C08G 2261/3243

See application file for complete search history.

(56) References Cited

FOREIGN PATENT DOCUMENTS

| | | | |
|---|---|---|---|
| JP | 2013-168450 A | 8/2013 | |
| JP | 2013168450 * | 8/2013 | ......... Y02E 105/549 |
| WO | 2014042091 | 3/2014 | |
| WO | WO-2014042091 A1 * | 3/2014 | ........... C08G 61/126 |

OTHER PUBLICATIONS

Liang, et al.: "Regioregular Oligomer and Polymer Containing Thieno[3,4-b]thiophene Moiety for Efficient Organic Solar Cells", Macromolecules, vol. 42, No. 4, Feb. 24, 2009, pp. 1091-1098.

Liao, et al.: "Fullerene Derivative-Doped Zinc Oxide Nanofilm as the Cathode of Inverted Polymer Solar Cells with Low-Bandgap Polymer (PTB7-Th) for High Performance", Advanced Materials, vol. 25, No. 34, Sep. 14, 2013, pp. 4766-4771.

Ye, et al.: "Highly Efficient 2D-Conjugated Benzodithiophene-Based Photovoltaic Polymer with Linear Alkylthio Side Chain", Chemistry of Materials, vol. 26, No. 12, Jun. 24, 2014, pp. 3603-3605.

Kim, et al.: "Regioregular Low Bandgap Polymer with Controlled Thieno[3,4-b]thiophene Orientation for High-Efficiency Polymer Solar Cells", Chemistry of Materials, vol. 27, No. 8, Apr. 28, 2015, pp. 3102-3107.

Zhong, et al.: "Influence of Regio- and Chemoselectivity on the Properties of Fluoro-Substituted Thienothiophene and Benzodithiophene Copolymers", Journal of the American Chemical Society, vol. 137, No. 24, Jun. 24, 2015, pp. 7616-7619.

* cited by examiner

[FIG. 1]
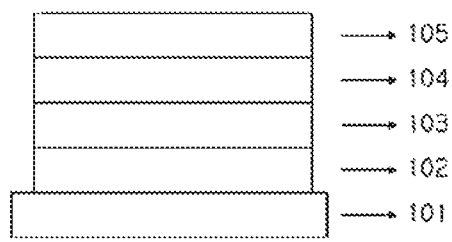
[FIG. 2]
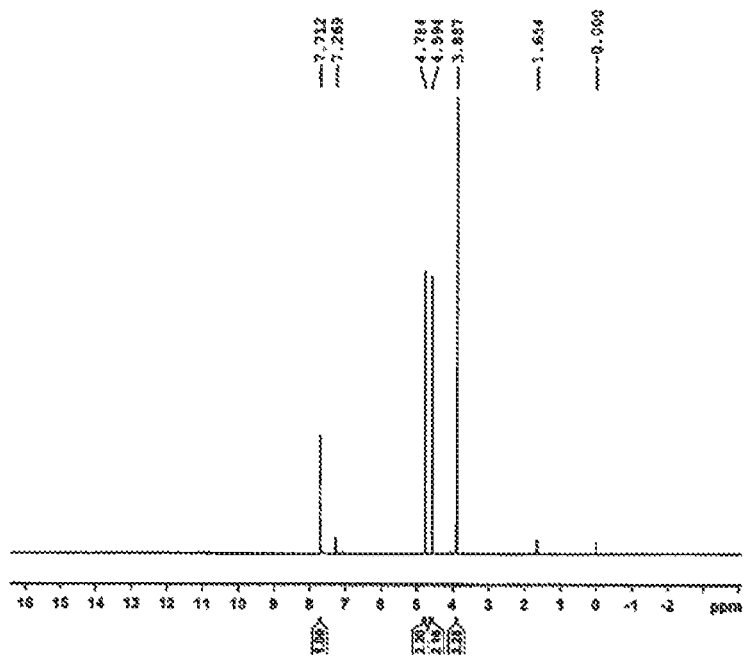

[FIG. 3]
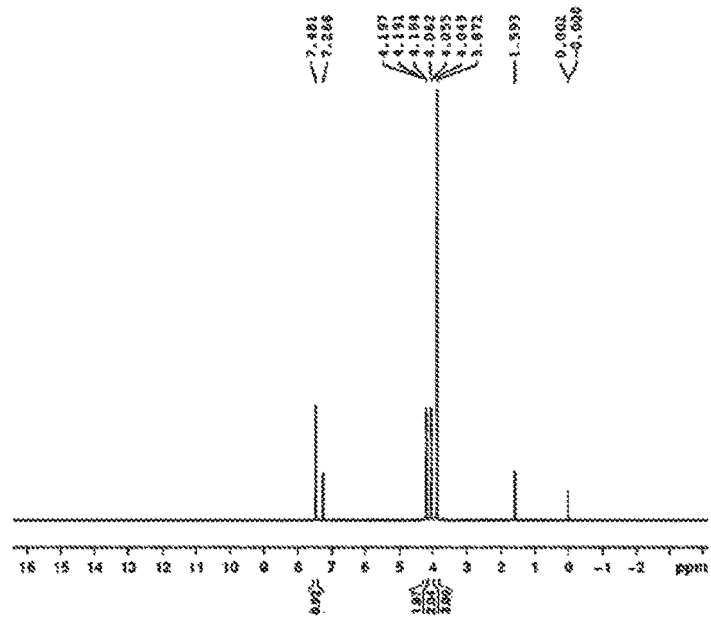
[FIG. 4]
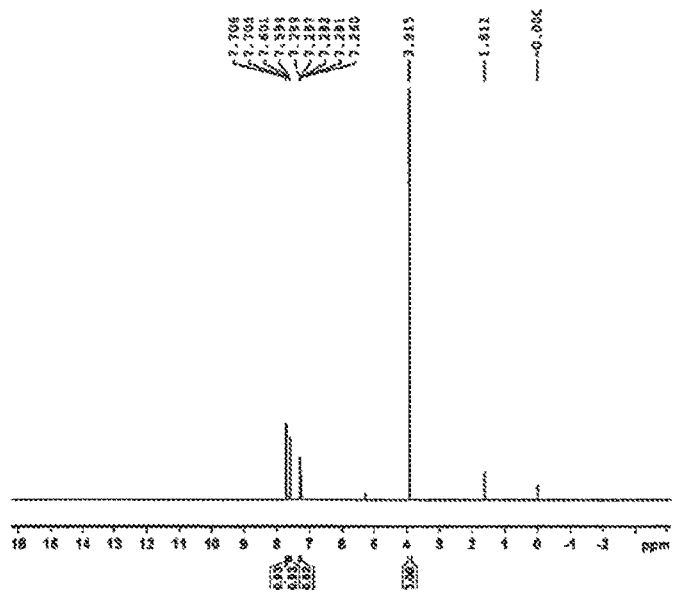

[FIG. 5]
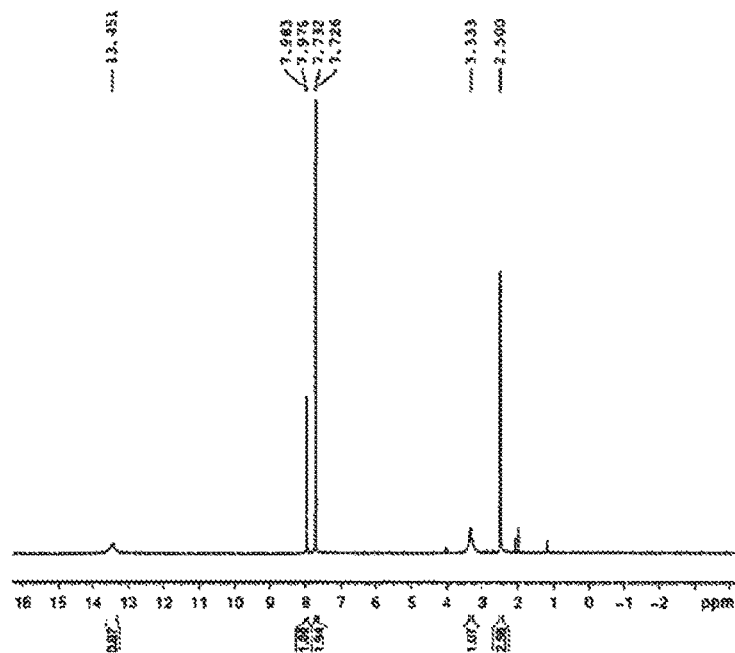
[FIG. 6]
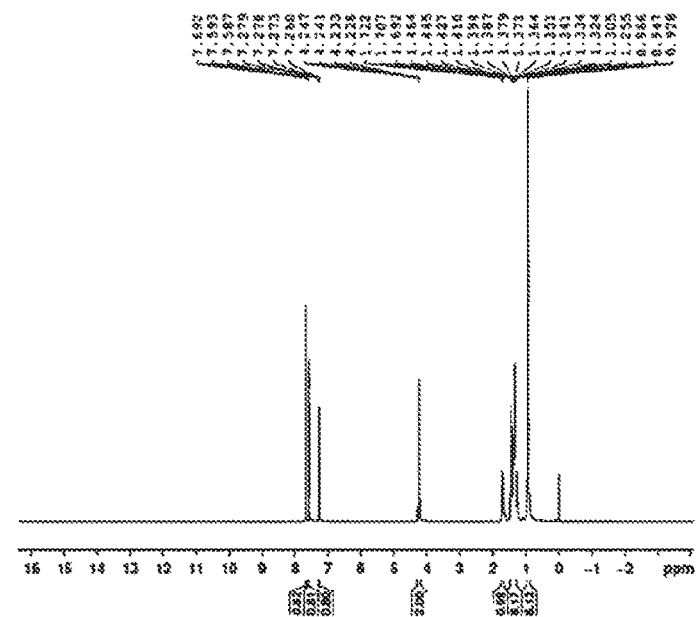

[FIG. 7]
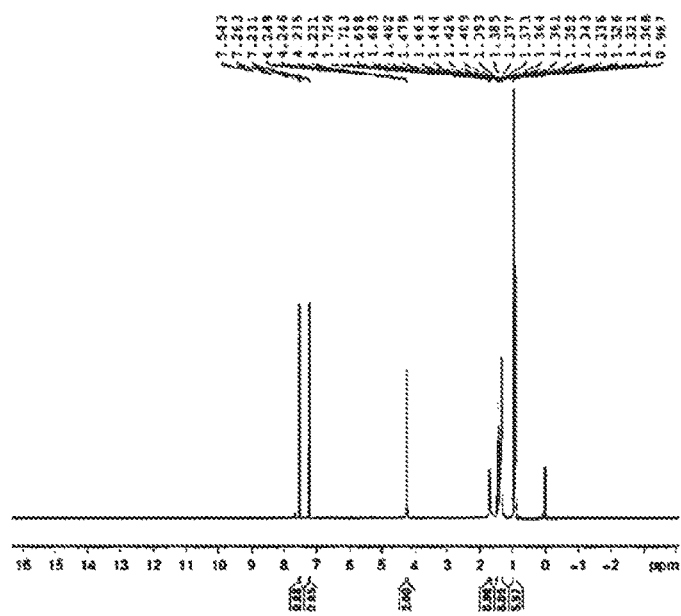
[FIG. 8]
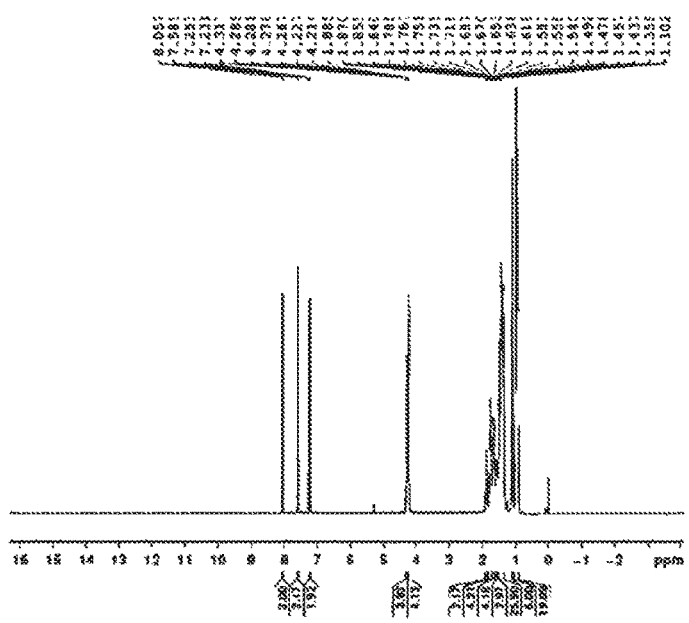

[FIG. 9]
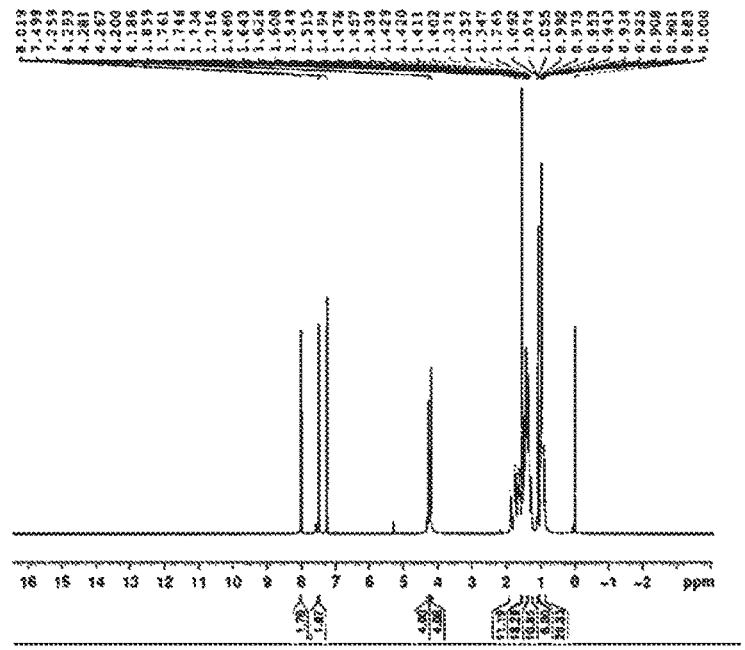
[FIG. 10]
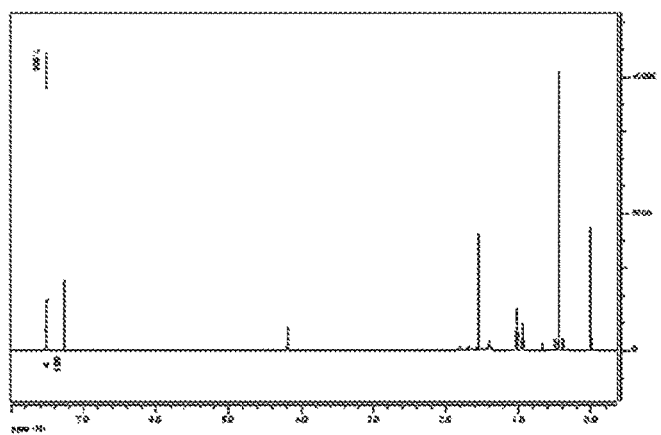

[FIG. 11]
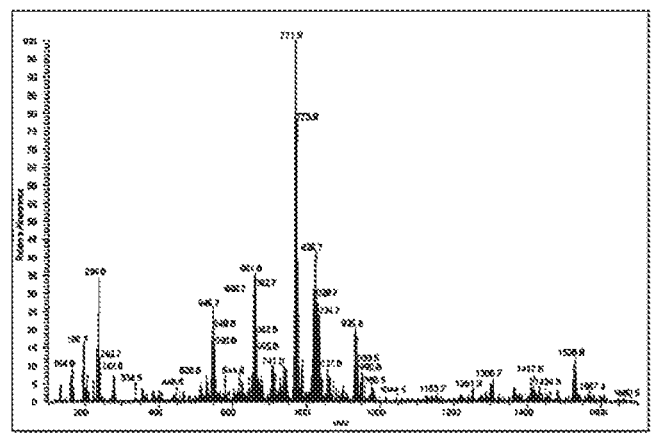
[FIG. 12]
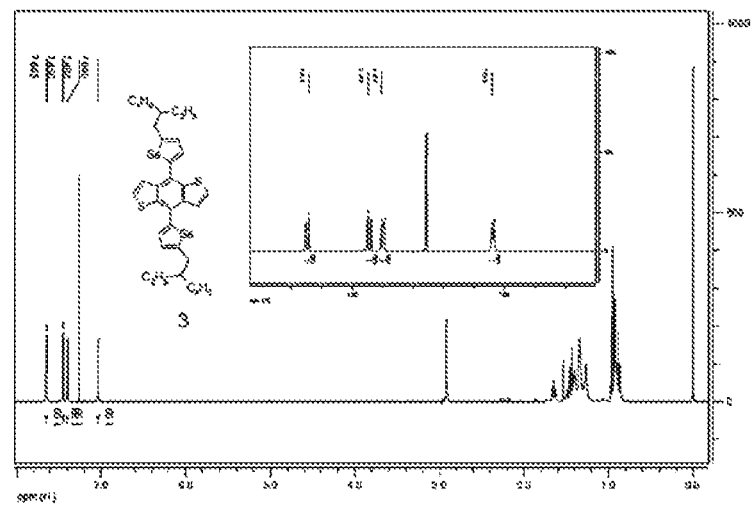

[FIG. 13]
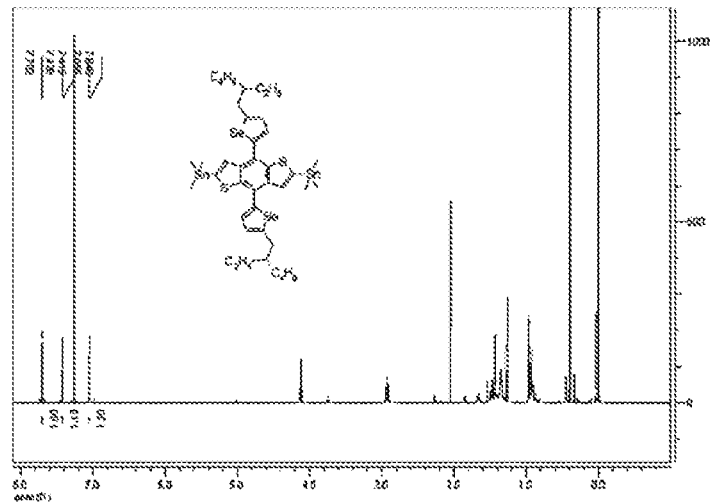
[FIG. 14]
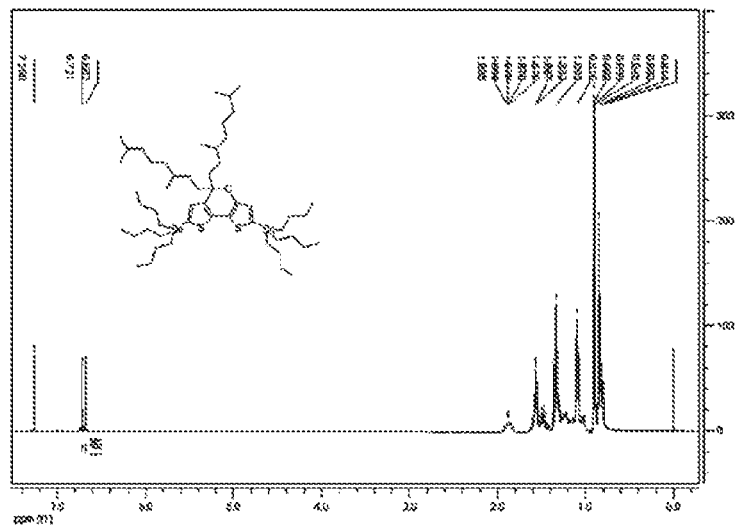

[FIG. 15]
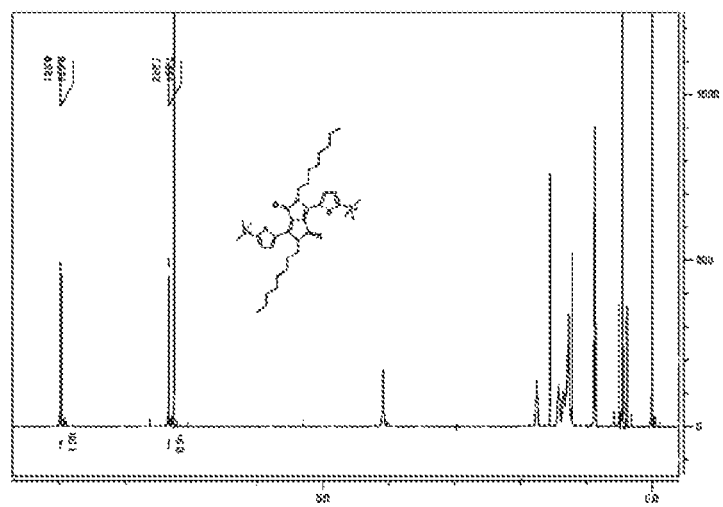
[FIG. 16]
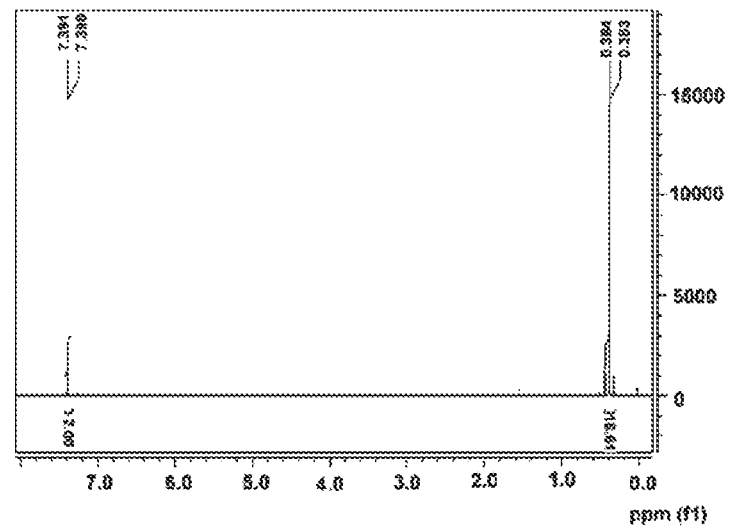

[FIG. 17]
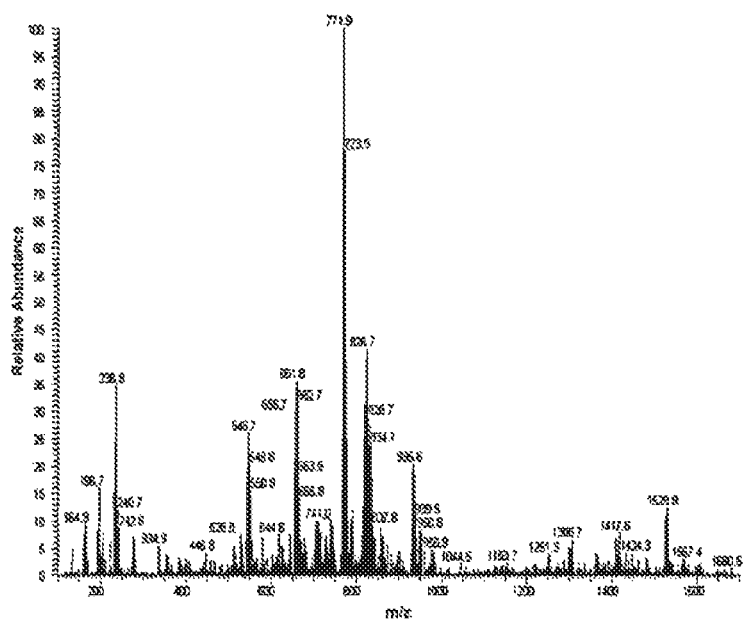
[FIG. 18]

[FIG. 19]
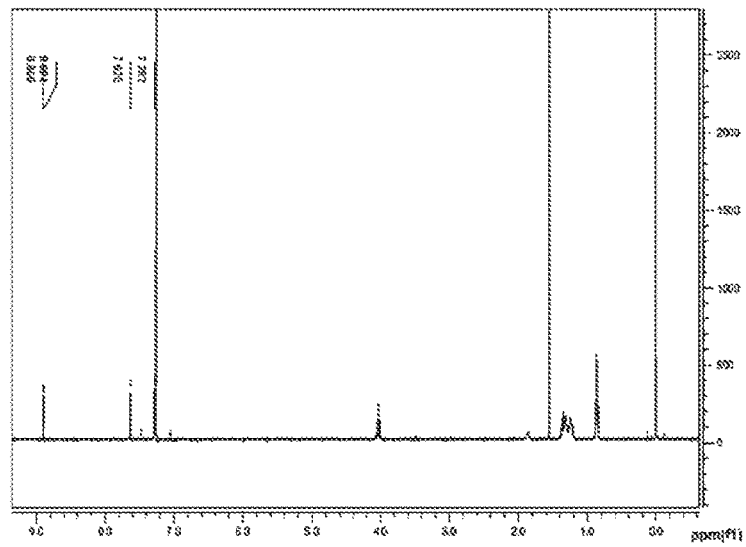
[FIG. 20]
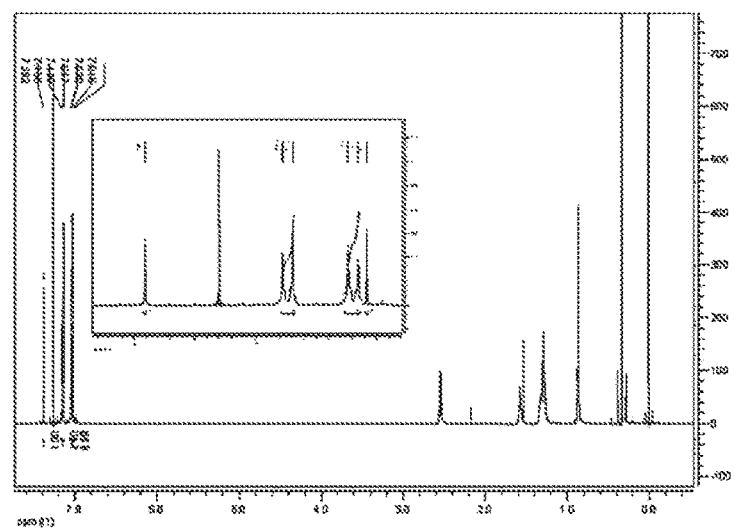

[FIG. 21]
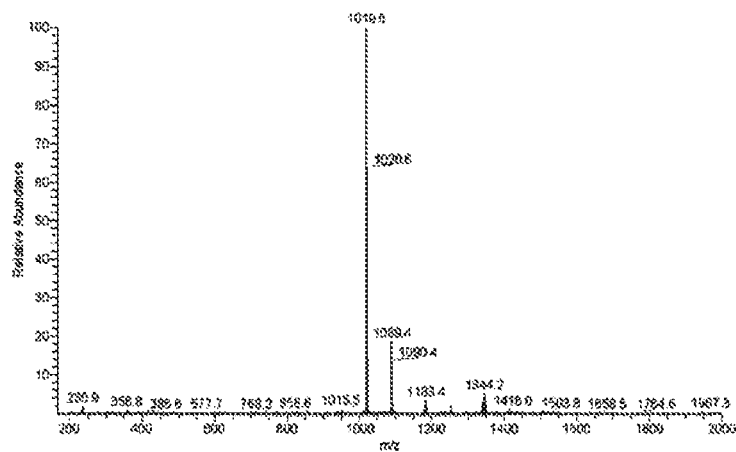
[FIG. 22]
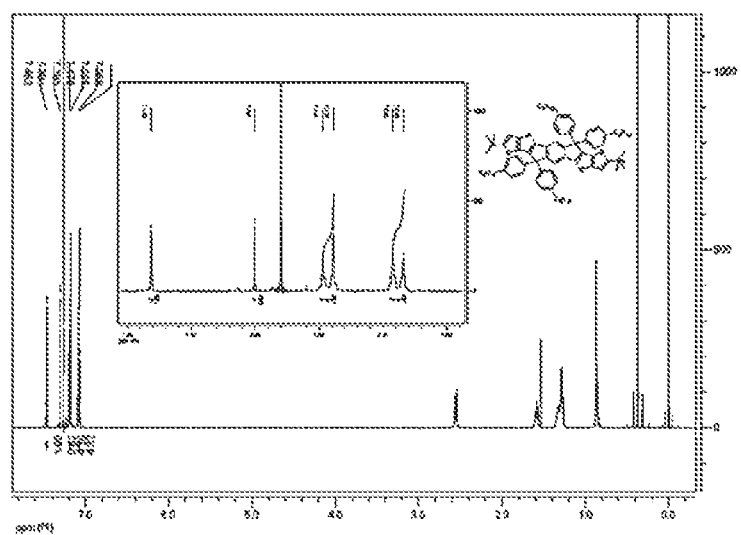

[FIG. 23]
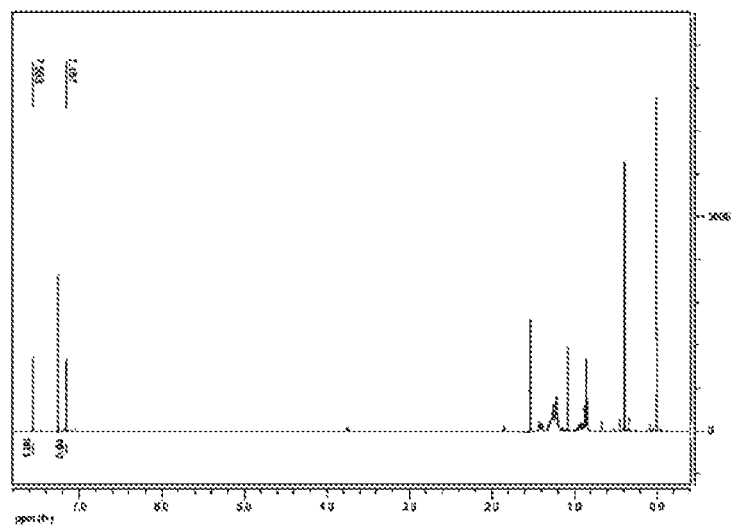
[FIG. 24]
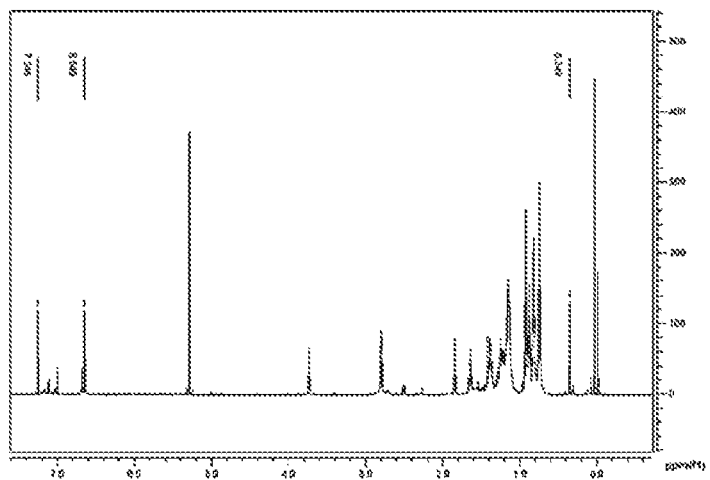

[FIG. 25]
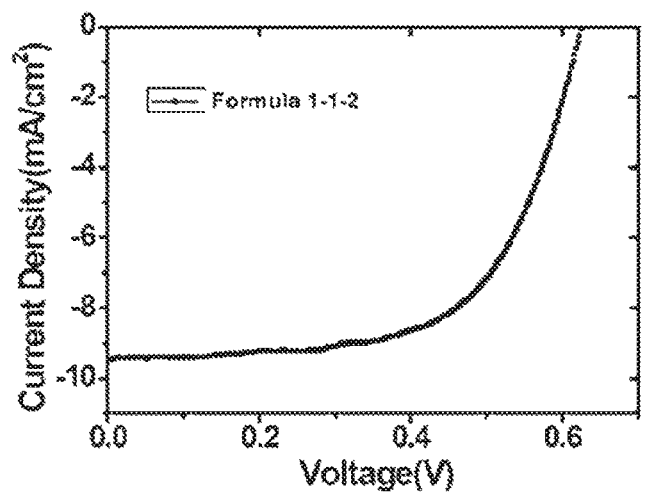
[FIG. 26]
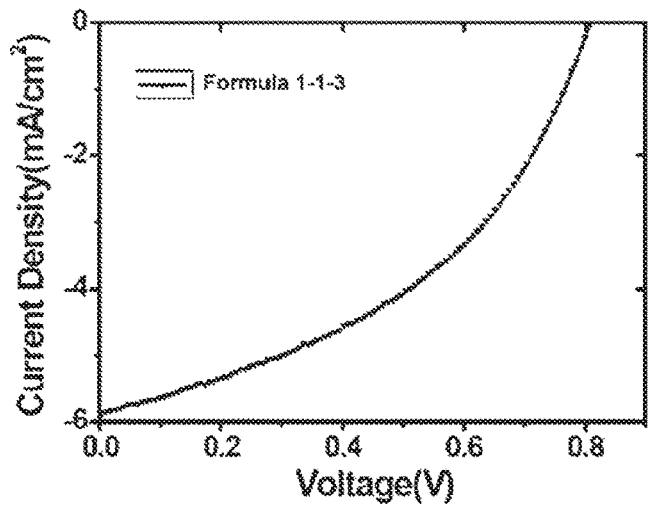

[FIG. 27]
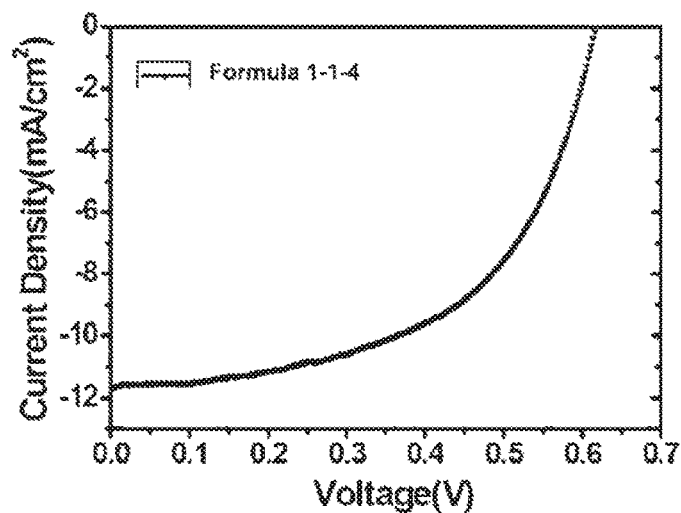
[FIG. 28]
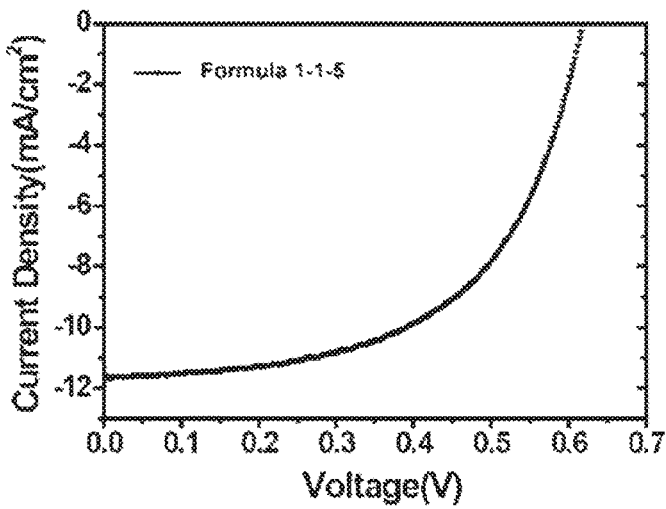

[FIG. 29]
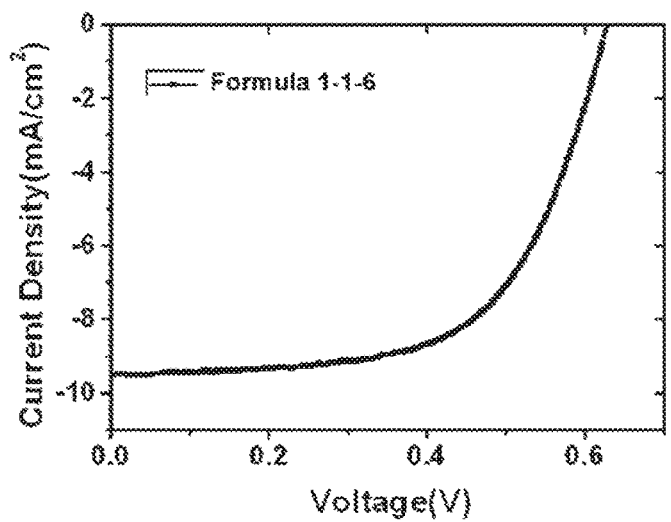
[FIG. 30]
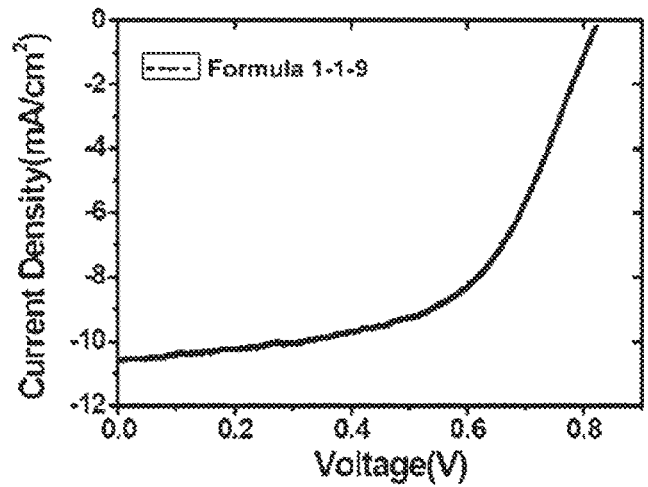

[FIG. 31]
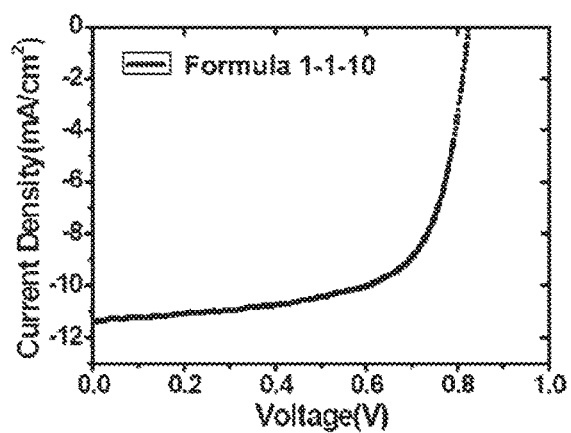
[FIG. 32]
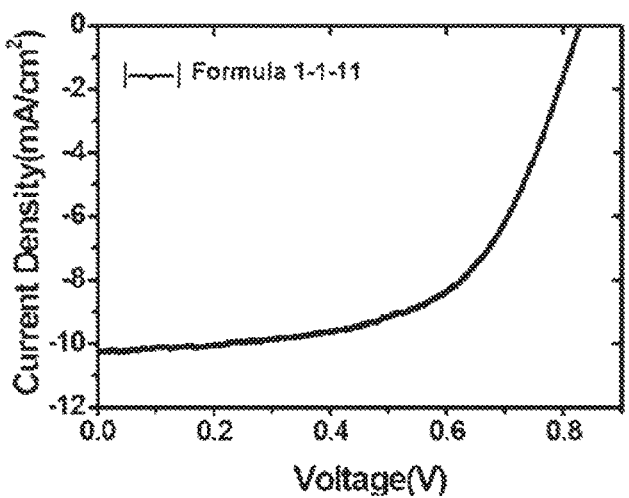

[FIG. 33]
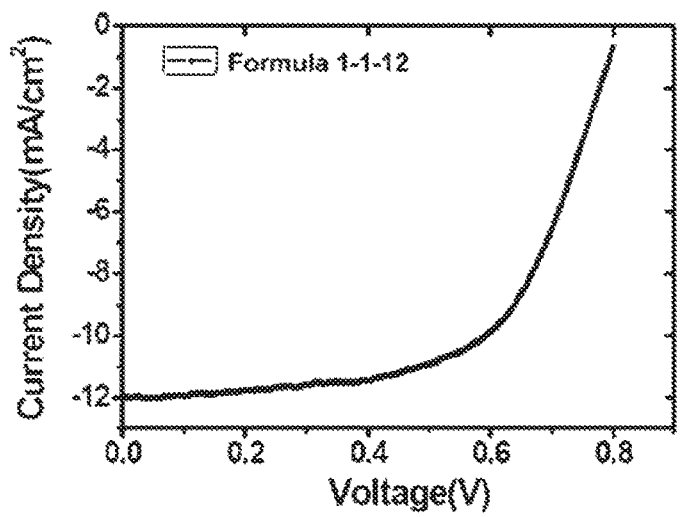
[FIG. 34]
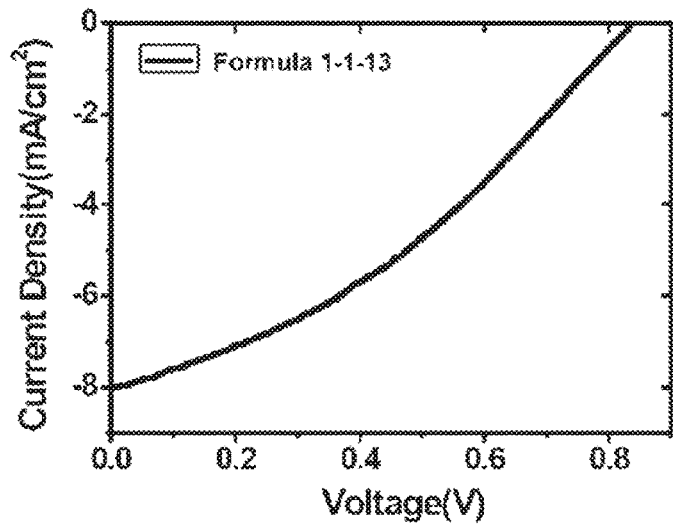

[FIG. 35]
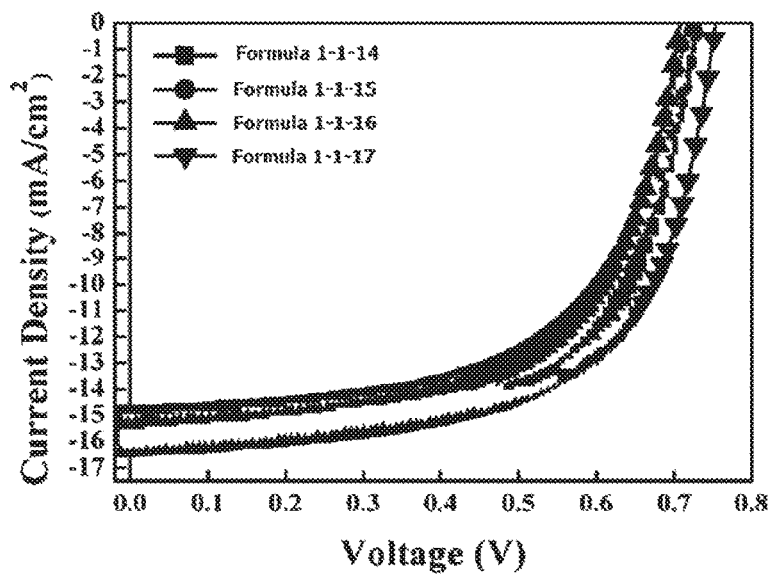
[FIG. 36]
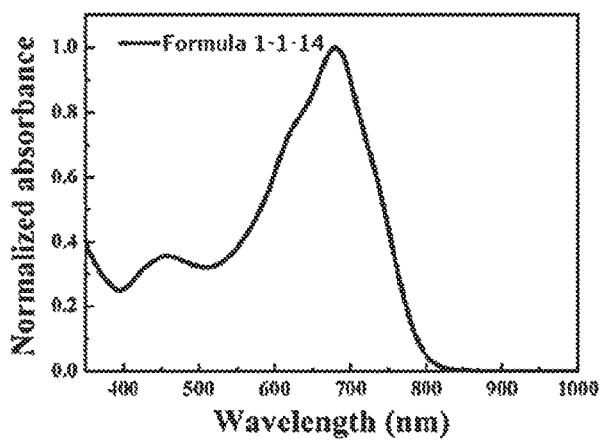

[FIG. 37]
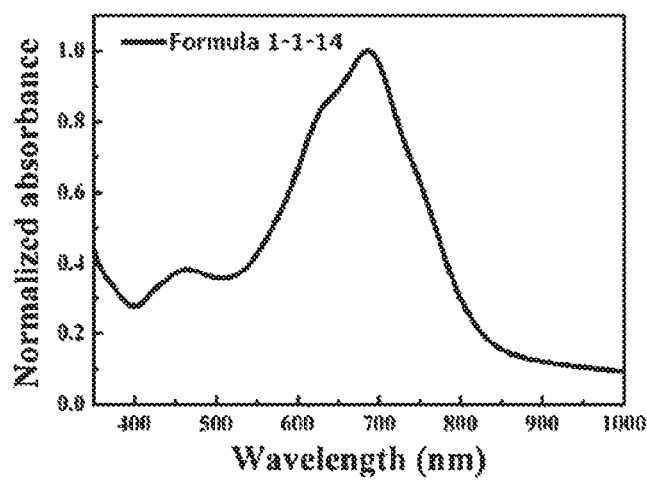
[FIG. 38]
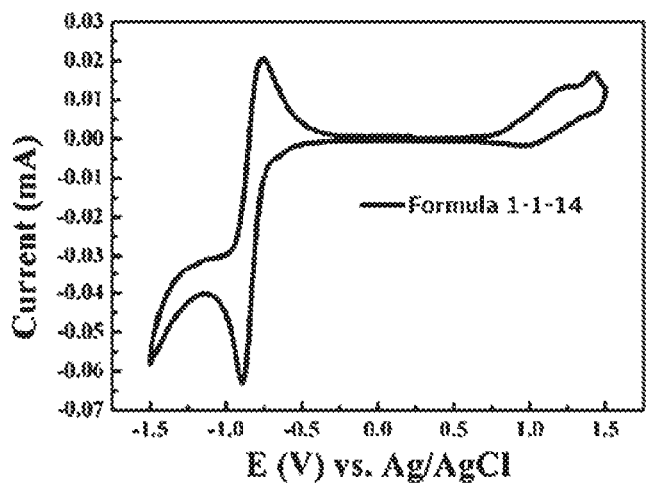

[FIG. 39]
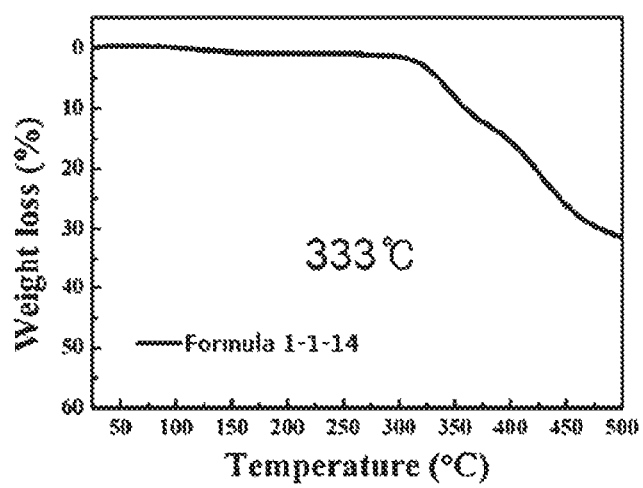
[FIG. 40]
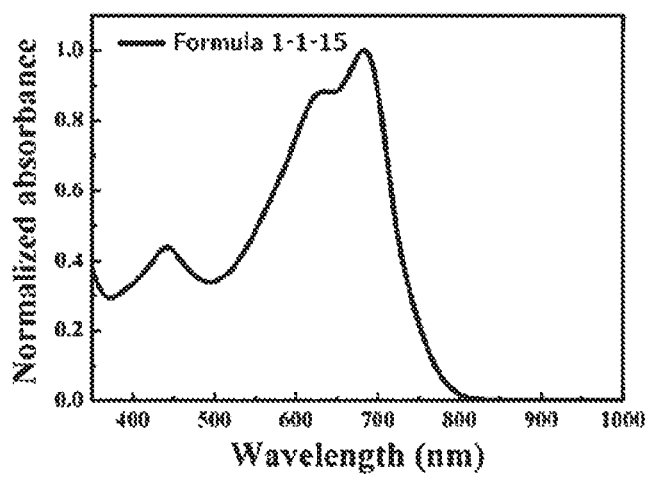

[FIG. 41]
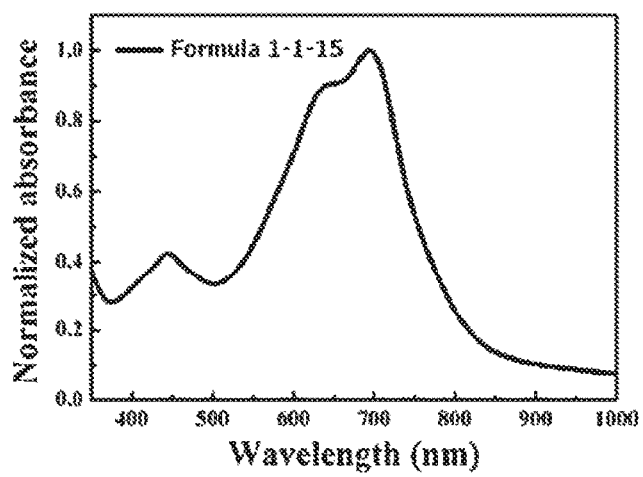
[FIG. 42]
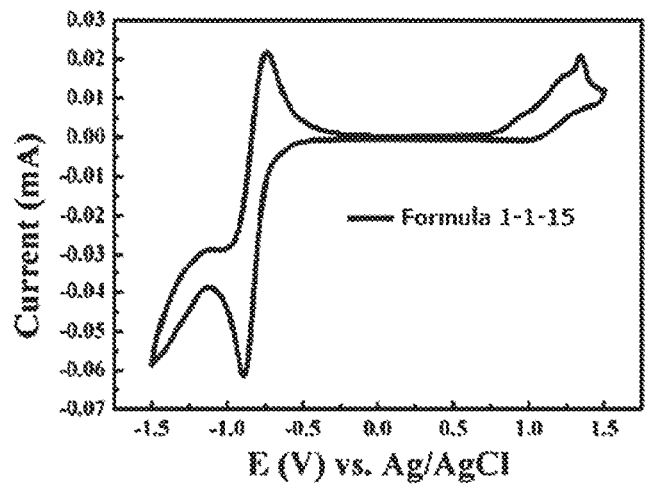

[FIG. 43]
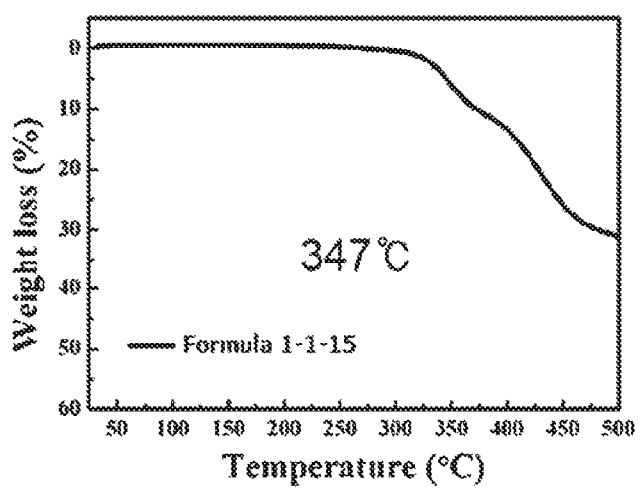
[FIG. 44]
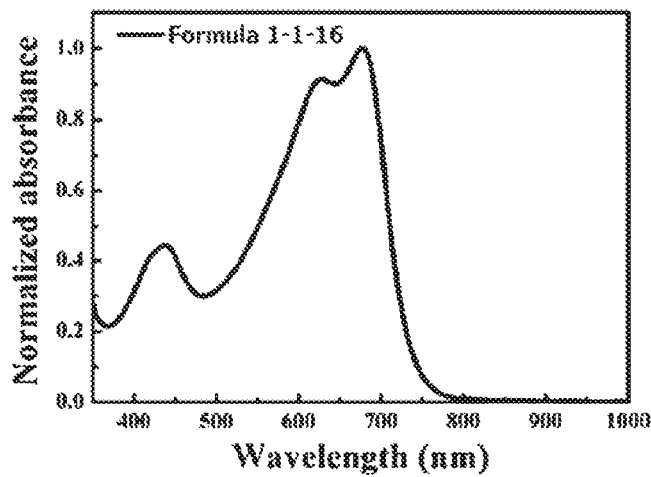

[FIG. 45]
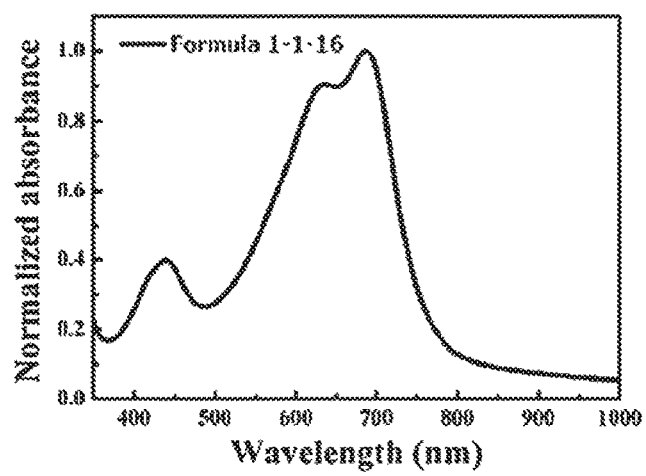
[FIG. 46]
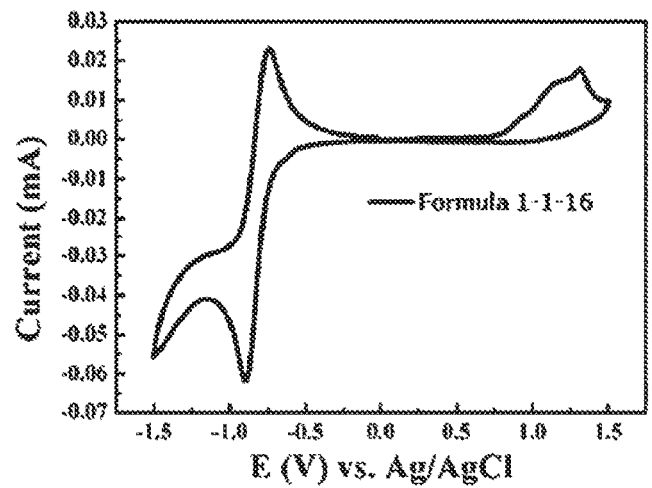

[FIG. 47]
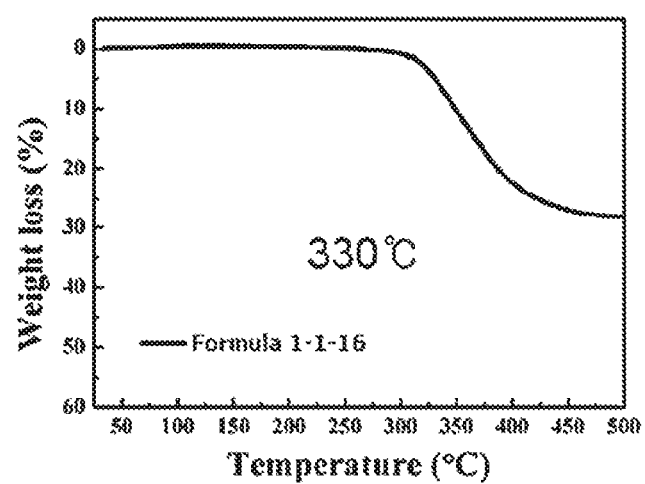
[FIG. 48]
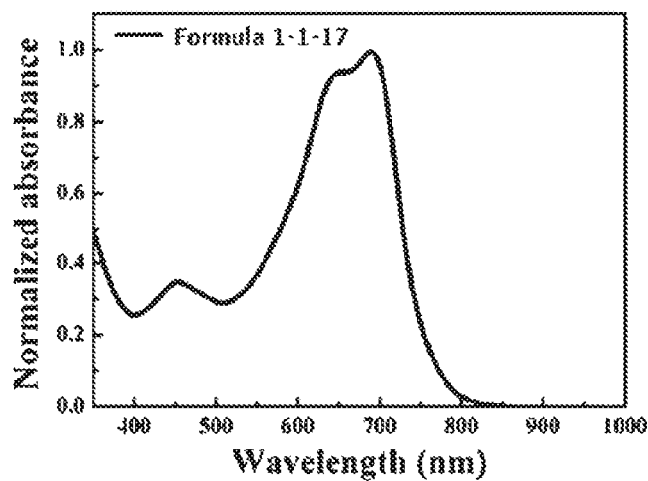

[FIG. 49]
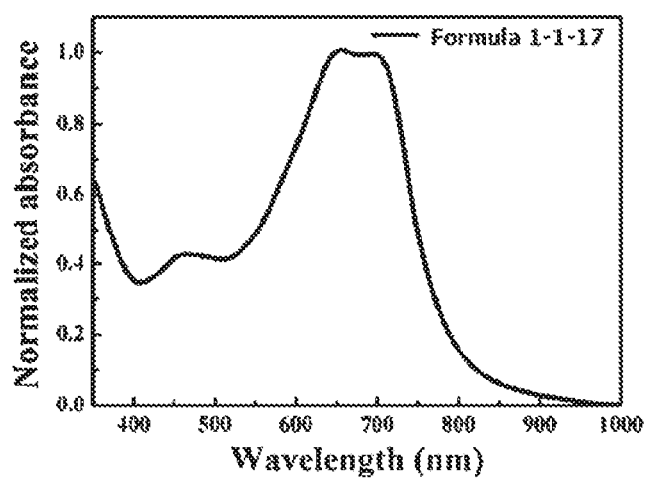
[FIG. 50]
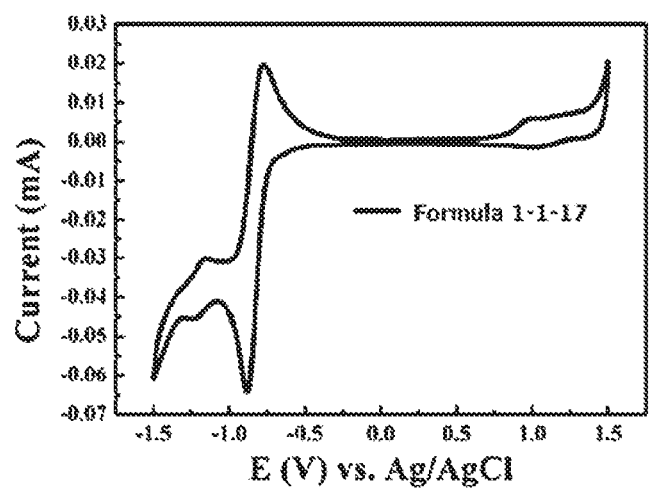

[FIG. 51]
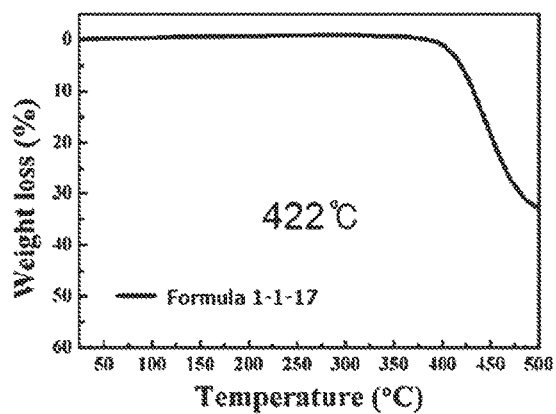
[FIG. 52]
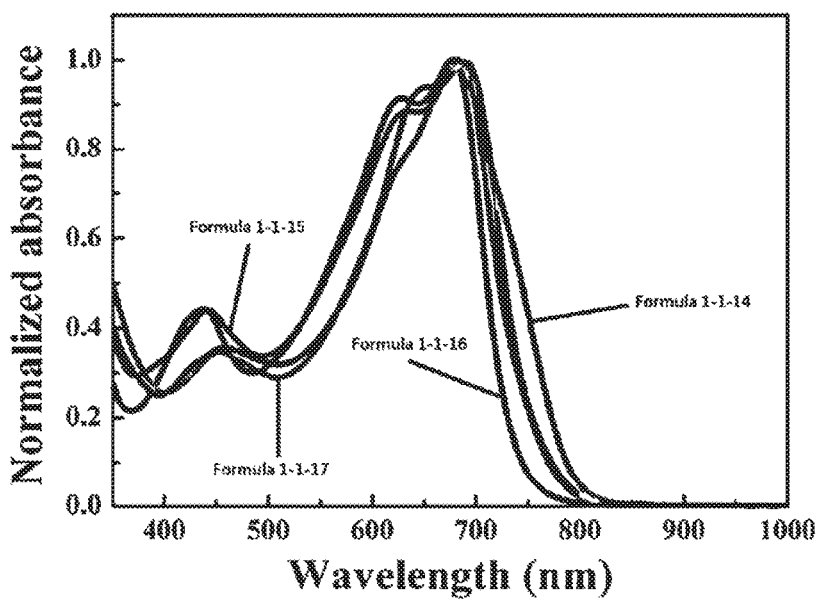

[FIG. 53]
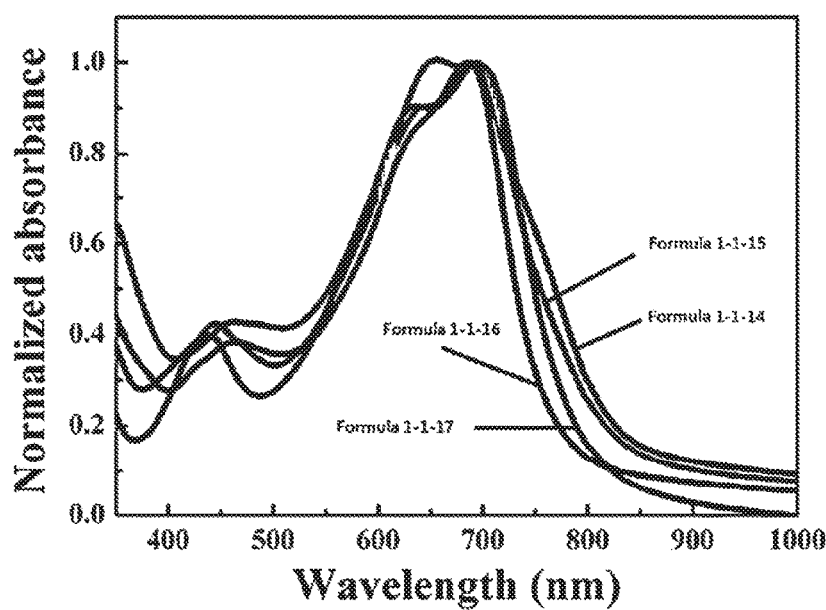

[FIG. 54]
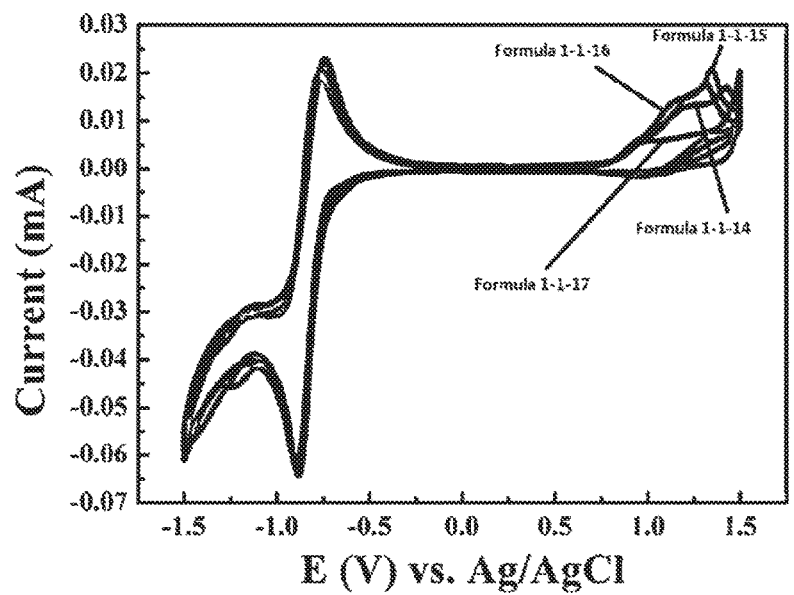
[FIG. 55]
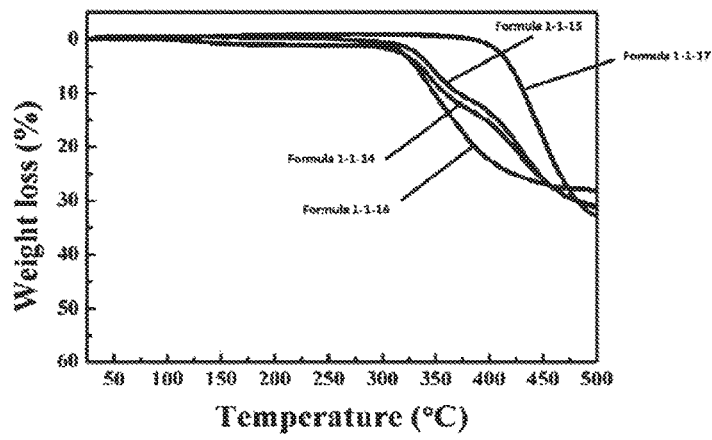

COPOLYMER AND ORGANIC SOLAR CELL COMPRISING SAME

This application is a National Stage Application of International Application No. PCT/KR2015/003059, filed Mar. 27, 2015, and claims the benefit of Korean Patent Application No. 10-2014-0035801, filed Mar. 27, 2014, the contents of which are incorporated herein by reference in their entirety for all purposes as if fully set forth below.

TECHNICAL FIELD

This application claims priority to and the benefits of Korean Patent Application No. 10-2014-0035801, filed with the Korean Intellectual Property Office on Mar. 27, 2014, the entire contents of which are incorporated herein by reference.

The present specification relates to a copolymer and an organic solar cell comprising the same.

BACKGROUND ART

An organic solar cell is a device capable of directly converting solar energy to electric energy by applying a photovoltaic effect. Solar cells are divided into inorganic solar cells and organic solar cells depending on the materials forming a thin film. Typical solar cells are fabricated using a p-n junction by doping crystalline silicon (Si), an inorganic semiconductor. Electrons and holes generated by light absorption spread to p-n junction points, are accelerated by the electric field, and move to an electrode. Power conversion efficiency of this process is defined as a ratio of power given to an external circuit and solar power put into a solar cell, and the ratio has been accomplished up to 24% when measured under a currently standardized hypothetical solar irradiation condition. However, existing inorganic solar cells already has a limit in economic feasibility and material supplies, and therefore, organic material semiconductor solar cells that are readily processed, inexpensive and have various functions have been highly favored as a long-term alternative energy source.

For solar cells, it is important to increase efficiency so as to output as much electric energy as possible from solar energy. In order to improve efficiency of such solar cells, generating as much excitons as possible inside a semiconductor is important, however, taking the generated charges outside without loss is also important. One of the reasons for the charge loss is the dissipation of the generated electrons and holes by recombination. Various methods for delivering the generated electrons or holes without loss have been proposed, however, most of the methods require additional processes, and accordingly, the fabricating costs may increase.

PRIOR ART DOCUMENTS

Patent Documents

U.S. Pat. No. 5,331,183
U.S. Pat. No. 5,454,880

DISCLOSURE

Technical Problem

An object of the present specification is to provide a copolymer and an organic solar cell comprising the same.

Technical Solution

The present specification provides a copolymer including a unit represented by the following Chemical Formula 1.

[Chemical Formula 1]

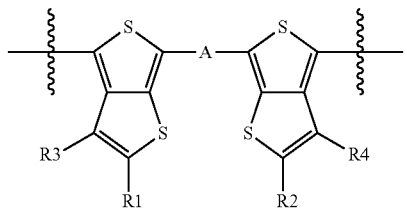

In Chemical Formula 1,

R1 and R2 are the same as or different from each other, and each independently hydrogen; a halogen group; a nitro group; a cyano group; a carboxyl group; a hydroxyl group; a substituted or unsubstituted carbonyl group; carbonyl group; a substituted or unsubstituted alkyl group; a substituted or unsubstituted allyl group; a substituted or unsubstituted alkoxy group; a substituted or unsubstituted cycloalkyl group; a substituted or unsubstituted alkenyl group; a substituted or unsubstituted ester group; a substituted or unsubstituted amide group; a substituted or unsubstituted ether group; a substituted or unsubstituted sulfonyl group; a substituted or unsubstituted sulfoxy group; a substituted or unsubstituted arylalkyl group; a substituted or unsubstituted aryl group; or a substituted or unsubstituted heterocyclic group including one or more of N, O, S and Se atoms, R3 and R4 are the same as or different from each other, and each independently hydrogen; or an electron withdrawing group, and A is a substituted or unsubstituted monocyclic or multicyclic aryl group; or a substituted or unsubstituted monocyclic or multicyclic heterocyclic group including one or more of N, O, S and Se atoms.

In addition, the present specification provides an organic solar cell including a first electrode; a second electrode provided opposite to the first electrode; and one or more organic material layers provided between the first electrode and the second electrode and including a photoactive layer, wherein one or more layers of the organic material layers include the copolymer described above.

Advantageous Effects

A copolymer according to one embodiment of the present specification includes a first unit represented by Chemical Formula 1 and a second unit represented by Chemical Formula 2 of which linking sites are selected, and has regioregularity that the linking sites of the two units in the copolymer are selected. The copolymer having regioregularity according to one embodiment of the present specification has relatively excellent crystallinity.

The copolymer according to one embodiment of the present specification includes a structure in which two thiophene groups are fused, and therefore, can induce high electron density and/or stabilization of the resonance structure in a device.

The copolymer according to one embodiment of the present specification can be used as a material of an organic material layer of an organic solar cell, and the organic solar cell including the copolymer can exhibit excellent properties in open voltage and short circuit current increases and/or an efficiency increase, and the like.

The copolymer according to one embodiment of the present specification may be used either alone or as a mixture with other materials in an organic solar cell, and an efficiency enhancement, a device lifespan enhancement due to properties such as thermal stability of compounds, and the like can be expected.

DESCRIPTION OF DRAWINGS

FIG. 1 is a diagram showing an organic solar cell according to one embodiment of the present specification.

FIG. 2 is a diagram showing an NMR spectrum of Chemical Formula 1-b.

FIG. 3 is a diagram showing an NMR spectrum of Chemical Formula 1-c.

FIG. 4 is a diagram showing an NMR spectrum of Chemical Formula 1-e.

FIG. 5 is a diagram showing an NMR spectrum of Chemical Formula 1-f.

FIG. 6 is a diagram showing an NMR spectrum of Chemical Formula 1-g.

FIG. 7 is a diagram showing an NMR spectrum of Chemical Formula 1-h.

FIG. 8 is a diagram showing an NMR spectrum of Chemical Formula 1-i.

FIG. 9 is a diagram showing an NMR spectrum of Chemical Formula 1-j.

FIG. 10 is a diagram showing an NMR spectrum of Chemical Formula 2-b.

FIG. 11 is a diagram showing an MS spectrum of Chemical Formula 2-b.

FIG. 12 is a diagram showing an NMR spectrum of Chemical Formula 3-a.

FIG. 13 is a diagram showing an NMR spectrum of Chemical Formula 3-b.

FIG. 14 is a diagram showing an NMR spectrum of Chemical Formula 5-e.

FIG. 15 is a diagram showing an NMR spectrum of Chemical Formula 6-b.

FIG. 16 is a diagram showing an NMR spectrum of Chemical Formula 7-a.

FIG. 17 is a diagram showing an NMR spectrum of Chemical Formula 8-b.

FIG. 18 is a diagram showing an MS spectrum of Chemical Formula 8-b.

FIG. 19 is a diagram showing an NMR spectrum of Chemical Formula 9-b.

FIG. 20 is a diagram showing an NMR spectrum of Chemical Formula 10-a.

FIG. 21 is a diagram showing an MS spectrum of Chemical Formula 11-a.

FIG. 22 is a diagram showing an NMR spectrum of Chemical Formula 11-a.

FIG. 23 is a diagram showing an NMR spectrum of Chemical Formula 12-a.

FIG. 24 is a diagram showing an NMR spectrum of Chemical Formula 13-b.

FIG. 25 is a diagram showing current density depending on the voltage of an organic solar cell according to Experimental Example 1.

FIG. 26 is a diagram showing current density depending on the voltage of an organic solar cell according to Experimental Example 2.

FIG. 27 is a diagram showing current density depending on the voltage of an organic solar cell according to Experimental Example 3.

FIG. 28 is a diagram showing current density depending on the voltage of an organic solar cell according to Experimental Example 4.

FIG. 29 is a diagram showing current density depending on the voltage of an organic solar cell according to Experimental Example 5.

FIG. 30 is a diagram showing current density depending on the voltage of an organic solar cell according to Experimental Example 6.

FIG. 31 is a diagram showing current density depending on the voltage of an organic solar cell according to Experimental Example 7.

FIG. 32 is a diagram showing current density depending on the voltage of an organic solar cell according to Experimental Example 8.

FIG. 33 is a diagram showing current density depending on the voltage of an organic solar cell according to Experimental Example 9.

FIG. 34 is a diagram showing current density depending on the voltage of an organic solar cell according to Experimental Example 10.

FIG. 35 is a diagram showing current density depending on the voltage of an organic solar cell according to Experimental Examples 11 to 14.

FIG. 36 is a diagram showing a UV-Vis absorption spectrum of Chemical Formula 1-1-14 in a solution state.

FIG. 37 is a diagram showing a UV-Vis absorption spectrum of Chemical Formula 1-1-14 in a film state.

FIG. 38 shows an electrochemical (cyclic voltammetry) measurement result of Chemical Formula 1-1-14.

FIG. 39 is a diagram showing a thermogravimetric analysis (TGA) result of Chemical Formula 1-1-14.

FIG. 40 is a diagram showing a UV-Vis absorption spectrum of Chemical Formula 1-1-15 in a solution state.

FIG. 41 is a diagram showing a UV-Vis absorption spectrum of Chemical Formula 1-1-15 in a film state.

FIG. 42 shows an electrochemical (cyclic voltammetry) measurement result of Chemical Formula 1-1-15.

FIG. 43 is a diagram showing a thermogravimetric analysis (TGA) result of Chemical Formula 1-1-15.

FIG. 44 is a diagram showing a UV-Vis absorption spectrum of Chemical Formula 1-1-16 in a solution state.

FIG. 45 is a diagram showing a UV-Vis absorption spectrum of Chemical Formula 1-1-16 in a film state.

FIG. 46 shows an electrochemical (cyclic voltammetry) measurement result of Chemical Formula 1-1-16.

FIG. 47 is a diagram showing a thermogravimetric analysis (TGA) result of Chemical Formula 1-1-16.

FIG. 48 is a diagram showing a UV-Vis absorption spectrum of Chemical Formula 1-1-17 in a solution state.

FIG. 49 is a diagram showing a UV-Vis absorption spectrum of Chemical Formula 1-1-17 in a film state.

FIG. 50 shows an electrochemical (cyclic voltammetry) measurement result of Chemical Formula 1-1-17.

FIG. 51 is a diagram showing a thermogravimetric analysis (TGA) result of Chemical Formula 1-1-17.

FIG. 52 is a diagram showing UV-Vis absorption spectra of Chemical Formulae 1-1-14 to 1-1-17 in a solution state.

FIG. 53 is a diagram showing UV-Vis absorption spectra of Chemical Formulae 1-1-14 to 1-1-17 in a film state.

FIG. 54 shows electrochemical measurement results (cyclic voltammetry) of Chemical Formulae 1-1-14 to 1-1-17.

FIG. 55 is a diagram showing thermogravimetric analysis (TGA) results of Chemical Formulae 1-1-14 to 1-1-17.

REFERENCE NUMBERS

101: Substrate
102: First Electrode
103: Hole Transfer Layer
104: Photoactive Layer
105: Second Electrode

MODE FOR DISCLOSURE

Hereinafter, the present specification will be described in detail.

In the present specification, a 'unit' is a repeated structure included in a monomer of a copolymer, and means a structure in which the monomer binds in the copolymer by polymerization.

In the present specification, the meaning of 'including a unit' means being included in a main chain in a polymer.

A copolymer according to one embodiment of the present specification includes a first unit represented by Chemical Formula 1 and a second unit represented by Chemical Formula 2.

The first unit and the second unit are provided so that S atoms of the thienothiophene groups are selectively close to each other.

In other words, a first unit represented by Chemical Formula 1 and a second unit represented by Chemical Formula 2 included in the copolymer according to one embodiment of the present specification have regioregularity binding in a certain direction in the copolymer. The copolymer having regioregularity according to one embodiment of the present specification relatively has excellent crystallinity.

Regioregularity in the present specification means steadily maintaining a direction in which a certain structure binds selectively in a copolymer.

The copolymer according to one embodiment of the present specification includes a structure in which two thiophene groups are fused, and thereby may induce high electron density and/or stabilization of the resonance structure in a device.

In one embodiment of the present specification, R1 is a substituted or unsubstituted carbonyl group.

In another embodiment, R1 is a substituted or unsubstituted ester group.

In one embodiment of the present specification, R2 is a substituted or unsubstituted carbonyl group.

In another embodiment, R2 is a substituted or unsubstituted ester group.

In one embodiment of the present specification, the unit represented by Chemical Formula 1 is represented by the following Chemical Formula 1-1 or Chemical Formula 1-2.

[Chemical Formula 1-1]

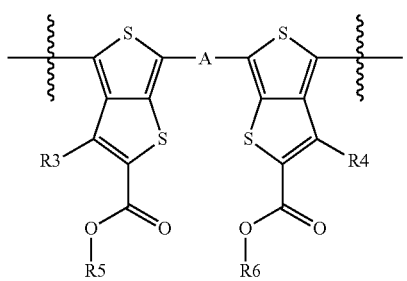

[Chemical Formula 1-2]

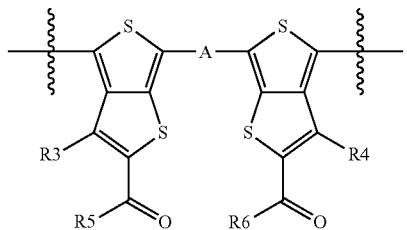

In Chemical Formula 1-1 and Chemical Formula 1-2,

A, R3 and R4 are the same as those defined in Chemical Formula 1, and

R5 and R6 are the same as or different from each other, and each independently hydrogen; a halogen group; a nitro group; a cyano group; a carboxyl group; a hydroxyl group; a substituted or unsubstituted carbonyl group; carbonyl group; a substituted or unsubstituted alkyl group; a substituted or unsubstituted allyl group; a substituted or unsubstituted alkoxy group; a substituted or unsubstituted cycloalkyl group; a substituted or unsubstituted alkenyl group; a substituted or unsubstituted ester group; a substituted or unsubstituted amide group; a substituted or unsubstituted ether group; a substituted or unsubstituted sulfonyl group; a substituted or unsubstituted sulfoxy group; a substituted or unsubstituted arylalkyl group; a substituted or unsubstituted aryl group; or a substituted or unsubstituted heterocyclic group including one or more of N, O, S and Se atoms.

In one embodiment, R1 is a carbonyl group substituted with a substituted or unsubstituted alkoxy group.

In one embodiment, R2 is a carbonyl group substituted with a substituted or unsubstituted alkoxy group.

In one embodiment, R1 is a carbonyl group substituted with a substituted or unsubstituted alkyl group.

In one embodiment, R2 is a carbonyl group substituted with a substituted or unsubstituted alkyl group.

In one embodiment of the present specification, the copolymer includes a unit represented by the following Chemical Formula 2.

[Chemical Formula 2]

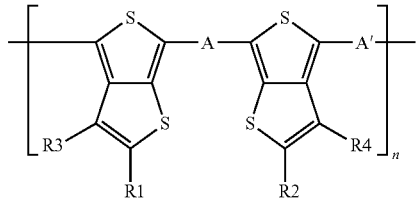

In Chemical Formula 2, n is an integer of 1 to 10,000,

R1 and R2 are the same as or different from each other, and each independently hydrogen; a halogen group; a nitro group; a cyano group; a carboxyl group; a hydroxyl group; a substituted or unsubstituted carbonyl group; a substituted or unsubstituted alkyl group; a substituted or unsubstituted allyl group; a substituted or unsubstituted alkoxy group; a substituted or unsubstituted cycloalkyl group; a substituted or unsubstituted alkenyl group; a substituted or unsubstituted ester group; a substituted or unsubstituted amide group; a substituted or unsubstituted ether group; a substituted or unsubstituted sulfonyl group; a substituted or unsubstituted sulfoxy group; a substituted or unsubstituted arylalkyl group; a substituted or unsubstituted aryl group; or a substituted or unsubstituted heterocyclic group including one or more of N, O, S and Se atoms, R3 and R4 are the same as or different from each other, and each independently hydrogen; or an electron withdrawing group, and A and A' are the same as or different from each other, and each independently a substituted or unsubstituted monocyclic or multicyclic aryl group; or a substituted or unsubstituted monocyclic or multicyclic heterocyclic group including one or more of N, O, S and Se atoms.

In one embodiment of the present specification, A functions as an electron donor or an electron acceptor in the copolymer.

In one embodiment of the present specification, A includes one, two or more of the following Chemical Formulae.

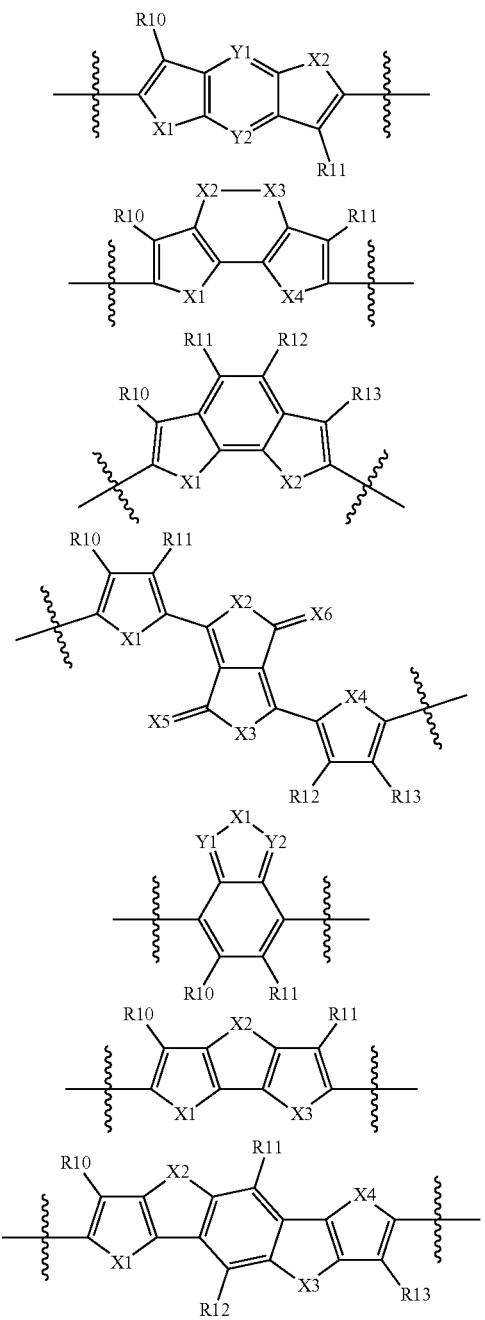

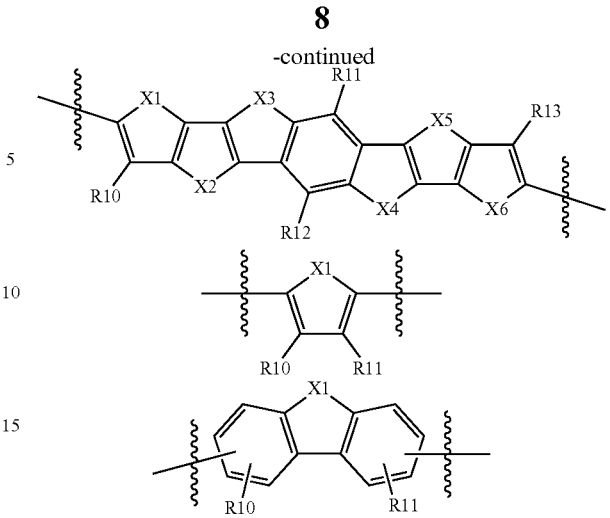

In the structures,

X1 to X6 are the same as or different from each other, and each independently CRR', NR, O, SiRR', PR, S, GeRR', Se or Te, Y1 and Y2 are the same as or different from each other, and each independently CR", N, SiR", P or GeR", and R', R", R''', R10 to R13 are the same as or different from each other, and each independently hydrogen; a halogen group; a nitro group; a cyano group; a carboxyl group; a hydroxyl group; a substituted or unsubstituted carbonyl group; a substituted or unsubstituted alkyl group; a substituted or unsubstituted allyl group; a substituted or unsubstituted alkoxy group; a substituted or unsubstituted cycloalkyl group; a substituted or unsubstituted alkenyl group; a substituted or unsubstituted ester group; a substituted or unsubstituted amide group; a substituted or unsubstituted ether group; a substituted or unsubstituted sulfonyl group; a substituted or unsubstituted sulfoxy group; a substituted or unsubstituted arylalkyl group; a substituted or unsubstituted aryl group; or a substituted or unsubstituted heterocyclic group including one or more of N, O, S and Se atoms.

In one embodiment of the present specification, A and A' are the same as or different from each other, and each independently have the following structure.

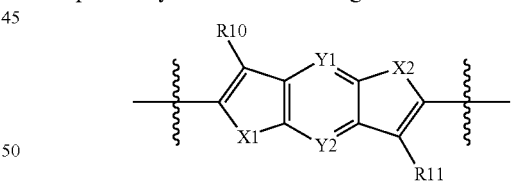

In one embodiment, A and A' are the same as or different from each other, and each independently have the following structure.

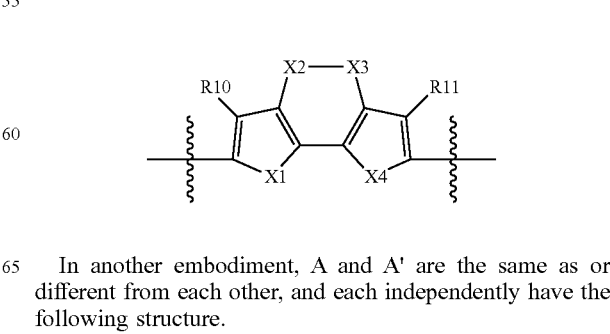

In another embodiment, A and A' are the same as or different from each other, and each independently have the following structure.

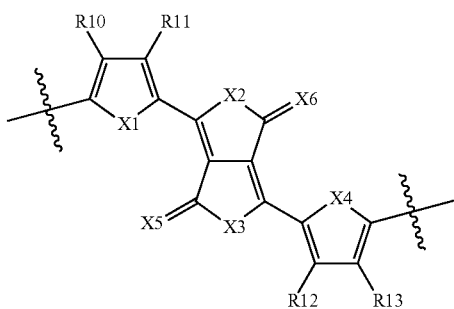

In another embodiment, A and A' are the same as or different from each other, and each independently have the following structure.

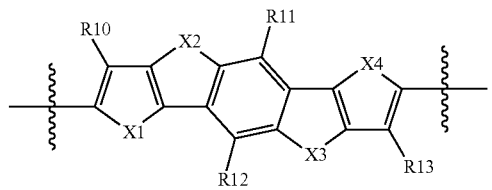

In another embodiment, A and A' are the same as or different from each other, and each independently have the following structure.

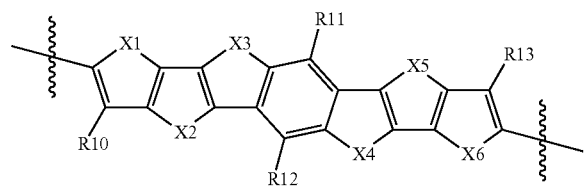

In another embodiment, A and A' are the same as or different from each other, and each independently have the following structure.

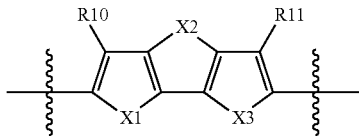

In one embodiment of the present specification, A and A' are the same as or different from each other, and each independently have the following structure.

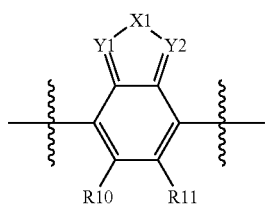

In another embodiment, A and A' are the same as or different from each other, and each independently have the following structure.

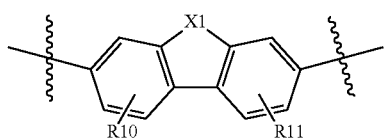

In the structures, X1 to X6, Y1, Y2, R10 to R13 are the same as those described above.

In one embodiment of the present specification, the copolymer includes a unit represented by any one of the following Chemical Formulae 3 to 10.

[Chemical Formula 3]

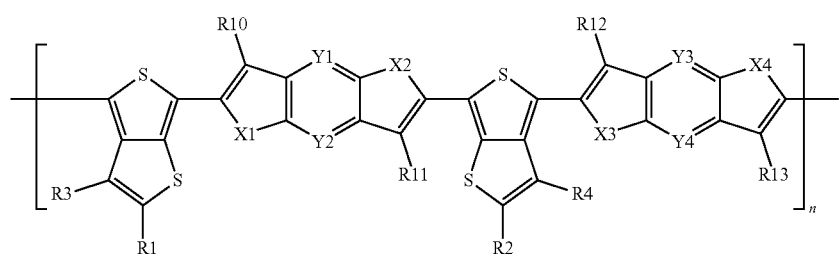

[Chemical Formula 4]

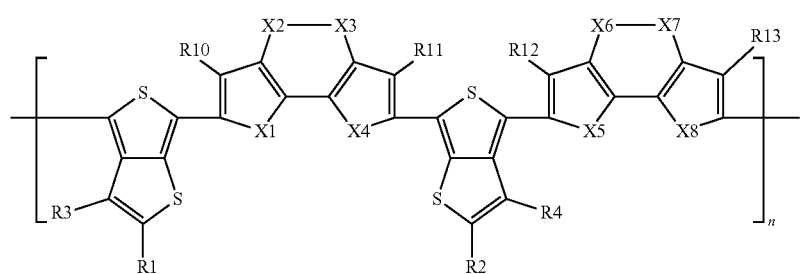

[Chemical Formula 5]
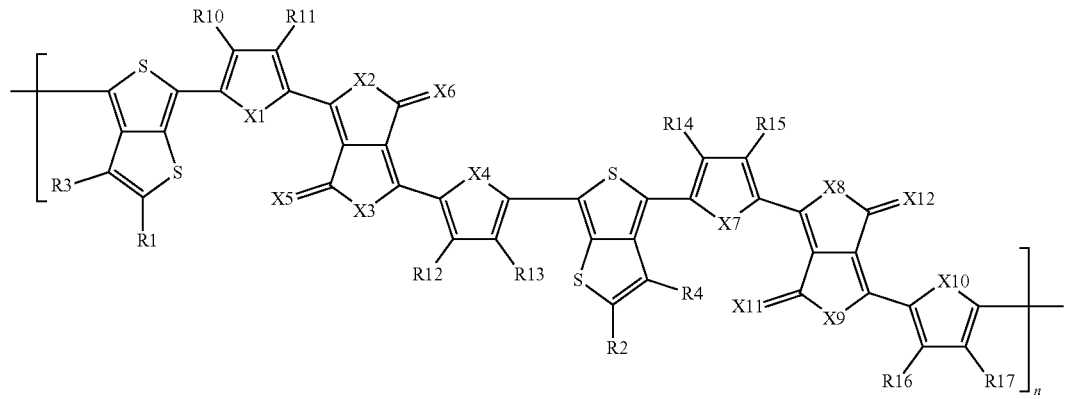
[Chemical Formula 6]
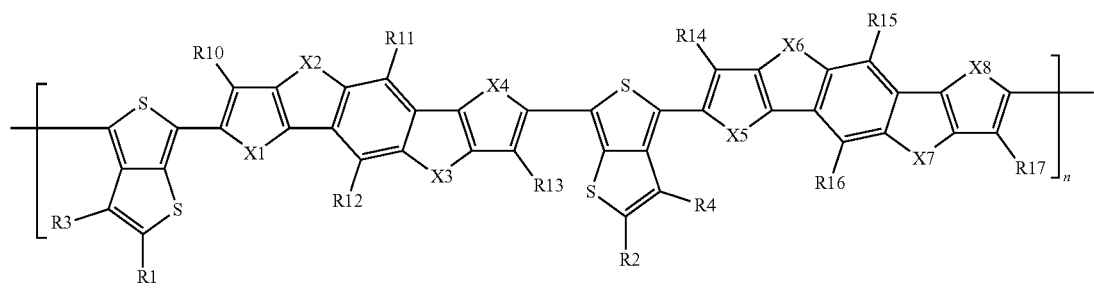
[Chemical Formula 7]
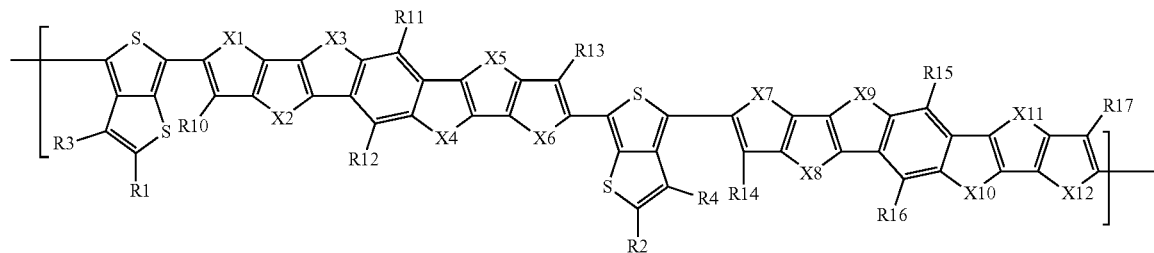
[Chemical Formula 8]
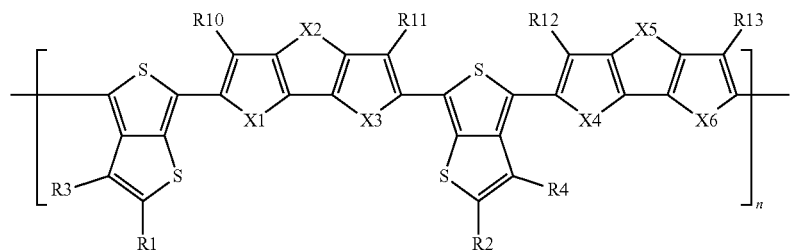
[Chemical Formula 9]
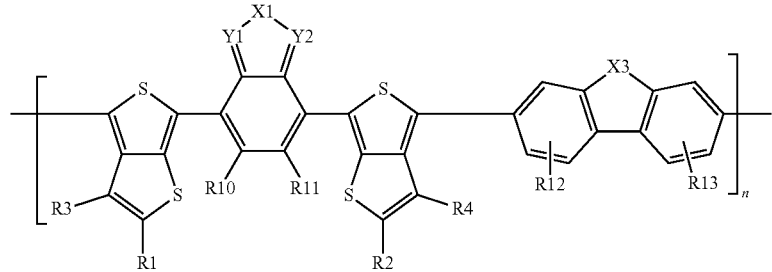

[Chemical Formula 10]

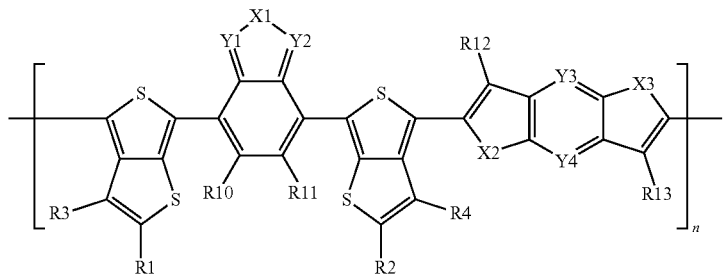

In Chemical Formulae 3 to 10, n is an integer of 1 to 10,000,

X1 to X12 are the same as or different from each other, and each independently CRR', NR, O, SiRR', PR, S, GeRR', Se or Te, Y1 to Y4 are the same as or different from each other, and each independently CR", N, SiR", P or GeR", R', R", R''', R1, R2, R10 to R17 are the same as or different from each other, and each independently hydrogen; a halogen group; a nitro group; a cyano group; a carboxyl group; a hydroxyl group; a substituted or unsubstituted carbonyl group; a substituted or unsubstituted alkyl group; a substituted or unsubstituted allyl group; a substituted or unsubstituted alkoxy group; a substituted or unsubstituted cycloalkyl group; a substituted or unsubstituted alkenyl group; a substituted or unsubstituted ester group; a substituted or unsubstituted amide group; a substituted or unsubstituted ether group; a substituted or unsubstituted sulfonyl group; a substituted or unsubstituted sulfoxy group; a substituted or unsubstituted arylalkyl group; a substituted or unsubstituted aryl group; or a substituted or unsubstituted heterocyclic group including one or more of N, O, S and Se atoms, and R3 and R4 are the same as or different from each other, and each independently hydrogen; or an electron withdrawing group.

In one embodiment of the present specification, the electron withdrawing group is a functional group pulling electrons, and means a functional group having relatively large electronegativity. Specifically, the electron withdrawing group is a halogen group.

In the present specification an 'terminal' means a structure of both ends except repeating units in a copolymer.

Examples of the substituents are described below, however, the substituents are not limited thereto.

The term "substitution" means a hydrogen atom bonding to a carbon atom of a compound is changed to another substituent, and the position of substitution is not limited as long as it is a position at which a hydrogen atom is substituted, that is, a position at which a substituent may substitute, and when two or more substituents substitute, the two or more substituents may be the same as or different from each other.

The term "substituted or unsubstituted" in the present specification means being substituted with one or more substituents selected from the group consisting of deuterium; a halogen group; an alkyl group; an alkenyl group; an alkoxy group; an ester group; a carbonyl group; a carboxyl group; a hydroxyl group; a cycloalkyl group; a silyl group; an arylalkenyl group; an aryloxy group; an alkylthioxy group; an alkylsulfoxy group; an arylsulfoxy group; a boron group; an alkylamine group; an aralkylamine group; an arylamine group; a heterocyclic group; an arylamine group; an aryl group; a nitrile group; a nitro group; a hydroxyl group; and a heterocyclic group including one or more of N, O and S atoms, or having no substituents.

The substituents may be substituted with additional substituents, or unsubstituted.

In the present specification, the halogen group may include fluorine, chlorine, bromine or iodine.

In the present specification, the carbonyl group may be represented by

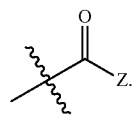

Z is hydrogen; a substituted or unsubstituted alkyl group having 1 to 20 carbon atoms; a substituted or unsubstituted cycloalkyl group having 3 to 60 carbon atoms; a substituted or unsubstituted alkoxy group having 1 to 20 carbon atoms; a substituted or unsubstituted arylalkyl group having 7 to 50 carbon atoms; a substituted or unsubstituted aryl group having 6 to 60 carbon atoms; or a substituted or unsubstituted heterocyclic group having 2 to 60 carbon atoms and including one or more of N, O, S and Se atoms.

In the present specification, in the amide group, the nitrogen of the amide group may be once or twice substituted with hydrogen, a linear, branched or cyclic alkyl group having 1 to 25 carbon atoms, or an aryl group having 6 to 25 carbon atoms. Specifically, compounds having the following structural formulae may be included, but the compound is not limited thereto.

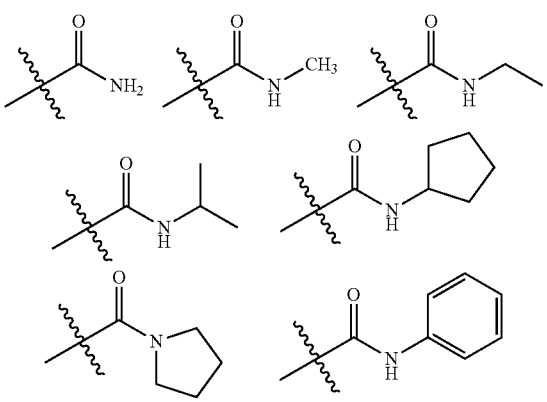

-continued

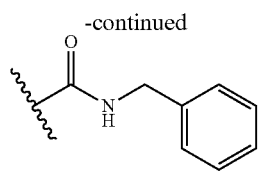

In the present specification, in the ester group, the oxygen of the ester group may be substituted with a linear, branched or cyclic alkyl group having 1 to 25 carbon atoms or an aryl group having 6 to 25 carbon atoms. Specifically, compounds having the following structural formulae may be included, but the compound is not limited thereto.

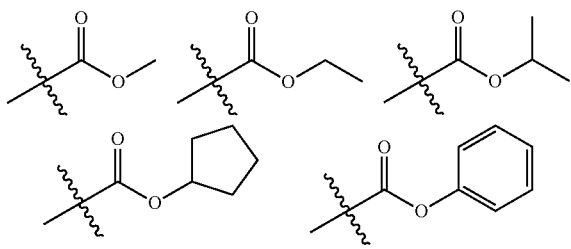

In the present specification, the alkyl group may be linear or branched, and the number of carbon atoms is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 60 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably 1 to 20. Specific examples thereof may include methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the alkenyl group may be linear or branched, and although not particularly limited thereto, the number of carbon atoms is preferably 2 to 40. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the number of carbon atoms in the arylalkyl group is not particularly limited, however, in one embodiment of the present specification, the number of carbon atoms in the arylalkyl group is 7 to 50. Specifically, the aryl part has 6 to 49 carbon atoms, and the alkyl part has 1 to 44 carbon atoms. Specific examples thereof include a benzyl group, a p-methylbenzyl group, an m-methylbenzyl group, a p-ethylbenzyl group, an m-ethylbenzyl group, a 3,5-dimethylbenzyl group, an α-methylbenzyl group, an α,α-dimethylbenzyl group, an α,α-methylphenylbenzyl group, a 1-naphthylbenzyl group, a 2-naphthylbenzyl group, a p-fluorobenzyl group, a 3,5-difluorobenzyl group, an α,α-ditrifluoromethylbenzyl group, a p-methoxybenzyl group, an m-methoxybenzyl group, an α-phenoxybenzyl group, an α-benzyloxybenzyl group, a naphthylmethyl group, a naphthylethyl group, a naphthylisopropyl group, a pyrrolylmethyl group, a pyrrolylethyl group, an aminobenzyl group, a nitrobenzyl group, a cyanobenzyl group, a 1-hydroxy-2-phenylisopropyl group, a 1-chloro-2-phenylisopropyl group and the like, but are not limited thereto.

In the present specification, the aryl group may be a monocyclic aryl group or a multicyclic aryl group, and includes a case in which an alkyl group having 1 to 25 carbon atoms or an alkoxy group having 1 to 25 carbon atoms is substituted. In addition, the aryl group in the present specification may mean an aromatic ring.

When the aryl group is a monocyclic aryl group, the number of carbon atoms is not particularly limited, but is preferably 6 to 25. Specific examples of the monocyclic aryl group may include a phenyl group, a biphenyl group, a terphenyl, a stilbenyl group and the like, but are not limited thereto.

When the aryl group is a multicyclic aryl group, the number of carbon atoms is not particularly limited, but is preferably 10 to 24. Specific example of the multicyclic aryl group may include a naphthyl group, an anthracenyl group, a phenanthryl group, a pyrenyl group, a perylenyl group, a crycenyl group, a fluorenyl group and the like, but are not limited thereto.

In the present specification, the fluorenyl group may be substituted, and adjacent substituents may bond to each other to form a ring.

When the fluorenyl group is substituted,

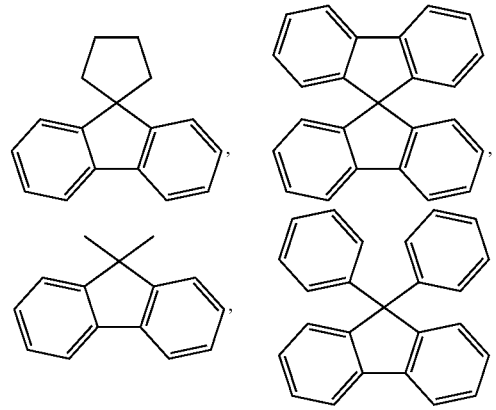

and the like may be included. However, the structure is not limited thereto.

In the present specification, the heterocyclic group is a heterocyclic group including one or more of N, O, S and Se as a heteroatom, and although not particularly limited, the number of carbon atoms is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group and the like, but are not limited thereto.

The heterocyclic group may be monocyclic or multicyclic, and may be aromatic, aliphatic, or a fused ring of aromatic and aliphatic.

In another embodiment, R1 is a substituted or unsubstituted ester group.

In one embodiment of the present specification, R1 is an ester group substituted with an alkyl group.

In another embodiment, R1 is an ester group substituted with a 2-ethylhexyl group.

In another embodiment, R1 is a substituted or unsubstituted carbonyl group.

In one embodiment of the present specification, R1 is a carbonyl group substituted with an alkyl group.

In another embodiment, R1 is a carbonyl group substituted with a 3-heptenyl group.

In another embodiment, R2 is a substituted or unsubstituted ester group.

In one embodiment, R2 is an ester group substituted with an alkyl group.

In one embodiment of the present specification, R2 is an ester group substituted with a 2-ethylhexyl group.

In another embodiment, R2 is a substituted or unsubstituted carbonyl group.

In one embodiment of the present specification, R2 is a carbonyl group substituted with an alkyl group.

In another embodiment, R2 is a carbonyl group substituted with a 3-heptenyl group.

In one embodiment of the present specification, R5 is a substituted or unsubstituted alkyl group.

In one embodiment of the present specification, R5 is a substituted or unsubstituted 2-ethylhexyl group; or a substituted or unsubstituted 3-heptenyl group.

In one embodiment, R5 is a 2-ethylhexyl group; or a 3-heptenyl group.

In one embodiment of the present specification, R6 is a substituted or unsubstituted alkyl group.

In one embodiment of the present specification, R6 is a substituted or unsubstituted 2-ethylhexyl group; or a substituted or unsubstituted 3-heptenyl group.

In one embodiment, R6 is a 2-ethylhexyl group; or a 3-heptenyl group.

In one embodiment of the present specification, R3 is hydrogen.

In another embodiment, R4 is hydrogen.

In one embodiment of the present specification, R10 is hydrogen.

In another embodiment of the present specification, R11 is hydrogen.

In one embodiment of the present specification, R12 is hydrogen.

In another embodiment, R13 is hydrogen.

In one embodiment of the present specification, R14 is hydrogen.

In one embodiment of the present specification, R15 is hydrogen.

In another embodiment, R16 is hydrogen.

In another embodiment, R17 is hydrogen.

In one embodiment of the present specification, X1 is S.

In another embodiment, X2 is S.

In one embodiment of the present specification, X2 is CRR'.

In another embodiment, X2 is NR.

In one embodiment, X2 is SiRR'.

In one embodiment of the present specification, X3 is S.

In another embodiment, X3 is O.

In another embodiment, X3 is NR.

In another embodiment, X3 is CRR'.

In another embodiment, X3 is SiRR'.

In another embodiment, X4 is S.

In another embodiment, X4 is CRR'.

In another embodiment, X5 is S.

In one embodiment of the present specification, X5 is O.

In one embodiment of the present specification, X5 is SiRR'.

In one embodiment of the present specification, X6 is CRR'.

In one embodiment of the present specification, X6 is SiRR'.

In another embodiment, X6 is O.

In another embodiment, X6 is S.

In one embodiment of the present specification, X7 is O.

In another embodiment, X7 is S.

In another embodiment, X7 is CRR'.

In one embodiment of the present specification, X7 is SiRR'.

In another embodiment, X8 is S.

In one embodiment of the present specification, X8 is NR.

In another embodiment, X9 is NR.

In another embodiment, X9 is CRR'.

In one embodiment of the present specification, X10 is CRR'.

In another embodiment, X10 is S.

In one embodiment, X11 is O.

In another embodiment, X11 is S.

In one embodiment of the present specification, X12 is O.

In another embodiment, X12 is S.

In one embodiment of the present specification, R and R' are the same as or different from each other, and each independently a substituted or unsubstituted alkyl group; a substituted or unsubstituted alkoxy group; or a substituted or unsubstituted aryl group.

In one embodiment of the present specification, R is a substituted or unsubstituted alkyl group.

In one embodiment, R is a linear or branched alkyl group.

In one embodiment, R is a substituted or unsubstituted octyl group.

In another embodiment, R is an octyl group.

In one embodiment of the present specification, R is a substituted or unsubstituted 2-ethylhexyl group.

In one embodiment, R is a 2-ethylhexyl group.

In one embodiment of the present specification, R is a substituted or unsubstituted 3,7-dimethyloctyl group.

In one embodiment of the present specification, R is a 3,7-dimethyloctyl group.

In one embodiment of the present specification, R is a substituted or unsubstituted aryl group.

In one embodiment of the present specification, R is a substituted or unsubstituted phenyl group.

In one embodiment of the present specification, R is a phenyl group substituted with a substituted or unsubstituted alkyl group.

In one embodiment of the present specification, R is a phenyl group substituted with an alkyl group.

In one embodiment of the present specification, R is a phenyl group substituted with a hexyl group.

In one embodiment of the present specification, R' is a substituted or unsubstituted alkyl group.

In one embodiment, R' is a linear or branched alkyl group.

In another embodiment, R' is a substituted or unsubstituted octyl group.

In another embodiment, R' is an octyl group.

In one embodiment of the present specification, R' is a substituted or unsubstituted 2-ethylhexyl group.

In one embodiment, R' is a 2-ethylhexyl group.

In one embodiment of the present specification, R' is a substituted or unsubstituted 3,7-dimethyloctyl group.

In one embodiment of the present specification, R' is a 3,7-dimethyloctyl group.

In one embodiment of the present specification, R' is a substituted or unsubstituted aryl group.

In one embodiment of the present specification, R' is a substituted or unsubstituted phenyl group.

In one embodiment of the present specification, R' is a phenyl group substituted with a substituted or unsubstituted alkyl group.

In one embodiment of the present specification, R' is a phenyl group substituted with an alkyl group.

In one embodiment of the present specification, R' is a phenyl group substituted with a hexyl group.

In one embodiment of the present specification, Y1 is CR".

In one embodiment of the present specification, Y1 is N.

In another embodiment, Y2 is CR".

In one embodiment of the present specification, Y2 is N.

In one embodiment of the present specification, Y3 is CR".

In another embodiment, Y4 is CR".

In one embodiment of the present specification, R" is a substituted or unsubstituted alkoxy group; or a substituted or unsubstituted heterocyclic group including one or more of N, O, S and Se atoms.

In one embodiment of the present specification, R" is a substituted or unsubstituted alkoxy group.

In another embodiment, R" is a substituted or unsubstituted 2-ethylhexyloxy group.

In one embodiment of the present specification, R" is a 2-ethylhexyloxy group.

In one embodiment of the present specification, R" is a substituted or unsubstituted hexyloxy group.

In one embodiment, R" is a hexyloxy group.

In one embodiment of the present specification, R" is a substituted or unsubstituted heterocyclic group including one or more of N, O, S and Se atoms.

In one embodiment of the present specification, R" is a substituted or unsubstituted heterocyclic group including one or more S atoms.

In one embodiment of the present specification, R" is a substituted or unsubstituted thiophene group.

In one embodiment of the present specification, R" is a thiophene group substituted with a substituted or unsubstituted alkyl group.

In one embodiment of the present specification, R" is a thiophene group substituted with a substituted or unsubstituted 2-ethylhexyl group.

In one embodiment of the present specification, R" is a thiophene group substituted with a 2-ethylhexyl group.

In one embodiment of the present specification, R" is a thiophene group substituted with a substituted or unsubstituted hexyl group.

In one embodiment of the present specification, R" is a thiophene group substituted with a hexyl group.

In one embodiment of the present specification, R" is a substituted or unsubstituted heterocyclic group including one or more Se atoms.

In one embodiment of the present specification, R" is a substituted or unsubstituted selenophene group.

In one embodiment of the present, specification, R" is a selenophene group substituted with a substituted or unsubstituted alkyl group.

In one embodiment of the present specification, R" is a selenophene group substituted with a substituted or unsubstituted 2-ethylhexyl group.

In one embodiment of the present specification, R" is a selenophene group substituted with a 2-ethylhexyl group.

In one embodiment of the present specification, R" is a selenophene group substituted with a substituted or unsubstituted 2-hexyldecanyl group.

In one embodiment of the present specification, R" is a selenophene group substituted with a 2-hexyldecanyl group.

In one embodiment of the present specification, the copolymer is represented by any one of the following Chemical Formula 1-1-1 to Chemical Formula 1-1-17.

[Chemical Formula 1-1-1]

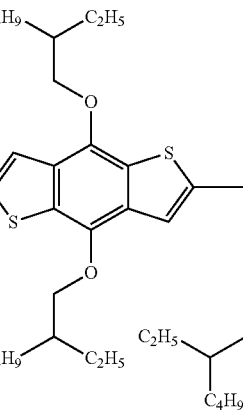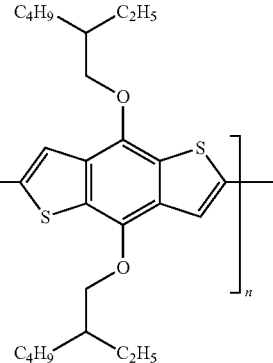

[Chemical Formula 1-1-2]
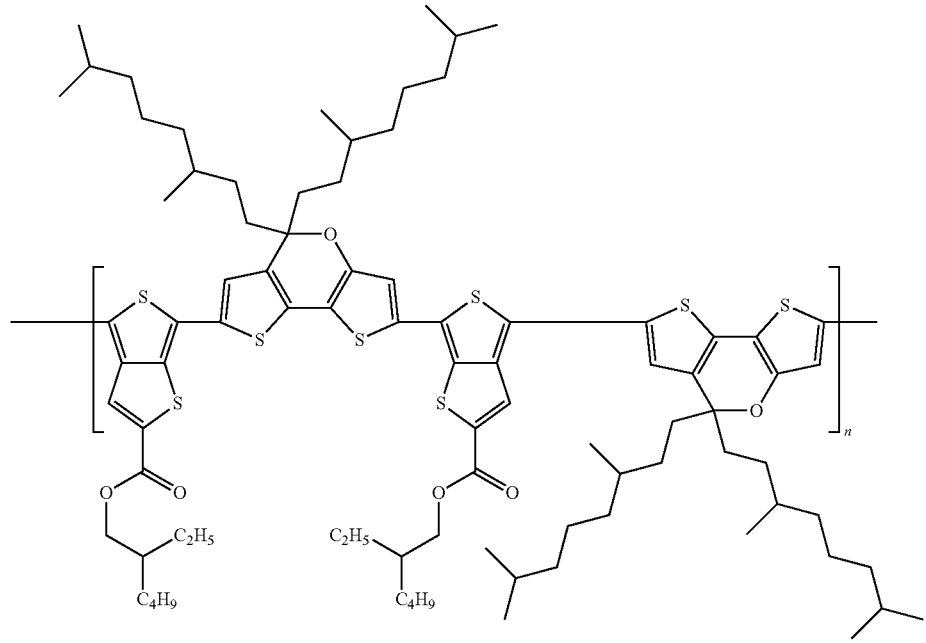
[Chemical Formula 1-1-3]
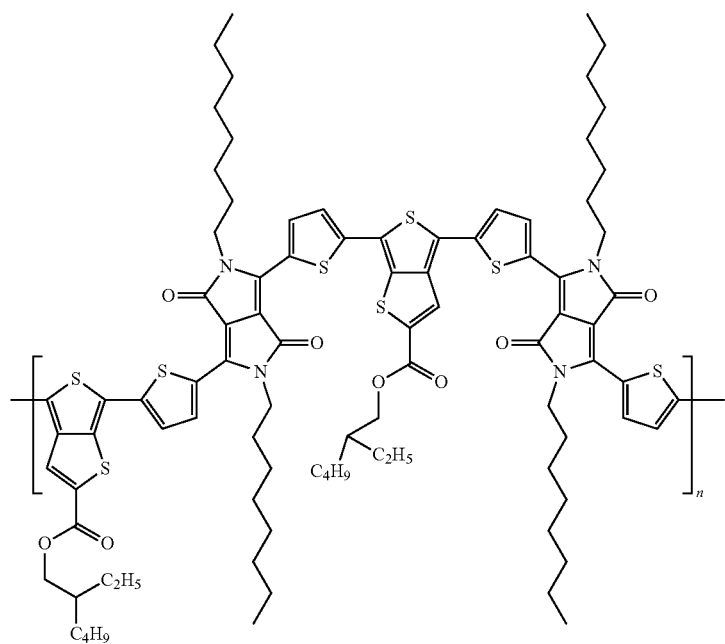

[Chemical Formula 1-1-4]
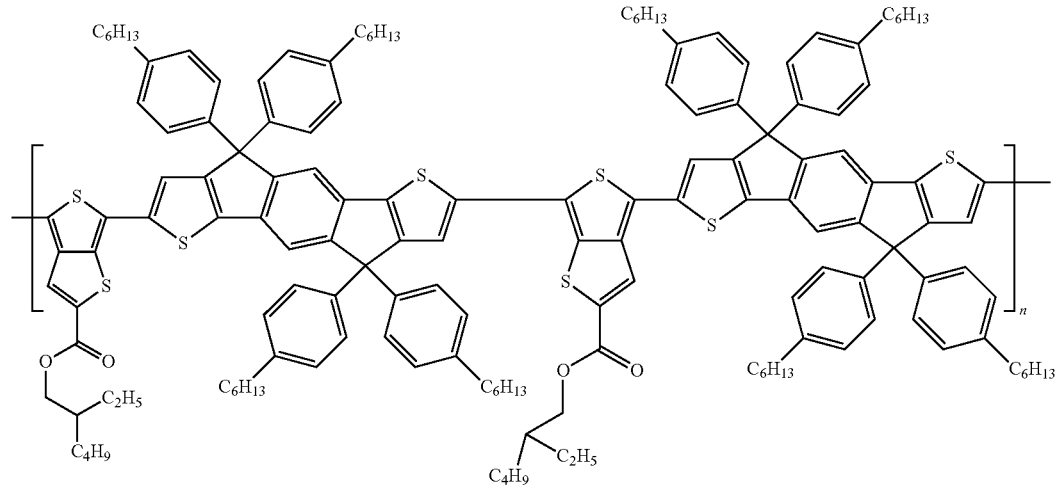
[Chemical Formula 1-1-5]
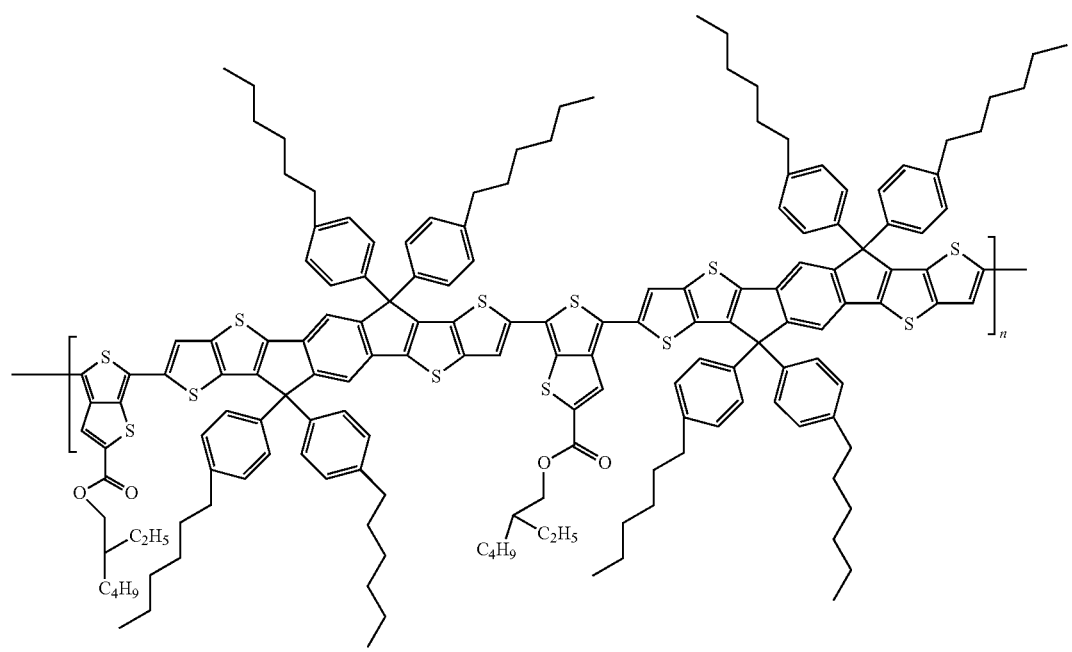
[Chemical Formula 1-1-6]
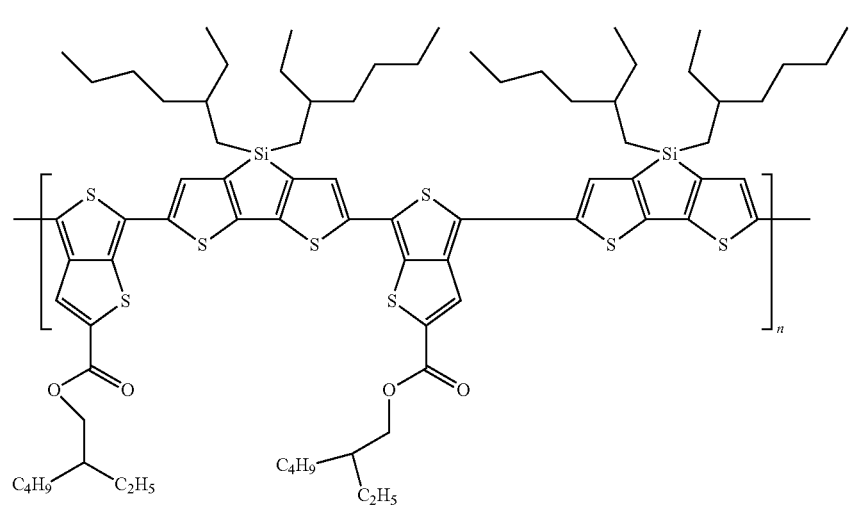

[Chemical Formula 1-1-7]
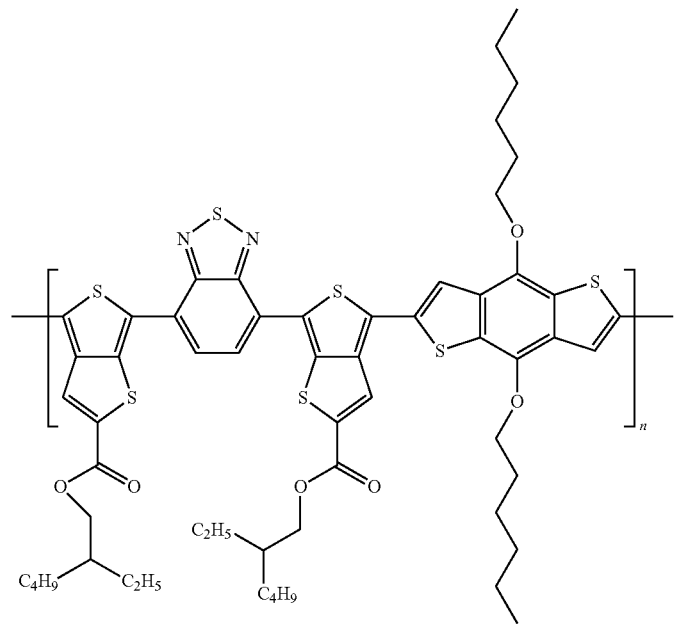
[Chemical Formula 1-1-8]
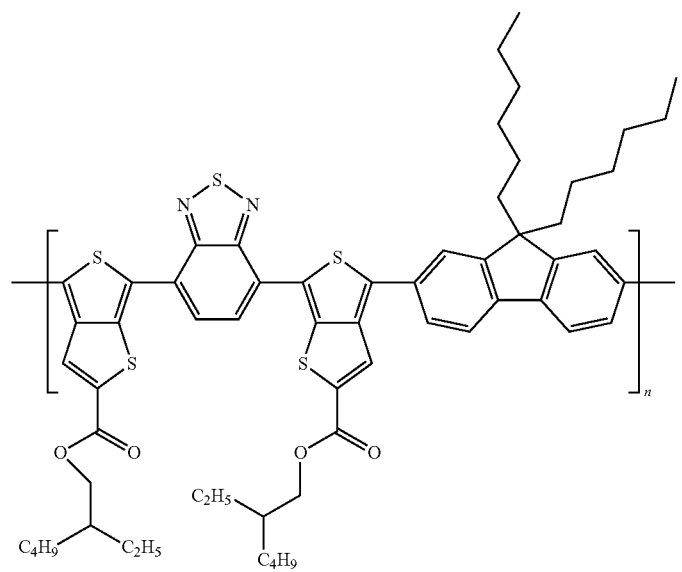

[Chemical Formula 1-1-9]
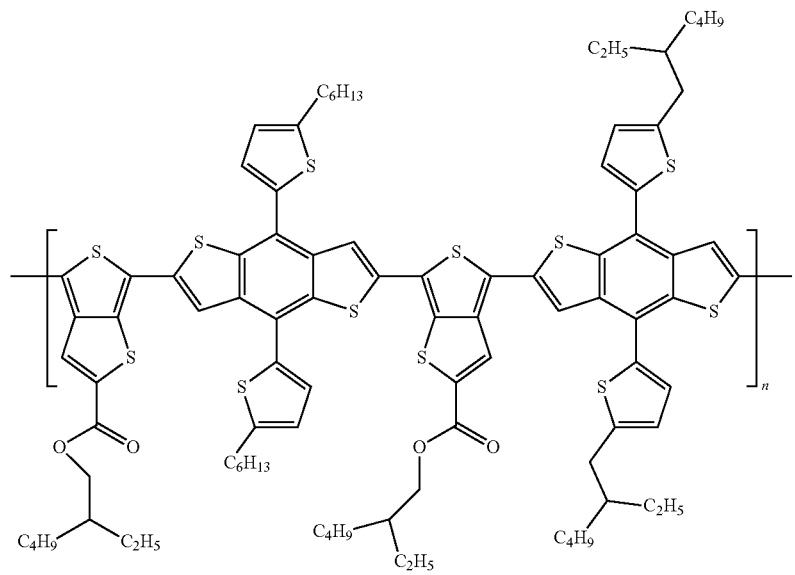
[Chemical Formula 1-1-10]
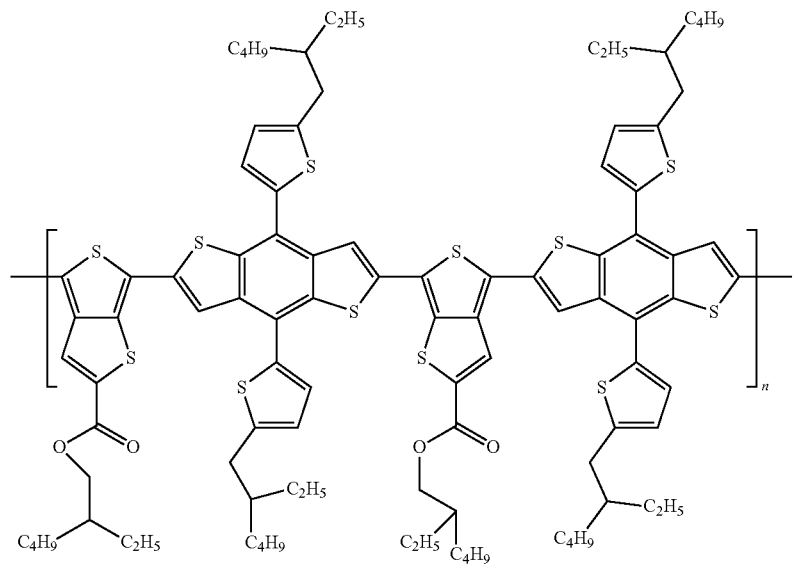

[Chemical Formula 1-1-11]
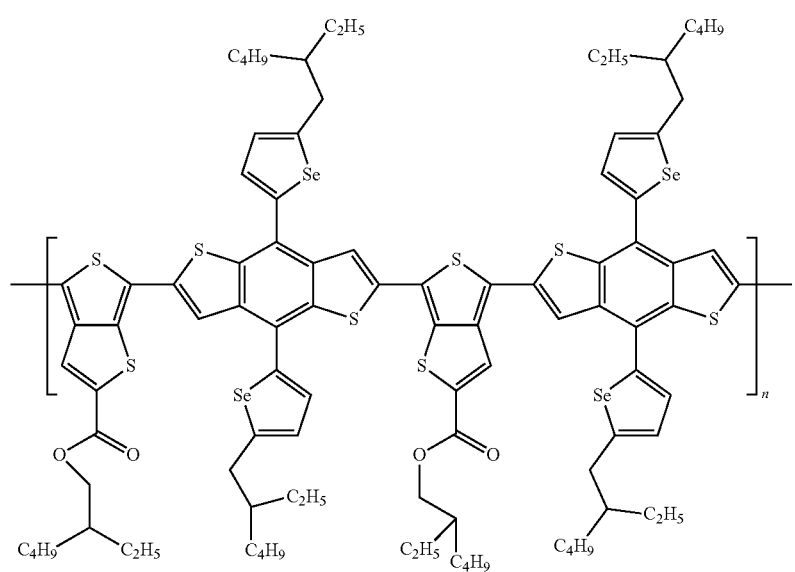
[Chemical Formula 1-1-12]
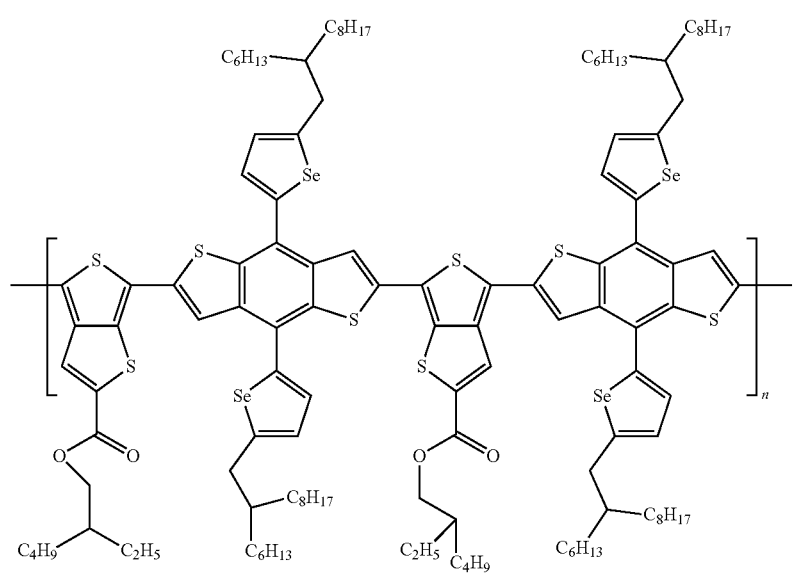
[Chemical Formula 1-1-13]
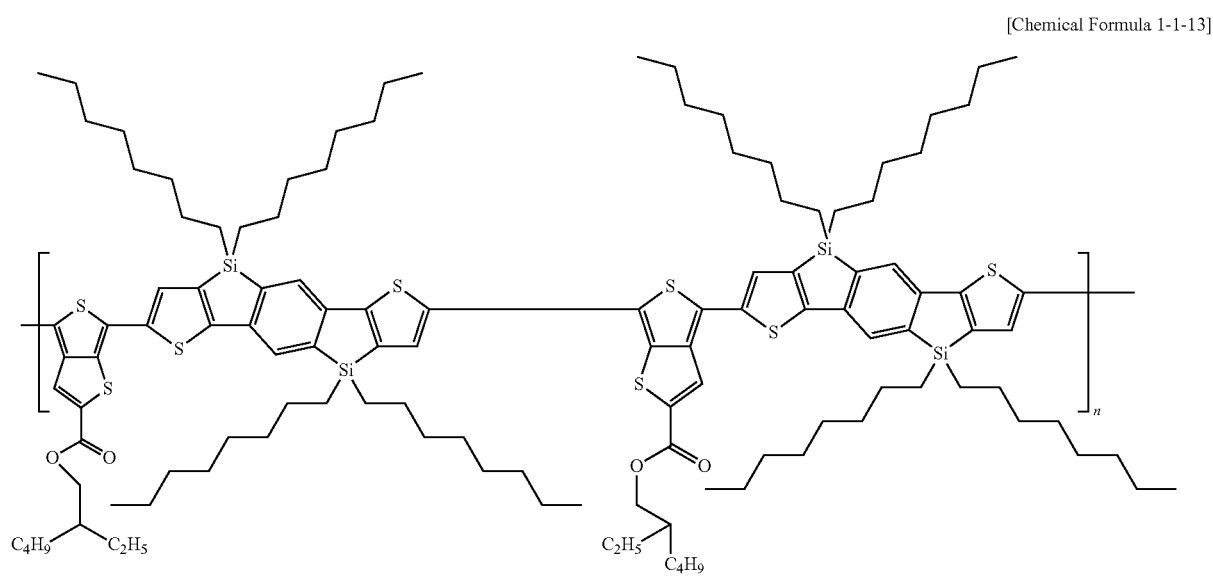

[Chemical Formula 1-1-14]
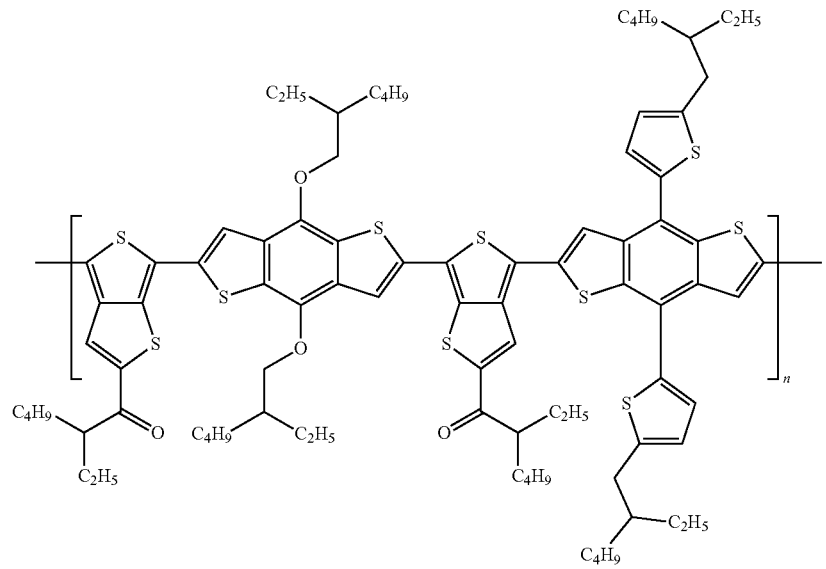
[Chemical Formula 1-1-15]
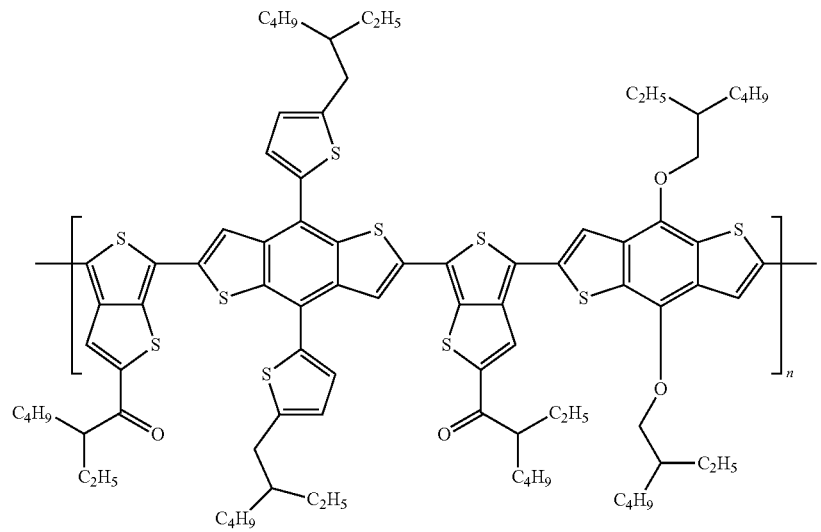
[Chemical Formula 1-1-16]
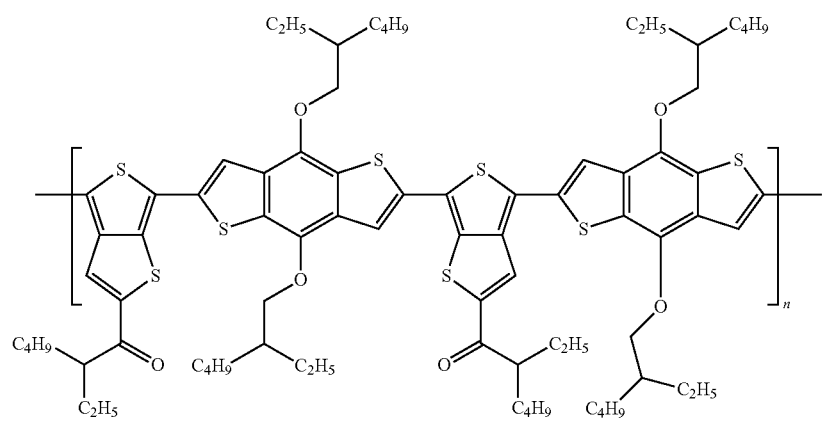

-continued

[Chemical Formula 1-1-17]

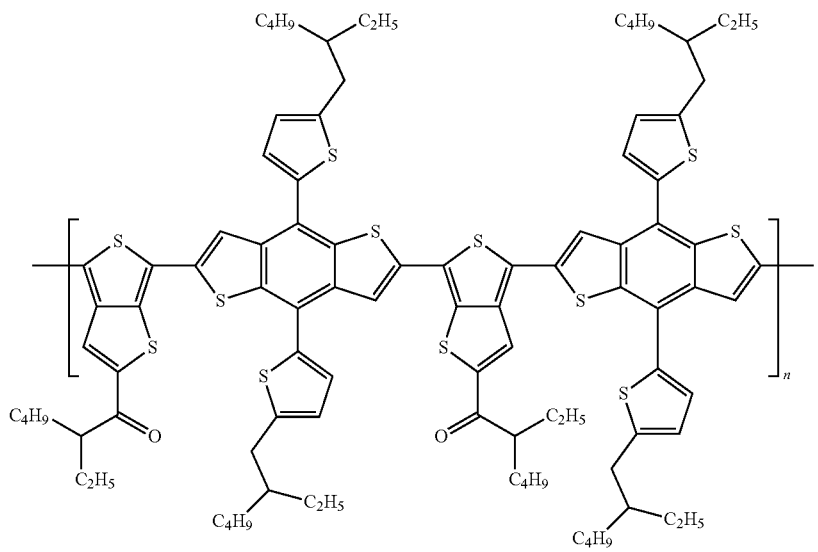

In Chemical Formulae 1-1-1 to 1-1-17, n is the same as n defined above.

In one embodiment of the present specification, the terminal group of the copolymer is a heterocyclic group or an aryl group.

In one embodiment of the present specification, the terminal group of the copolymer is a 4-(trifluoromethyl)phenyl group.

According to one embodiment of the present specification, the copolymer preferably has a number average molecular weight of 500 g/mol to 1,000,000 g/mol. Preferably, the copolymer has a number average molecular weight of 10,000 to 100,000. In one embodiment of the present specification, the copolymer has a number average molecular weight of 30,000 to 100,000.

According to one embodiment of the present specification, the copolymer may have a molecular weight distribution of 1 to 100. Preferably, the copolymer has a molecular weight distribution of 1 to 3.

As the molecular weight distribution decreases and the number average molecular weight increases, electrical properties and mechanical properties become favorable.

In addition, the number average molecular weight is preferably 100,000 or less in order to have solubility above a certain level and thereby favorably apply a solution coating method.

The copolymer may be prepared based on the preparation examples described later.

In the present invention, 1 equivalent of bromine is reacted to a thienothiophene group each substituted with R1 and R2, and bromination occurs in the S atom direction of the thienothiophene group, and by polymerizing each unit, the copolymer including the first unit and the second unit may be prepared as well as the copolymer represented by Chemical Formula 1-1-1.

The copolymer according to the present specification may be prepared using a multi-step chemical reaction. After monomers are prepared through an alkylation reaction, a Grignard reaction, a Suzuki coupling reaction, a Stille coupling reaction and the like, final copolymers may be prepared through a carbon-carbon coupling reaction such as a Stille coupling reaction. When a substituent to introduce is a boronic acid or a boronic ester compound, a Suzuki coupling reaction may be used, and when a substituent to introduce is a tributyltin or trimethyltin compound, a Stille coupling reaction may be used, however, the method is not limited thereto.

One embodiment of the present specification provides an organic solar cell including a first electrode; a second electrode provided opposite to the first electrode; and one or more organic material layers provided between the first electrode and the second electrode and including a photoactive layer, wherein one or more layers of the organic material layers include the copolymer described above.

The organic solar cell according to one embodiment of the present specification includes a first electrode, a photoactive layer and a second electrode. The organic solar cell may further include a substrate, a hole transfer layer and/or an electron transfer layer.

In one embodiment of the present specification, when the organic solar cell receives photons from an external light source, electrons and holes are generated between an electron donor and an electron acceptor. The generated holes are transferred to an anode through the electron donor layer.

In one embodiment of the present specification, the organic material layer includes a hole transfer layer, a hole injection layer, or a layer carrying out hole transfer and hole injection at the same time, and the hole transfer layer, the hole injection layer, or the layer carrying out hole transfer and hole injection at the same time includes the copolymer.

In another embodiment, the organic material layer includes an electron injection layer, an electron transfer layer, or a layer carrying out electron injection and electron transfer at the same time, and the electron injection layer, the electron transfer layer, or the layer carrying out electron injection and electron transfer at the same time includes the copolymer.

FIG. 1 is a diagram showing an organic solar cell according to one embodiment of the present specification.

In one embodiment of the present specification, the organic solar cell may further include additional organic material layers. The organic solar cell may reduce the number of organic material layers by using an organic material having various functions at the same time.

In one embodiment of the present specification, the first electrode is an anode, and the second electrode is a cathode. In another embodiment, the first electrode is a cathode, and the second electrode is an anode.

In one embodiment of the present specification, the organic solar cell may have a structure in which the cathode, the photoactive layer and the anode are arranged in consecutive order, or may have a structure in which the anode, the photoactive layer and the cathode are arranged in consecutive order, however, the structure is not limited thereto.

In another embodiment, the organic solar cell may have a structure in which the anode, the hole transfer layer, the photoactive layer, the electron transfer layer and the cathode are arranged in consecutive order, or may have a structure in which the cathode, the electron transfer layer, the photoactive layer, the hole transfer layer and the anode are arranged in consecutive order, however, the structure is not limited thereto.

In one embodiment of the present specification, the organic solar cell has a normal structure.

In one embodiment of the present specification, the organic solar cell has an inverted structure.

In one embodiment of the present specification, the organic solar cell has a tandem structure.

The organic solar cell according to one embodiment of the present invention may have one, two or more of the photoactive layers.

In another embodiment, a buffer layer may be provided between the photoactive layer and the hole transfer layer, or between the photoactive layer and the electron transfer layer. Herein, the hole injection layer may be further provided between the anode and the hole transfer layer. In addition, the electron injection layer may be further provided between the cathode and the electron transfer layer.

In one embodiment of the present specification, the photoactive layer includes one, two or more selected from the group consisting of an electron donor and an electron acceptor, and the electron donor material includes the copolymer.

In one embodiment of the present specification, the electron acceptor material may be selected from the group consisting of fullerene, fullerene derivatives, bathocuproine, semiconductor elements, semiconductor compounds, and combinations thereof. Specifically, one, two or more selected from the group consisting of fullerene, fullerene derivatives ((6,6)-phenyl-$C_{61}$-butyric acid-methylester (PCBM) or (6,6)-phenyl-$C_{61}$-butyric acid-cholesteryl ester (PCBCR)), perylene, polybenzimidazole (PBI), and 3,4,9, 10-perylene-tetracarboxylic bis-benzimidazole (PTCBI) may be included.

In one embodiment of the present specification, the electron donor and the electron acceptor form a bulk heterojunction (BHJ).

A Bulk heterojunction means an electron donor material and an electron acceptor material being mixed together in a photoactive layer.

In one embodiment of the present specification, the photoactive layer has a bilayer structure including an n-type organic material layer and a p-type organic material layer, and the p-type organic material layer includes the copolymer.

The substrate in the present specification may include a glass substrate or a transparent plastic substrate having excellent transparency, surface smoothness, handling easiness and water resistance, but is not limited thereto, and substrates typically used in organic solar cells may be used without limit. Specific examples thereof include glass, polyethylene terphthalate (PET), polyethylene naphthalate (PEN), polypropylene (PP), polyimide (PI), triacetyl cellulose (TAC) and the like, but are not limited thereto.

The anode electrode may include a material that is transparent and has excellent conductivity, but the material is not limited thereto. Examples of the anode material include metals such as vanadium, chromium, copper, zinc or gold, or alloys thereof; metal oxides such as zinc oxides, indium oxides, indium tin oxides (ITO) or indium zinc oxides (IZO); and a combination of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

A method of forming the anode electrode is not particularly limited, however, the anode electrode may be formed by being applied to one surface of a substrate or coated in the form of a film using a method such as sputtering, E-beam, thermal deposition, spin coating, screen printing, ink jet printing, doctor blade or gravure printing.

When the anode electrode is formed on a substrate, the result may go through processes of cleaning, dehydrating and modifying to be hydrophilic.

For example, after a patterned ITO substrate is cleaned with a cleaning agent, acetone and isopropyl alcohol (IPA) in consecutive order, the ITO substrate is dried for 1 to 30 minutes at 100° C. to 150° C., preferably for 10 minutes at 120° C., on a heating plate in order to remove moisture, and when the substrate is completely cleaned, the surface of the substrate is modified to be hydrophilic.

Through the surface modification such as above, the junctional surface potential may be maintained at a level suitable for the surface potential of a photoactive layer. In addition, when a surface is modified, a polymer thin film may be readily formed on an anode electrode, and the quality of the thin film may be improved.

Preprocessing technologies for an anode electrode include a) a surface oxidation method using parallel plate discharge, b) a method of oxidizing the surface through the ozone generated by UV rays in a vacuum, and c) an oxidation method using the oxygen radicals generated by plasma.

One of the methods described above may be selected depending on the condition of an anode electrode or a substrate. However, it is commonly preferable to prevent the leave of oxygen on the surface of an anode electrode or a substrate and to suppress the remaining of moisture and organic materials as much as possible, no matter which method is used. In this case, practical effects of the preprocessing may be maximized.

As a specific example, a method of oxidizing the surface through the ozone generated by UV rays may be used. Herein, a patterned ITO substrate may be fully dried by baking the patterned ITO substrate on a hot plate after being ultrasonic cleaned, and the patterned ITO substrate is introduced into a chamber and then may be cleaned by the ozone generated by reacting oxygen gas with UV light using a UV lamp.

However, the method of surface modification of the patterned ITO substrate in the present specification is not particularly limited, and any method oxidizing a substrate may be used.

The cathode electrode may include a metal having small work function, but is not limited thereto. Specific examples thereof may include metals such as magnesium, calcium, sodium, potassium, titanium, indium, yttrium, lithium, gadolinium, aluminum, silver, Lin and lead, or alloys thereof; or multilayer structure materials such as LiF/Al, LiO$_2$/Al, LiF/Fe, Al:Li, Al:BaF$_2$ and Al:BaF$_2$:Ba, but are not limited thereto.

The cathode electrode may be formed by being deposited inside a thermal depositor having a vacuum degree of 5×10$^{-7}$ torr or less, but the formation is not limited to this method.

The hole transfer layer and/or the electron transfer layer material play a role of efficiently transferring the electrons and the holes separated in a photoactive layer to an electrode, and the material is not particularly limited.

The hole transfer layer material may include poly(3,4-ethylenediocythiophene) doped with poly(styrenesulfonic acid) (PEDOT:PSS), molybdenum oxides (MoO$_x$); vanadium oxides (V$_2$O$_5$); nickel oxides (NiO); tungsten oxides (WO$_x$), and the like, but is not limited thereto.

The electron transfer layer material may include electron-extracting metal oxides, and may specifically include a metal complex of 8-hydroxyquinoline; a complex including Alq$_3$; a metal complex including Liq; LiF; Ca; titanium oxides (TiO$_x$); zinc oxides (ZnO); cesium carbonate (Cs$_2$CO$_3$), and the like, but is not limited thereto.

The photoactive layer may be formed by dissolving a photoactive material such as an electron donor and/or an electron acceptor in an organic solvent, and then applying the solution using a method such as spin coating, dip coating, screen printing, spray coating, doctor blade and brush painting, but the method is not limited thereto.

Hereinafter, a method for preparing the copolymer and a method for fabricating an organic solar cell including the copolymer will be described in detail with reference to the following preparation examples and examples. However, the following examples are for illustrative purposes only, and the scope of the present specification is not limited thereto.

Example 1. Synthesis of Monomer 1-j

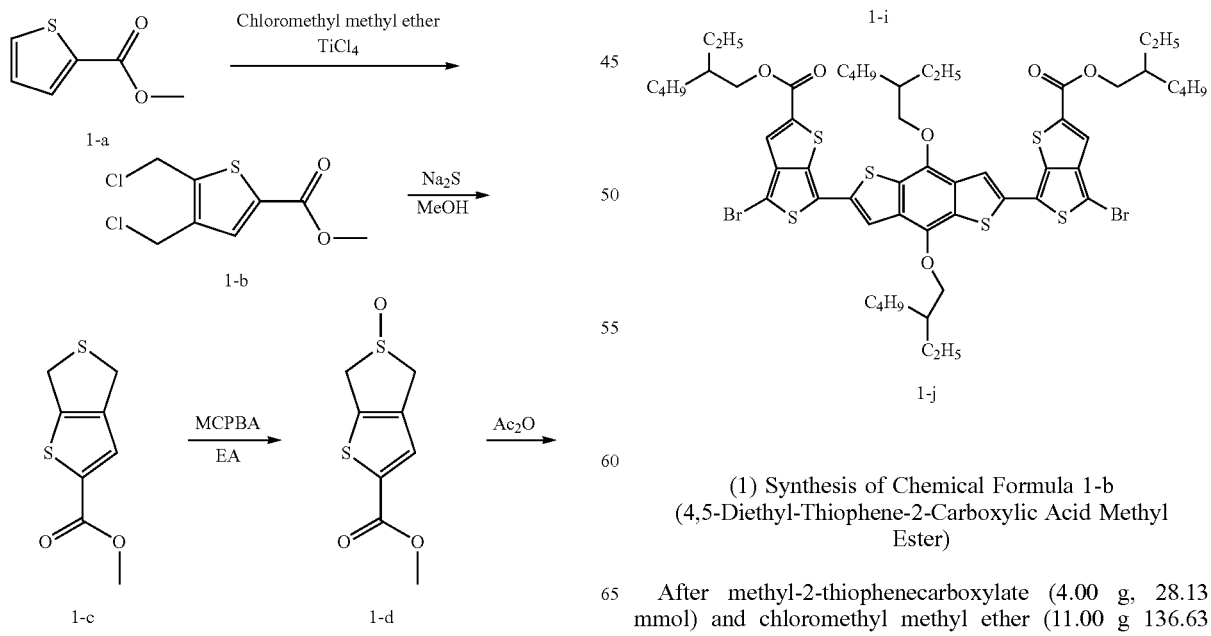

(1) Synthesis of Chemical Formula 1-b (4,5-Diethyl-Thiophene-2-Carboxylic Acid Methyl Ester)

After methyl-2-thiophenecarboxylate (4.00 g, 28.13 mmol) and chloromethyl methyl ether (11.00 g 136.63 mmol) were placed in a 100 ml flask attached with a nitrogen gas purge tube, titanium tetrachloride (TiCl$_4$) (8.00 g, 42.20 mmol) was slowly injected thereto in an ice water bath, and the mixture was reacted for 5 hours. The result was extracted using excess distilled water and methyl chloride (MC), and moisture in the organic layer was removed using anhydous sodium sulfate. The residual solvent was removed by evaporation, the result was recrystallized using hexane, and the produced crystals were vacuum filtered to obtain 5.20 g (93.2%) of white crystals. $^1$HNMR (CDCl$_3$): 3.89 (3H, s), 4.59 (2H, s), 4.78 (2H, s), 7.71 (1H, s).

FIG. 2 is a diagram showing an NMR spectrum of Chemical Formula 1-b.

(2) Synthesis of Chemical Formula 1-c (4,6-Dihydro-Thieno[3,4-b]Thiophene-2-Carboxylic Acid Methyl Ester)

Compound 1-b (5.20 g, 21.75 mmol) and 250 ml of methanol were placed in a 500 ml flask attached with a reflux condenser, and the mixture was heated in a 60° C. water bath. A solution dissolving sodium sulfide (1.87 g, 23.92 mmol) in 150 ml of methanol was slowly injected thereto over 1 hour, and the result was refluxed for 2 hours. The solid impurities were removed by vacuum filtration, the solvent was removed using an evaporator, and the remaining residue was removed using distilled water. The remaining remnants were separated using column chromatography (MC:Hex=2:1) to obtain 1.64 g of white crystals (31.23%). $^1$HNMR (CDCl$_3$): 3.87 (3H, s), 4.05-4.06 (2H, t), 4.18-4.20 (2H, t), 7.48 (1H, s)

FIG. 3 is a diagram showing an NMR spectrum of Chemical Formula 1-c.

(3) Synthesis of Chemical Formula 1-e (Thieno[3,4-b]Thiophene-2-Carboxylic Acid Methyl Ester)

After ethyl acetate, Compound 1-c (1.64 g, 8.19 mmol) and dry ice were placed in 250 ml flask equipped with a nitrogen purge tube, the mixture was cooled in a dry ice bath. Metachloroperoxobenzoic acid (MCPBA) (2.12 g, 12.28 mmol) dissolved in ethyl acetate was slowly injected thereto, and the result was reacted overnight. The solvent was removed using an evaporator, acetic anhydride was added thereto, and the result was reacted for two and a half hours. The reaction product was cooled at room temperature, then distilled, and acetic anhydride was removed. The remaining remnants were separated using column chromatography (MC:Hex=1:1) to obtain 1.31 g (80.8%) of white crystals. $^1$HNMR (CDCl$_3$): 3.91 (3H, s), 7.28-7.29 (1H, d), 7.59-7.60 (1H, d), 7.70 (1H, s)

FIG. 4 is a diagram showing an NMR spectrum of Chemical Formula 1-e.

(4) Synthesis of Chemical Formula 1-f (Thieno[3,4-b]Thiophene-2-Carboxylic Acid)

Compound 1-e (1.31 g, 6.60 mmol) dissolved in 30 ml of tetrahydrofuran (THF) and lithium hydroxide (LiOH) (0.32, 13.21 mmol) dissolved in 30 ml of distilled water were placed in a 100 ml flask attached with a reflux condenser, and the mixture was refluxed for one day in a water bath. The result was acidified using a 1 N HCl solution and vacuum filtered to obtain 1.10 g (90.5%) of dark yellow crystals. $^1$HNMR (DMSO): 7.98 (1H, s), 7.73 (2H, s)

FIG. 5 is a diagram showing an NMR spectrum of Chemical Formula 1-f.

(5) Synthesis of Chemical Formula 1-g (Theino[3,4-b]Thiophene-2-Carboxylic Acid 2-Ethyl-Hexyl Ester)

After Compound 1-f (1.10 g, 5.97 mmol) dissolved in methyl chloride (MC) was placed in a 250 ml flask equipped with a nitrogen purge tube, N,N'-dicyclohexylcarbodiimide (DCC) (1.48 g, 7.16 mmol), dimethylaminopyridine (DMAP) (0.26 g, 2.09 mmol) and 2-ethyl-1-hexanol (3.88 g, 29.85 mmol) were added thereto, and the mixture was reacted for a day. After the result was extracted using distilled water and methyl chloride (MC), moisture in the organic layer was removed using anhydous sodium sulfate. The solid impurities were removed by vacuum filtration. The residual solvent was removed by evaporation, and the result was separated by column chromatography (MC:Hex=1) to obtain 1.49 g (83.9%) of transparent oil having a slight orange color. $^1$HNMR (CDCl$_3$): 0.86-0.96 (6H, m), 1.25-1.50 (8H, m), 1.67-1.74 (1H, m), 4.19-4.27 (2H, m), 7.23-7.24 (1H, d), 7.54-7.55 (1H, d), 7.67 (1H, s)

FIG. 6 is a diagram showing an NMR spectrum of Chemical Formula 1-g.

(6) Synthesis of Chemical Formula 1-h (6-Bromo-Thieno[3,4-b]Thiophene-2-Carboxylic Acid 2-Ethyl-Hexyl Ester)

Compound 1-g (1.49 g, 5.03 mmol) dissolved in 10 ml of dimethylformamide (DMF) was placed in a 100 ml flask equipped with a nitrogen purge tube. N-bromosuccinimide (NBS) (0.89 g, 5.03 mmol) dissolved in dimethylformamide (DMF) was slowly injected thereto using a syringe, and the mixture was reacted for 5 minutes. After the result was extracted using distilled water and ethyl acetate (EA), moisture in the organic layer was removed using anhydous sodium sulfate, and the solid impurities were removed by vacuum filtration. The result was separated twice by column chromatography (MC:chloroform:hexane=1:1:3) to obtain 1.02 g (51.4%) of transparent oil having an orange color. $^1$HNMR (CDCl$_3$): 0.86-0.96 (6H, m), 1.25-1.50 (8H, m), 1.67-1.74 (1H, m), 4.20-4.27 (2H, m), 7.22 (1H, d), 7.53 (1H, d).

FIG. 7 is a diagram showing an NMR spectrum of Chemical Formula 1-h.

(7) Synthesis of Chemical Formula 1-i

A solution dissolving Compound 1-h (1.02 g, 2.72 mmol) and 2,6-bis(trimethyltin)-4,8-bis(2-ethylhexyloxy)benzo[1,2-b:4,5-b']dithiophene (0.84 g, 1.09 mmol) in 15 ml of toluene was placed in a 100 ml flask equipped with a reflux condenser together with Pd(PPh$_3$)$_4$ (0.16 g, 0.14 mmol), and the mixture was refluxed for 24 hours in an oil bath. The reaction product was cooled at room temperature, the remaining solvent was removed by evaporation, and the result was separated by column chromatography (MC:chloroform:hexane=1:1:3) to obtain 0.48 g (41.5%) of red crystals. $^1$HNMR (CDCl$_3$): 0.83-0.88 (6H, m), 0.90-1.00 (16H, m), 1.07-1.11 (6H, t), 1.36-1.54 (22H, m), 1.62-1.67 (4H, m), 1.72-1.77 (4H, m), 1.84-1.87 (2H, m), 4.20-4.22 (4H, d), 4.27-4.29 (4H, m), 7.22 (2H, s), 7.57 (2H, s), 8.05 (2H, s).

FIG. 8 is a diagram showing an NMR spectrum of Chemical Formula 1-i.

(8) Synthesis of Chemical Formula 1-j 15 ml of chloroform (CHCl$_3$) dissolving Compound 1-i (0.48 g, 0.46 mmol) was placed in a 100 ml flask equipped with a nitrogen purge tube. N-bromosuccinimide (NBS) (0.18, 1.02 mmol) dissolved in chloroform (CHCl$_3$) was slowly injected thereto using a syringe, and the mixture was reacted for 4 hours in a dark place. The result was extracted using distilled water and methyl chloride (MC), moisture in the organic layer was removed using anhydous sodium sulfate, and the solid impurities were removed by vacuum filtration. The result was separated by column chromatography (MC:Hex=1:2) to obtain 0.36 g (65.7%) of dark red crystals. $^1$HNMR (CDCl$_3$): 0.83-0.88 (6H, m), 0.90-1.00 (16H, m), 1.07-1.11 (6H, t), 1.36-1.54 (22H, m), 1.62-1.67 (4H, m), 1.72-1.77 (4H, m), 1.84-1.87 (2H, m), 4.20-4.22 (4H, d), 4.27-4.29 (4H, m), 7.50 (2H, s), 8.03 (2H, s).

FIG. 9 is a diagram showing an NMR spectrum of Chemical Formula 1-j.

Example 2. Synthesis of Monomer 2-b

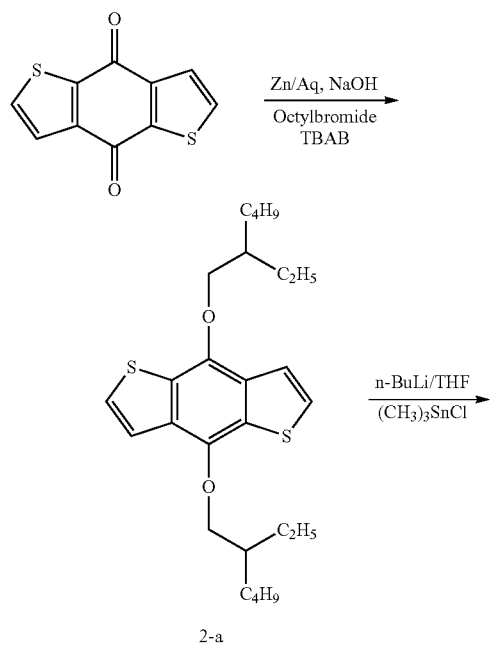

(1) Synthesis of Chemical Formula 2-a

After 4,8-dehydrobenzo[1,2-b:4,5-b']dithiophene-4,8-dione (8.0 g, 36.2 mmol) and zinc powder (Zn powder) (5.2 g, 79.6 mmol) were placed in 60 ml of deionized (DI) water (H$_2$O), the mixture was stirred, and sodium hydroxide (NaOH, 24 g) was added thereto, and the result was refluxed for 1 hour while stirring. During the reaction, the color of the solution changed from yellow to orange through red. 2-Ethylhexylbromide (21.0 g, 108.9 mmol) and tetrabutylammonium bromide (as catalyst) were added to this solution, and the result was stirred/refluxed for 2 hours. When the color of the solution was red or deep red, zinc powder was additionally added, and the result was stirred/refluxed for 6 hours. This solution was poured into cold water, extracted twice using diethyl ether, and then residual water was removed using magnesium sulfate (MgSO$_4$). The remaining solution was vacuumed to remove the solvent, and a colorless liquid was obtained through silica column (eluent; pet. ether: MC=9:1).

Yield: 64.9%

(2) Synthesis of Chemical Formula 2-b

Compound 2-a (10.3 g, 23.1 mmol) was placed and dissolved in 50 ml of tetrahydrofuran (THF), and the temperature was lowered to −78° C. 1.6 M n-butyllithium (n-BuLi) in hexane (31.7 ml, 50.8 mmol) was slowly added thereto at this temperature, and the result was stirred for 30 minutes. After that, the temperature was raised to 0° C., and the result was stirred for 1 hour under this condition. Then, the temperature was lowered again to −78° C., and 1 M trimethyltinchloride in tetrahydrofuran (THF) (53.1 ml, 53.1 mmol) was added thereto at once, the temperature was raised to room temperature, and the result was stirred for 12 hours. This solution was poured into ice, extracted twice using diethyl ether, washed twice with water, and residual water was removed using magnesium sulfate (MgSO$_4$). The remaining solution was vacuumed to remove the solvent, and the result was recrystallized with ethanol to obtain a colorless crystalline solid.

Yield: 71.4%

FIG. 10 is a diagram showing an NMR spectrum of Chemical Formula 2-b.

FIG. 11 is a diagram showing an MS spectrum of Chemical Formula 2-b.

Example 3. Synthesis of Monomer 3-b

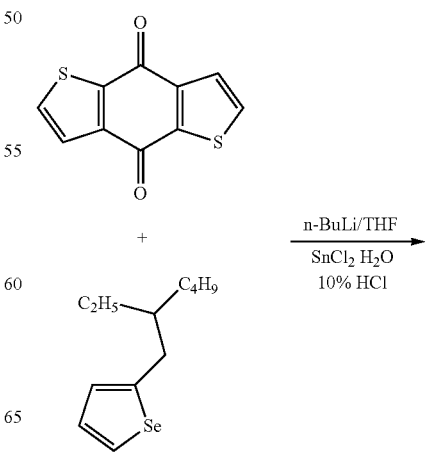

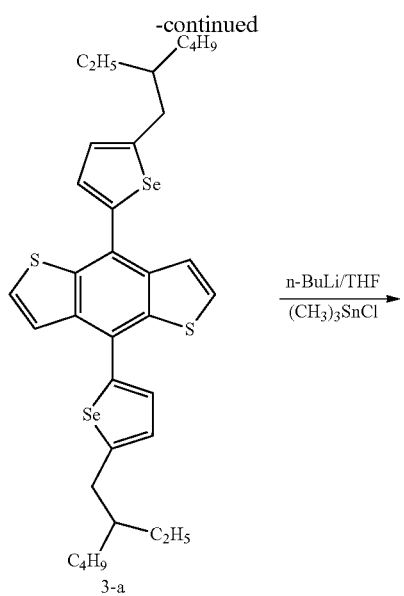

3-a

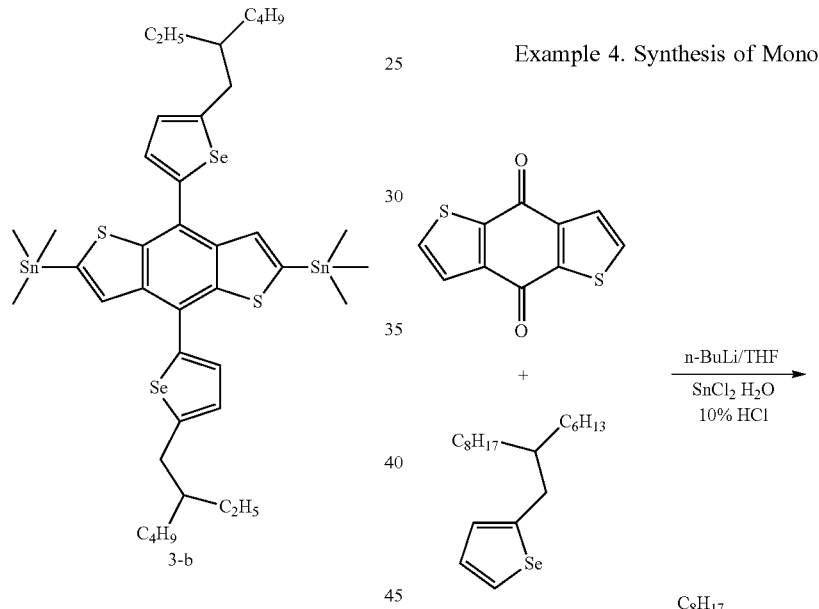

3-b (1) Synthesis of Chemical Formula 3-a 2-(2-Ethylhexyl)selenophene (5.0 g, 23.2 mmol) was placed in 300 ml of tetrahydrofuran (THF), and the temperature was lowered to −78° C. 2.5 M n-butyllithium (n-BuLi) in hexane (11.1 ml, 27.9 mmol) was slowly added thereto at this temperature, and the result was stirred for 1 hour. After that, the temperature was raised to 0° C., and the result was stirred for 1 hour under this condition. 4,8-dehydrobenzo[1,2-b:4,5-b']dithiophene-4,8-dione (2.1 g, 9.28 mmol) was added thereto at once, and the result was stirred for 6 hours at 50° C. After this solution was cooled to room temperature, tin(II) chloride dihydrate (SnCl$_2$.2H$_2$O) (15 g) and 10% HCl (30 ml) were additionally added thereto, and the result was further stirred for 3 hours. Ice was poured into this solution, the result was extracted with diethyl ether, and residual water was removed using magnesium sulfate (MgSO$_4$). The remaining solution was vacuumed to remove the solvent, and a high-density yellow liquid was obtained through a silica column (eluent; petroleum).

Yield: 70%

(2) Synthesis of Chemical Formula 3-b

Compound 3-a (2.0 g, 3.24 mmol) was placed and dissolved in 100 ml of tetrahydrofuran (THF), and the temperature was lowered to 0° C. 1.6 M n-butyllithium (n-BuLi) in hexane (7.1 ml, 11.3 mmol) was slowly added thereto at this temperature, and the result was stirred for 1 hour at room temperature. 1 M trimethyltinchloride in THF (8.10 ml, 8.10 mmol) was added to this solution at once, and the result was stirred for 2 hours. Water was poured into this solution, the result was extracted with hexane, and then residual water was removed using magnesium sulfate (MgSO$_4$). The remaining solution was vacuumed to remove the solvent, and recrystallized with ethanol to obtain a light yellow crystalline solid.

Yield: 85%

FIG. 12 is a diagram showing an NMR spectrum of Chemical Formula 3-a.

FIG. 13 is a diagram showing an NMR spectrum of Chemical Formula 3-b.

Example 4. Synthesis of Monomer 4-b

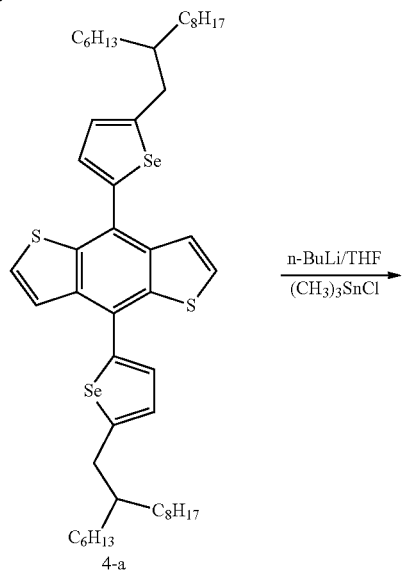

4-a

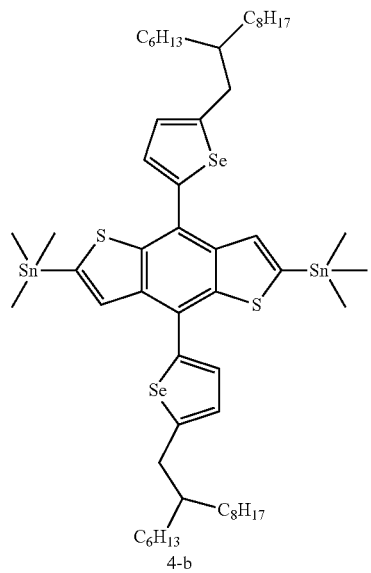

Monomer 4-b was prepared in the same manner as in Example 3 except that 2-(2-hexyldecyl)selenophene was used instead of 2-(2-ethylhexyl)selenophene in Example 3.

Example 5. Synthesis of Monomer 5-e

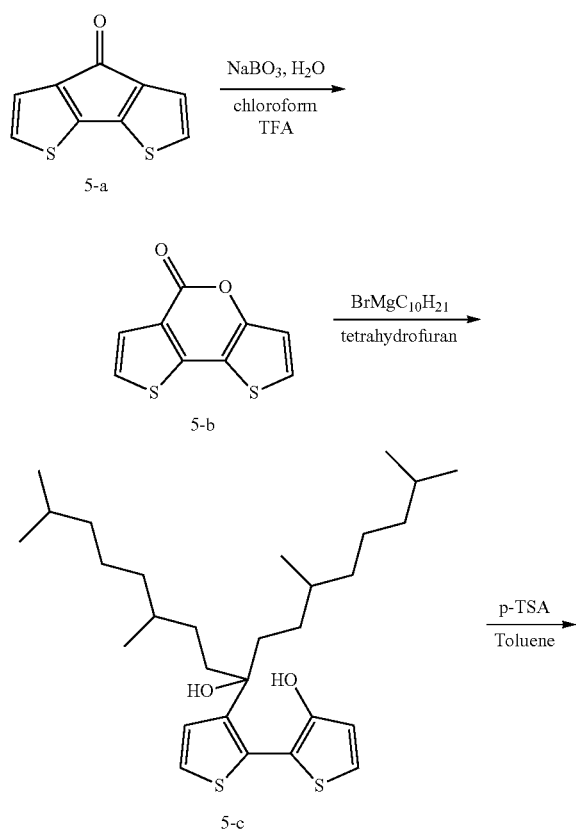

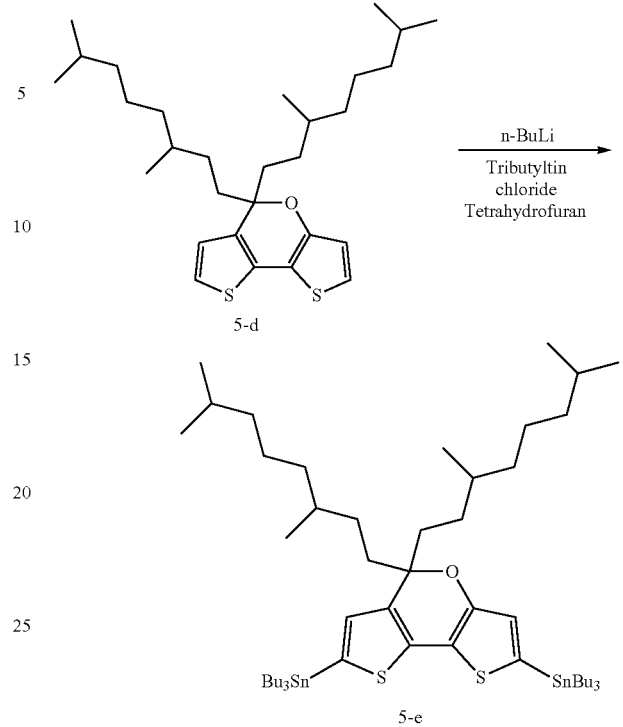

(1) Synthesis of Chemical Formula 5-b

Compound 5-a (6.0 g, 31.2 mmol) was dissolved in 50 ml chloroform(CF): 50 ml trifluoroacetic acid (TFA). Sodium perborate monohydrate (7.39 g, 72.8 mmol) was added thereto at once, and the result was stirred for 1 hour at room temperature. This solution was poured into water, and then extracted with chloroform. The solvent was removed under vacuum, and a white solid was obtained through a silica column (eluent: Hx/MC=1/1).

Yield: 35%

(2) Synthesis of Chemical Formula 5-c

Compound 5-b (2.4 g, 11.4 mmol) was dissolved in 60 ml of tetrahydrofuran (THF) under nitrogen. 25.4 ml of 3,7-dimethyloctylmagnesium bromide (1 M solution in diethyl ether) was slowly injected thereto at −25° C. The result was stirred for 10 hour while raising the temperature to room temperature, and the reaction was stopped while adding 50 ml of water. The result was extracted with ethyl acetate (EA), and residual water was removed using magnesium sulfate ($MgSO_4$). A light yellow liquid was obtained through a silica column.

Yield: 93%

(3) Synthesis of Chemical Formula 5-d

Compound 5-c (4.5 g, 12.0 mmol) was dissolved in 100 ml of toluene under nitrogen. 300 mg of sodium p-toluene-sulfonic acid monohydrate was added thereto, and the result was reacted for 3 hours at 120° C.

The reaction solution was poured into water, and was extracted by adding toluene thereto. The result was dried using magnesium sulfate ($MgSO_4$), and then the solvent was removed under vacuum. A yellow liquid was obtained through a silica column (eluent: Hx).

Yield: 95%

(4) Synthesis of Chemical Formula 5-e

Compound 5-d (0.58 g, 1.2 mmol) was dissolved in 20 ml of tetrahydrofuran (THF) under nitrogen. n-Butyl lithium (1.7 ml, 1.6 M solution in hexane) was slowly added thereto at −78° C., the result was stirred for 30 minutes, and then stirred for 2 hours at room temperature. The temperature was lowered to −78° C. again, and 0.92 ml of a tributyltin chloride solution was added thereto. While raising the temperature, the result was stirred for 10 hours at room temperature. The result was poured into water, and extracted with hexane. The solvent was removed under vacuum, and a brown liquid was obtained through a silica column (eluent: Hx, 10% triethylamine).

Yield: 97%

FIG. 14 is a diagram showing an NMR spectrum of Chemical Formula 5-e.

Example 6. Synthesis of Monomer 6-b

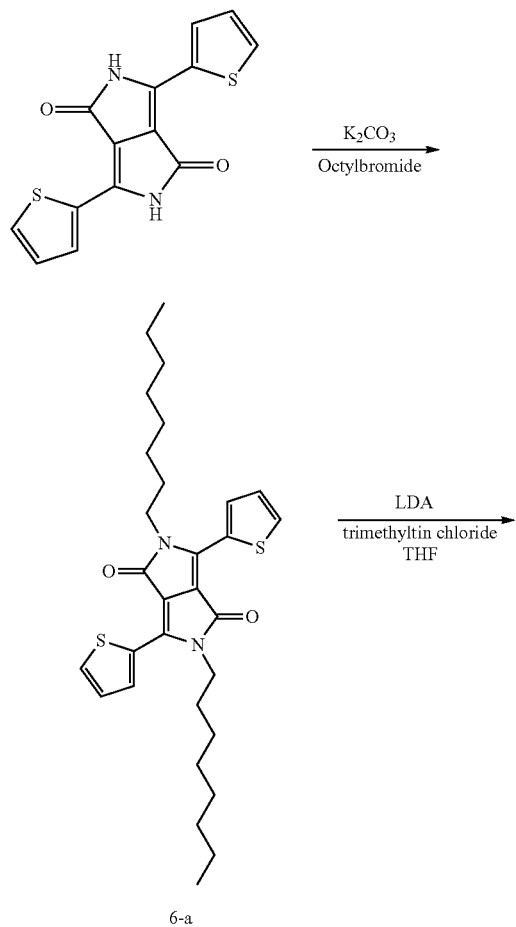

6-a

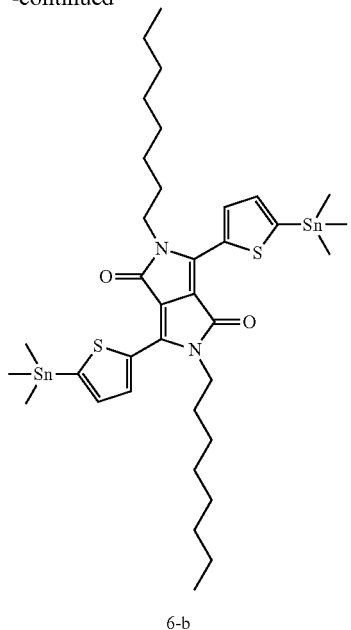

6-b 3,6-Dithiophen-2-yl-2,5-dihydropyrrolo[3,4-c]pyrrole-1,4-dione (13.0 g, 43.3 mmol) and potassium carbonate ($K_2CO_3$, 24.0 g) were placed and well dissolved in 350 ml of dimethylformamide (DMF) by heating at 145° C. Octyl bromide (38.6 g, 200 mmol) was added to this solution at once using a syringe. After the result was stirred for 15 hours or longer at 145° C., the temperature was lowered to room temperature. The result was poured into 500 ml or more of cold water, stirred, and then filtered while washing several times with water and alcohol. After drying, a dark purple solid powder was obtained through a silica column (eluent; hexane:methylene chloride=1:10). (Yield: 87.4%)

To a 2.0 M lithium diisopropylamide solution (LDA, 6 ml, 12.0 mmol) in a 250 ml flask, a compound of Chemical Formula 6-a (3 g, 5.7166 mmol) dissolved in 100 ml of tetrahydrofuran (THF) was slowly added using a syringe at −20° C., and the mixture was stirred for 1 hour. 1 M trimethyltin chloride (($CH_3)_3SnCl$, 13.14 ml, 13.14 mmol) was added thereto, and the result was stirred for 12 hours while raising the temperature to room temperature. This solution was extracted with water and chloroform (CF), washed with water, and residual water was removed using magnesium sulfate ($MgSO_4$). The remaining solution was vacuumed to remove the solvent, and a compound 6-b was obtained through recrystallization with MC/EtOH. (Yield 42%) FIG. 15 is a diagram showing an NMR spectrum of Chemical Formula 6-b.

Example 7. Synthesis of Monomer 7-a

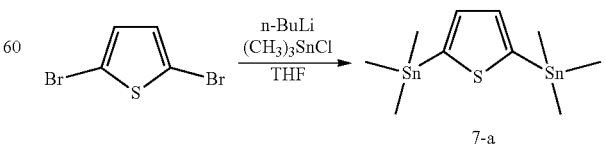

7-a 2,5-Dibromothiophene (9.68 g, 40.0 mmol) was placed and dissolved in 200 ml of tetrahydrofuran (THF), and the temperature was lowered to −78° C. 1.6 M n-butyllithium (n-BuLi) in hexane (55 ml, 88 mmol) was slowly added thereto at this temperature, and the result was stirred for 1 hour. After that, 1 M trimethyltin chloride in THF (100 ml, 100 mmol) was added thereto at once, the temperature was raised to room temperature, and then the result was stirred for 12 hours. This solution was poured into ice, the result was extracted three times with diethyl ether, washed three times with water, and residual water was removed using magnesium sulfate (MgSO$_4$). The remaining solution was vacuumed to remove the solvent, and was recrystallized with methanol to obtain a white solid.

Yield: 73.1%

FIG. 16 is a diagram showing an NMR spectrum of Chemical Formula 7-a.

Example 8. Synthesis of Monomer 8-b

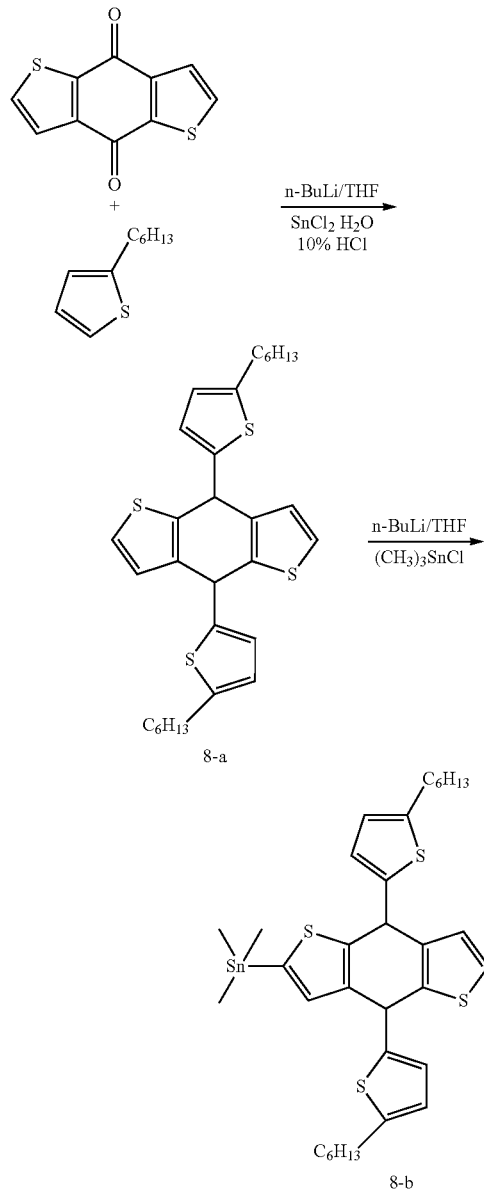

(1) Synthesis of Chemical Formula 8-a

2-Hexylthiophene (10.0 g, 59.4 mmol) was placed and dissolved in 500 ml of tetrahydrofuran (THF), and the temperature was lowered to −78° C. 2.5 M n-butyllithium (n-BuLi) in hexane (24.0 ml, 59.4 mmol) was slowly added thereto at this temperature, and the result was stirred for 30 minutes. After that, the temperature was raised to 0° C., the result was stirred for 1 hour under this condition, then 4,8-dehydrobenzo[1,2-b:4,5-b']dithiophene-4,8-dione (3.3 g, 14.8 mmol) was added thereto at once, and the result was stirred for 3 hours at 50° C. This solution was cooled to room temperature, tin(II) chloride dihydrate (SnCl$_2$.2H$_2$O) (26 g) and 10% HCl (56 ml) were added thereto, and the result was further stirred for 3 hours. Ice was poured into this solution, and the result was extracted twice with diethyl ether, washed twice with water, and residual water was removed using magnesium sulfate (MgSO$_4$). The remaining solution was vacuumed to remove the solvent, and a high-density yellow liquid was obtained through a silica column (eluent; petroleum).

Yield: 64%

(2) Synthesis of Chemical Formula 8-b 8-a (3.9 g, 7.43 mmol) was placed and dissolved in 100 ml of tetrahydrofuran (THF), and the temperature was lowered to 0° C. 1.6 M n-butyllithium (n-BuLi) in hexane (10.4 ml, 16.7 mmol) was slowly added thereto at this temperature, and the result was stirred for 1 hour at room temperature. 1 M trimethyltinchloride in tetrahydrofuran (THF) (22.7 ml, 22.7 mmol) was added to this solution at once, and the result was stirred for 2 hours. Water was poured into this solution, and the result was extracted twice with diethyl ether, washed twice with water, and residual water was removed using magnesium sulfate (MgSO$_4$). The remaining solution was vacuumed to remove the solvent, and recrystallized with ethanol to obtain a light yellow crystalline solid.

Yield: 87%

FIG. 17 is a diagram showing an NMR spectrum of Chemical Formula 8-b.

FIG. 18 is a diagram showing an MS spectrum of Chemical Formula 8-b.

Example 9. Synthesis of Monomer 9-b

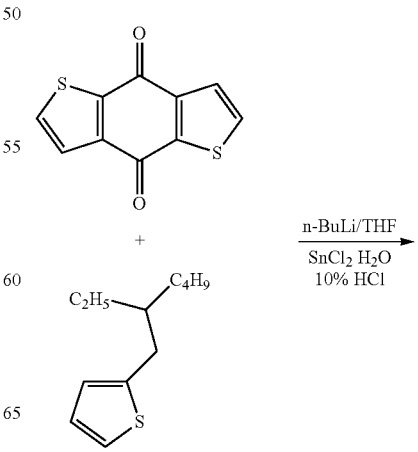

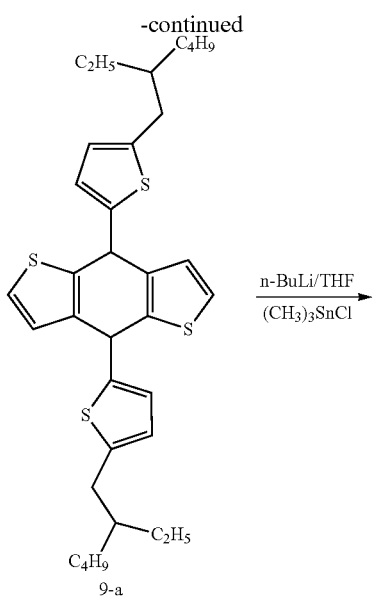

9-a

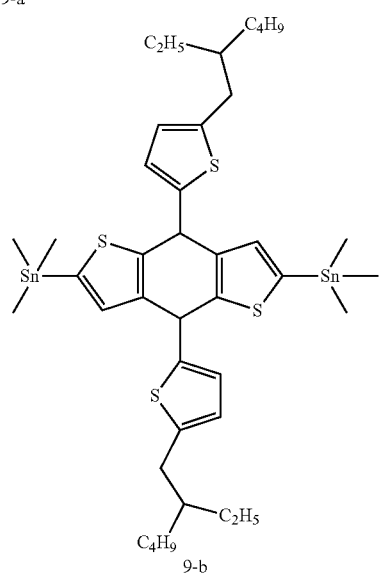

9-b (1) Synthesis of Chemical Formula 9-a 2-(2-Ethylhexyl)thiophene (10.0 g, 59.4 mmol) was placed and dissolved in 500 ml of tetrahydrofuran (THF), and the temperature was lowered to −78° C. 2.5 M n-butyllithium (n-BuLi) in hexane (24.0 ml, 59.4 mmol) was slowly added thereto at this temperature, and the result was stirred for 30 minutes. After that, the temperature was raised to 0° C., the result was stirred for 1 hour under this condition, then 4,8-dehydrobenzo[1,2-b:4,5-b']dithiophene-4,8-dione (3.3 g, 14.8 mmol) was added thereto at once, and the result was stirred for 3 hours at 50° C. This solution was cooled to room temperature, tin(II) chloride dihydrate ($SnCl_2 \cdot 2H_2O$) (26 g) and 10% HCl (56 ml) were added thereto, and the result was further stirred for 3 hours. Ice was poured into this solution, and the result was extracted twice with diethyl ether, washed twice with water, and residual water was removed using magnesium sulfate ($MgSO_4$). The remaining solution was vacuumed to remove the solvent, and a high-density yellow liquid was obtained through a silica column (eluent; petroleum).

Yield: 64%

(2) Synthesis of Chemical Formula 9-b

Compound 9-a (3.9 g, 7.59 mmol) was placed and dissolved in 100 ml of tetrahydrofuran (THF), and the temperature was lowered to 0° C. 1.6 M n-butyllithium (n-BuLi) in hexane (10.4 ml, 16.7 mmol) was slowly added thereto at this temperature, and the result was stirred for 1 hour at room temperature. 1 M trimethyltinchloride in tetrahydrofuran (THF) (22.7 ml, 22.7 mmol) was added to this solution at once, and the result was stirred for 2 hours. Water was poured into this solution, and the result was extracted twice with diethyl ether, washed twice with water, and residual water was removed using magnesium sulfate ($MgSO_4$). The remaining solution was vacuumed to remove the solvent, and recrystallized with ethanol to obtain a light yellow crystalline solid.

Yield: 87%

FIG. 19 is a diagram showing an NMR spectrum of Chemical Formula 9-b.

Example 10. Synthesis of Monomer 10-a

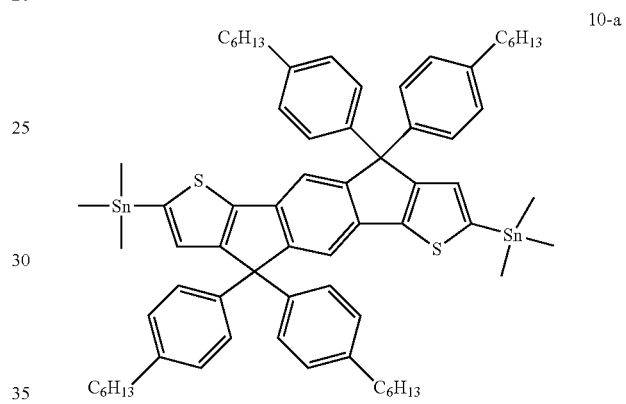

The monomer was prepared in the same manner as the synthesis method of Wen Wen, z Lei Ying, z Ben B. Y. Hsu, Yuan Zhang, Thuc-Quyen Nguyen and Guillermo C. Bazan, Chem. Commun., 2013, 49, 7192-7194.

FIG. 20 is a diagram showing an NMR spectrum of Chemical Formula 10-a.

Example 11. Synthesis of Monomer 11-a

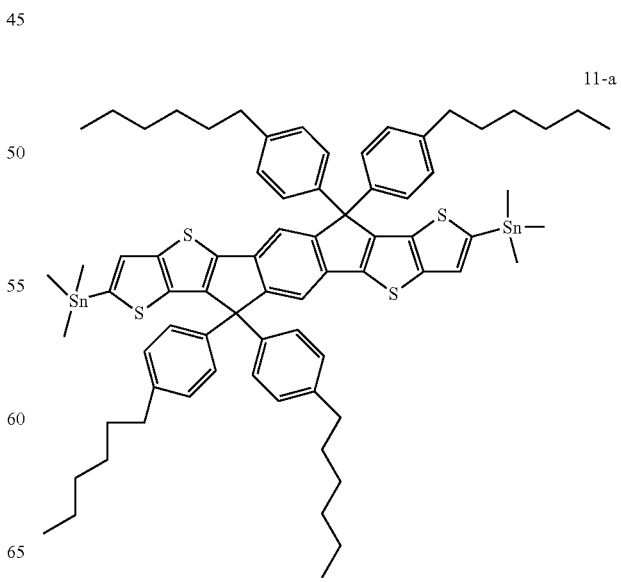

The monomer was prepared in the same manner as the synthesis method of Yun-Xiang Xu, Chu-Chen Chueh, Hin-Lap Yip, Fei-Zhi Ding, Yong-XiLi, Chang-Zhi Li, Xiaosong Li Wen-Chang Chen, and Alex K.-Y. Jen, Adv. Mater. 2012, 24, 6356-6361.

FIG. 21 is a diagram showing an MS spectrum of Chemical Formula 11-a.

FIG. 22 is a diagram showing an NMR spectrum of Chemical Formula 11-a.

Example 12. Synthesis of Monomer 12-a

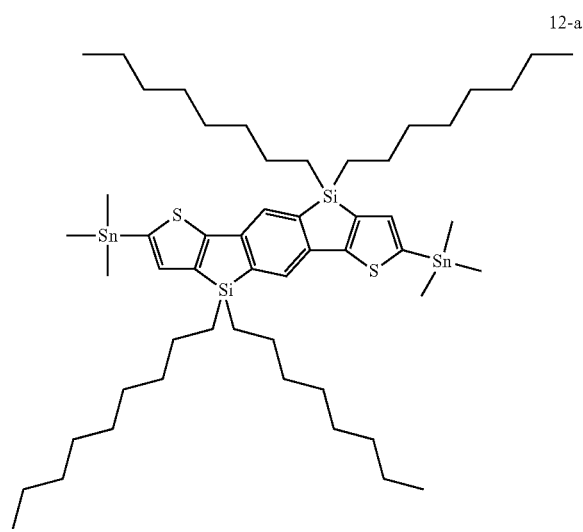 [SMILES: CCCCCCCCC[Si]1(CCCCCCCC)c2cc3c(cc2-c2s[c]([Sn]([CH3])([CH3])[CH3])cc21)[Si](CCCCCCCC)(CCCCCCCC)c1c[c]([Sn]([CH3])([CH3])[CH3])sc1-3]

12-a

The monomer was prepared in the same manner as the synthesis method of Bob C. Schroeder, Zhenggang Huang, Raja Shahid Ashraf, * Jeremy Smith, Pasquale D' Angelo, Scott E. Watkins, Thomas D. Anthopoulos, James R. Durrant, and Iain McCulloch, Adv. Funct. Mater. 2012, 22, 1663-1670.

FIG. 23 is a diagram showing an NMR spectrum of Chemical Formula 12-a.

Example 13. Synthesis of Monomer 13-b

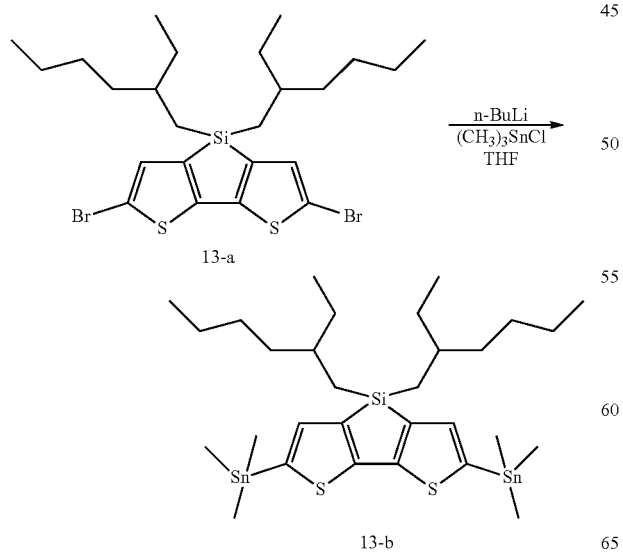

4,4'-Bis(2-ethyl-hexyl)-5,5'-dibromodithieno[3,2-b:2',3'-b']silole (5.0 g, 8.67 mmol) was dissolved in 50 ml of tetrahydrofuran (THF), and the temperature was lowered to −78° C. n-BuLi (8.67 ml, 2.5 M in hexane) was added thereto. After 30 minutes, $(CH_3)_3SnCl$ (3.49 ml, 1M in hexane) was added thereto, and the result was stirred for 18 hours. The result was extracted with water and diethyl ether, and residual water in the organic layer was removed using magnesium sulfate $(MgSO_4)$. The solvent was removed and the result was dried in an oven.

Yield: 96.1%

FIG. 24 is a diagram showing an NMR spectrum of Chemical Formula 13-b.

Example 14. Synthesis of Monomer 14-d

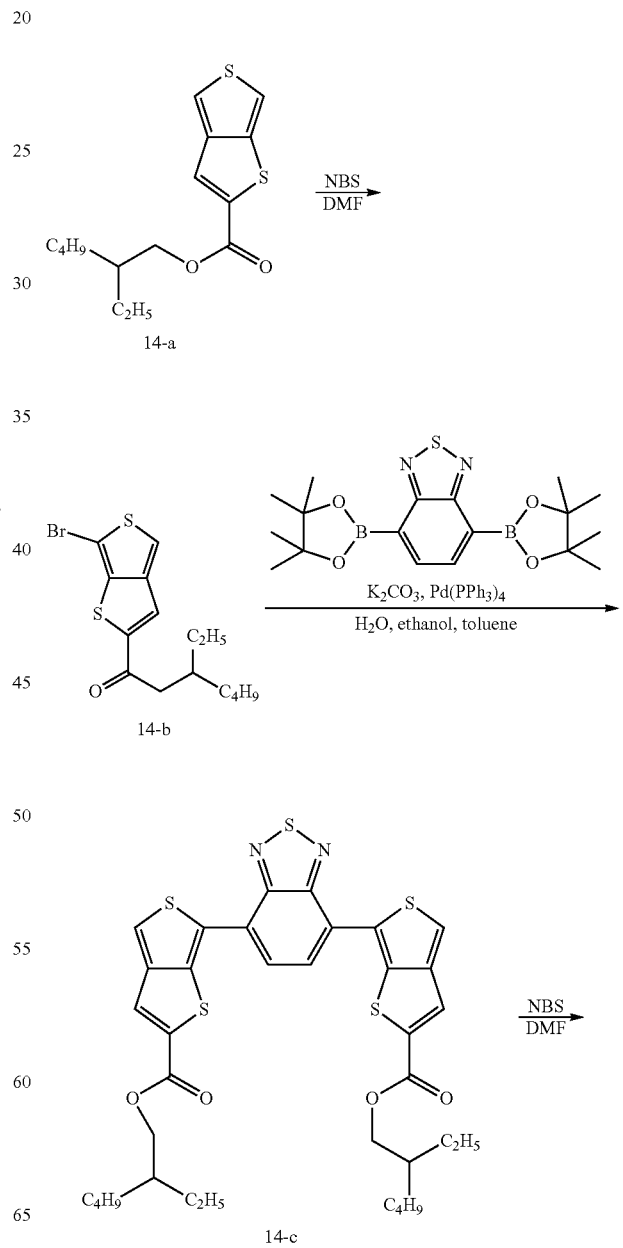

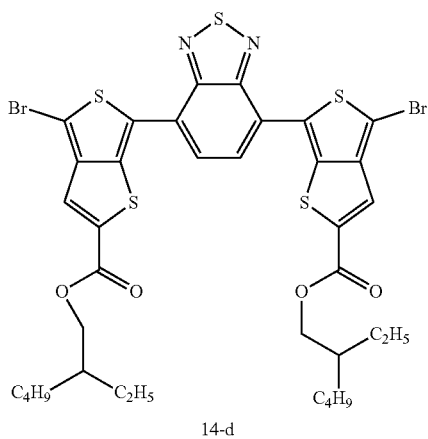

14-d

(1) Synthesis of Chemical Formula 14-b

Thieno[3,4-b]thiophene-2-carboxylic acid 2-ethyl-hexyl ester (1.49 g, 5.03 mmol) was placed in 10 mL of dimethylformamide (DMF), N-bromosuccinimide (NBS, 0.90 g, 5.03 mmol) was added dropwise thereto, and then the result was stirred for 30 minutes. Deionized (DI) water was added to this solution, and the result was extracted many times with ethyl acetate. The solvent was removed under vacuum, and the result was dried using anhydrous sodium sulfate. From the residue, oil of Chemical Formula 14-b (0.79 g, 41.8%) was obtained through silica column chromatography (methylene chloride and hexane (1:2)). $^1$H NMR (CDCl$_3$, 400 MHz): 7.53 (1H, s), 7.22 (1H, s), 4.20-4.27 (2H, m), 1.67-1.74 (1H, m), 1.25-1.50 (8H, m), 0.86-0.96 (6H, m).

(2) Synthesis of Chemical Formula 14-c 2,1,3-Benzothiadiazole-4,5-bis(boronic acid pinacol ester (0.33 g, 0.84 mmol), Pd(PPh$_3$)$_4$ (0.05 g, 0.04 mmol) and the compound of Chemical Formula 14-b (0.79 g, 2.10 mmol) were placed in 20 mL of toluene, an aqueous potassium carbonate solution (10 ml) and 10 mL of ethanol, and the mixture was refluxed and stirred under a nitrogen atmosphere at 110° C. overnight. The mixture was cooled to room temperature, the solvent was removed under vacuum, and the result was dried with anhydrous sodium sulfate. From the residue, a red solid of Chemical Formula 14-c (0.40 g, 65.7%) was obtained through silica column chromatography (methylene chloride and hexane (1:2)). $^1$H NMR (CDCl$_3$, 400 MHz): 8.11 (2H, s), 8.03 (2H, s), 7.52 (2H, s), 4.27-4.28 (4H, m), 1.64-1.75 (2H, m), 1.30-1.48 (16H, m), 0.88-0.96 (12H, m).

(3) Synthesis of Chemical Formula 14-d

Chemical Formula 14-c (0.40 g, 0.55 mmol) and 10 ml of chloroform were placed in a round flask, N-bromosuccinimide (NBS, 0.22 g, 1.21 mmol) was added dropwise thereto, and the mixture was stirred for 10 minutes. Deionized (DI) water was added to this solution, and the result was extracted many times with ethyl acetate. The solvent was removed under vacuum, and the result was dried using anhydrous sodium sulfate. From the residue, a blue solid of Chemical Formula 14-d (0.37 g, 76.2%) was obtained through silica column chromatography (methylene chloride and hexane (1:1)). $^1$H NMR (CDCl$_3$, 400 MHz): 7.94 (1H, s), 7.68 (1H, s), 4.23-4.31 (4H, m), 1.64-1.75 (2H, m), 1.30-1.48 (16H, m), 0.88-0.96 (12H, m). GC/MS (m/z): calcd for C$_{38}$H$_{38}$Br$_2$N$_2$O$_4$S$_5$, 881.98; found, 882.20 [M]$^+$.

Example 15. Synthesis of Monomer 15-d

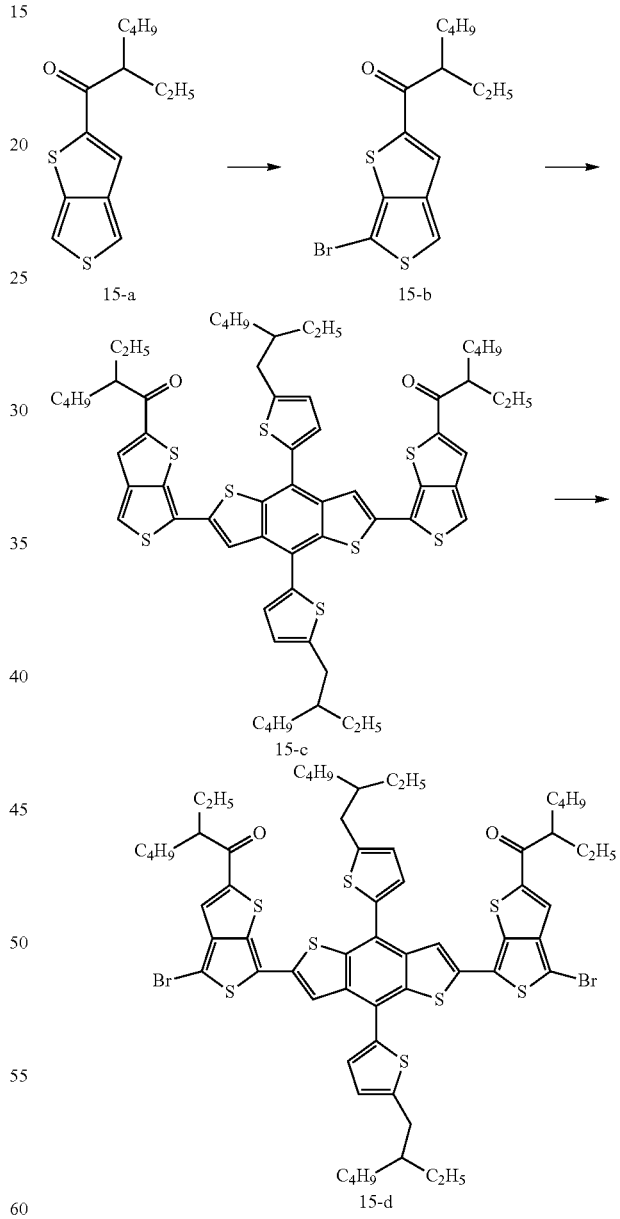

Chemical Formula 15-d was prepared in the same manner as in Example 1 except that Chemical Formula 15-a was used instead of Chemical Formula 1-g, and Chemical Formula 9-a of Example 9 was used instead of 2,6-bis(trimethyltin)-4,8-bis(2-ethylhexyloxy)benzo[1,2-b: 4,5-b']dithiophene in Example 1.

Example 16. Synthesis of Monomer 16-b
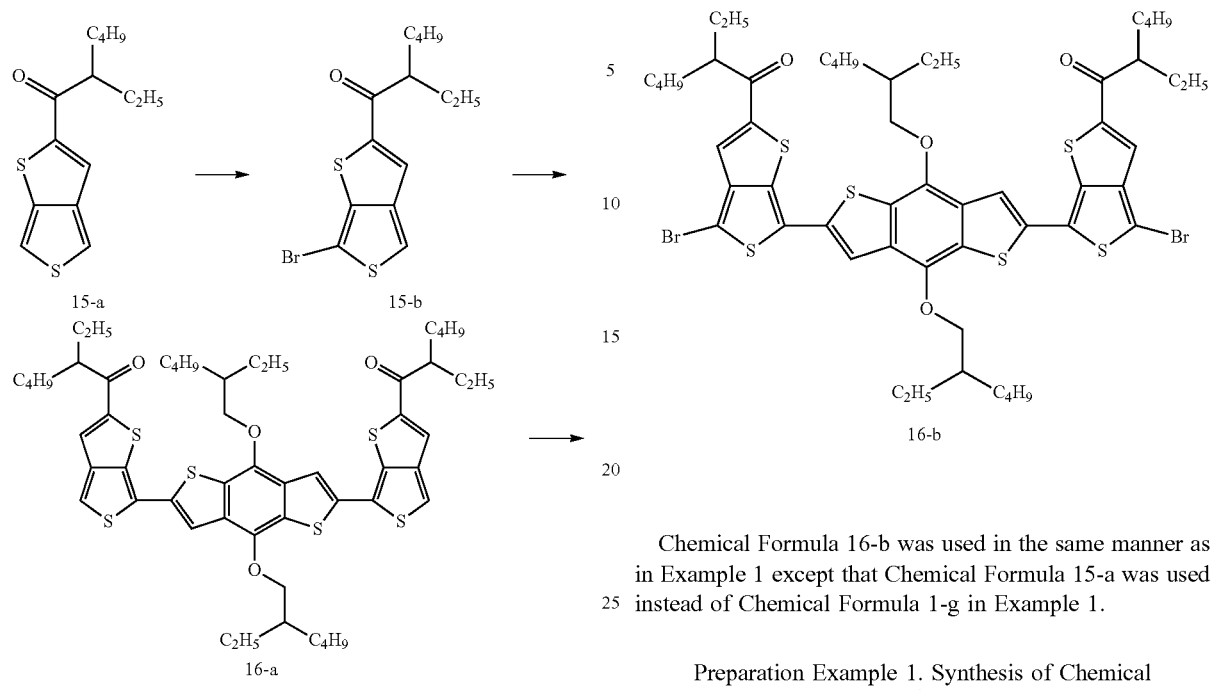
Chemical Formula 16-b was used in the same manner as in Example 1 except that Chemical Formula 15-a was used instead of Chemical Formula 1-g in Example 1.
Preparation Example 1. Synthesis of Chemical Formula 1-1-1
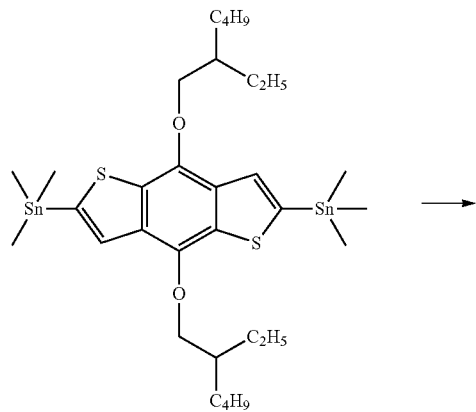

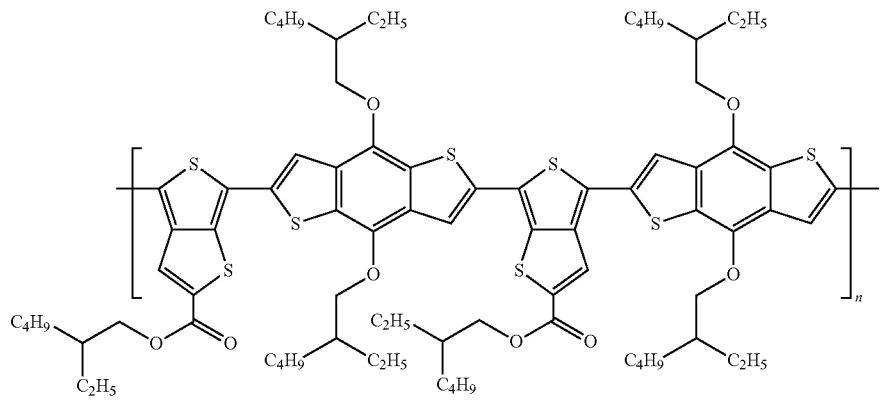

18 ml of chlorobenzene, 1-j (0.700 g, 0.5866 mmol), 2-b (0.2641 g, 0.5866 mmol), tris(dibenzylideneacetone)dipalladium(0) (Pd$_2$(dba)$_3$, 10 mg), and tri-(o-tolyl)phosphine (28 mg) were placed in a microwave reactor vial, and the mixture was reacted for 1 hour under a condition of 170° C. The mixture was cooled to room temperature, poured into methanol, and solids were filtered. The filtered solids were Soxhlet extracted with acetone, hexane, methylene chloride and chloroform, and solids were filtered by precipating the chloroform part again in methanol.

Preparation Example 2. Synthesis of Chemical Formula 1-1-2

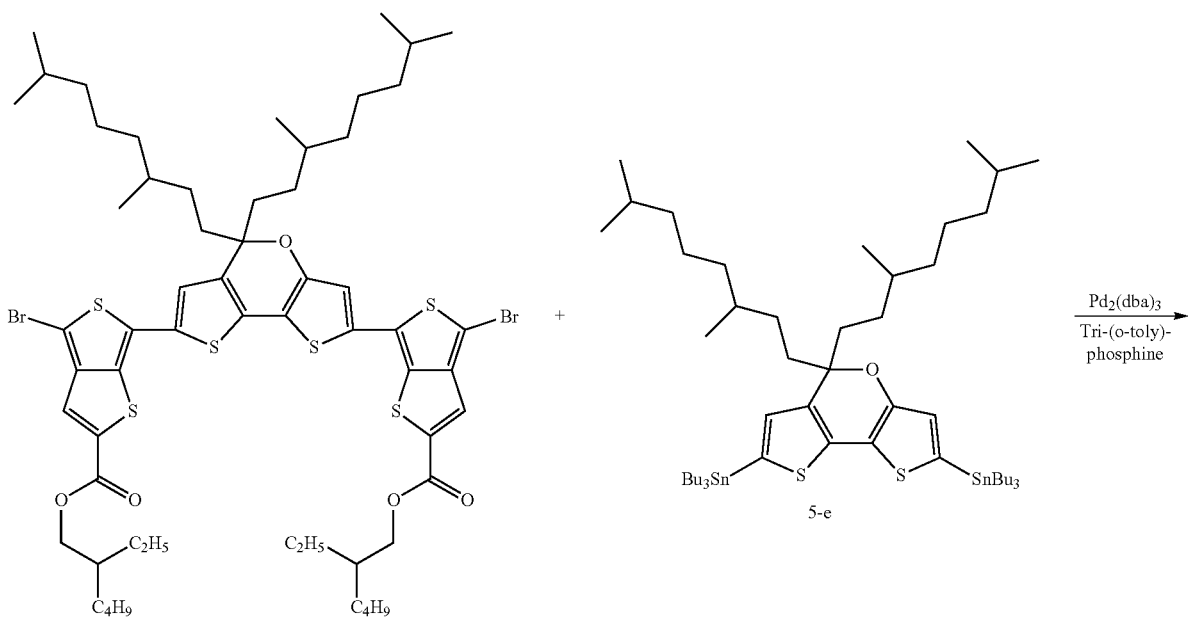

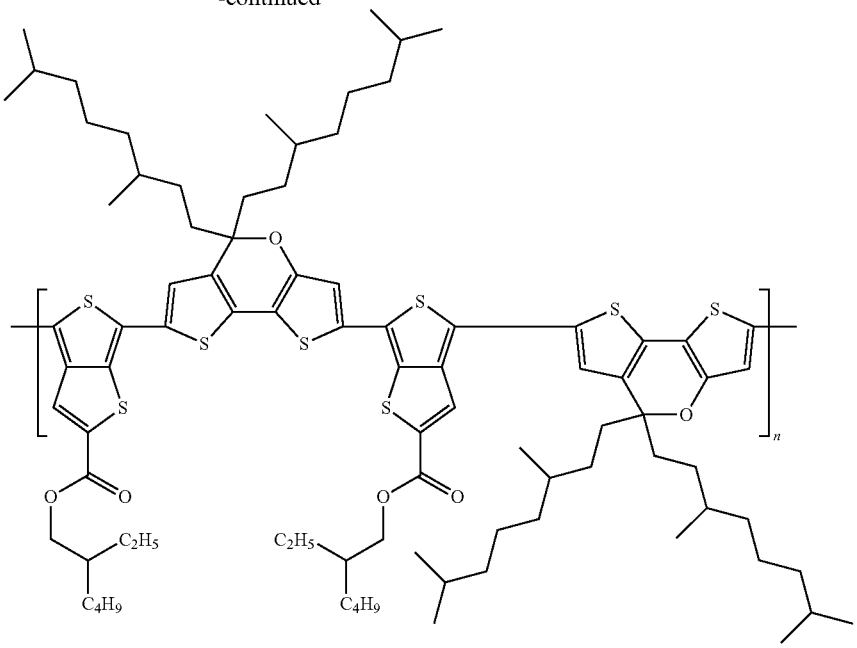

18 ml of chlorobenzene, a compound (0.700 g, 0.5731 mmol) prepared in the same manner as in Example 1 except that 5,5-bis(3,7-dimethyloctyl)-5H-dithieno[3,2-b:2',3'-d]pyran-2,7-diyl)bis(trimethylstannane) was used instead of 2,6-bis(trimethyltin)-4,8-bis(2-ethylhexyloxy)benzo[1,2-b:4,5-b']dithiophene in the (7) preparation method of Chemical Formula 1-i in Example 1, the compound of Chemical Formula 5-e (0.6033 g, 0.0.5731 mmol), tris(dibenzylideneacetone)dipalladium(0) (Pd$_2$(dba)$_3$, 10 mg), and tri-(o-tolyl) phosphine (28 mg) were placed in a microwave reactor vial, and the mixture was reacted for 1 hour under a condition of 170° C. The mixture was cooled to room temperature, poured into methanol, and solids were filtered. The filtered solids were Soxhlet extracted with acetone, hexane, methylene chloride and chloroform, and solids were filtered by precipating the chloroform part again in methanol.

Yield: 47%
Number Average Molecular Weight: 33,200 g/mol
PDI: 1.8

Preparation Example 3. Synthesis of Chemical Formula 1-1-3

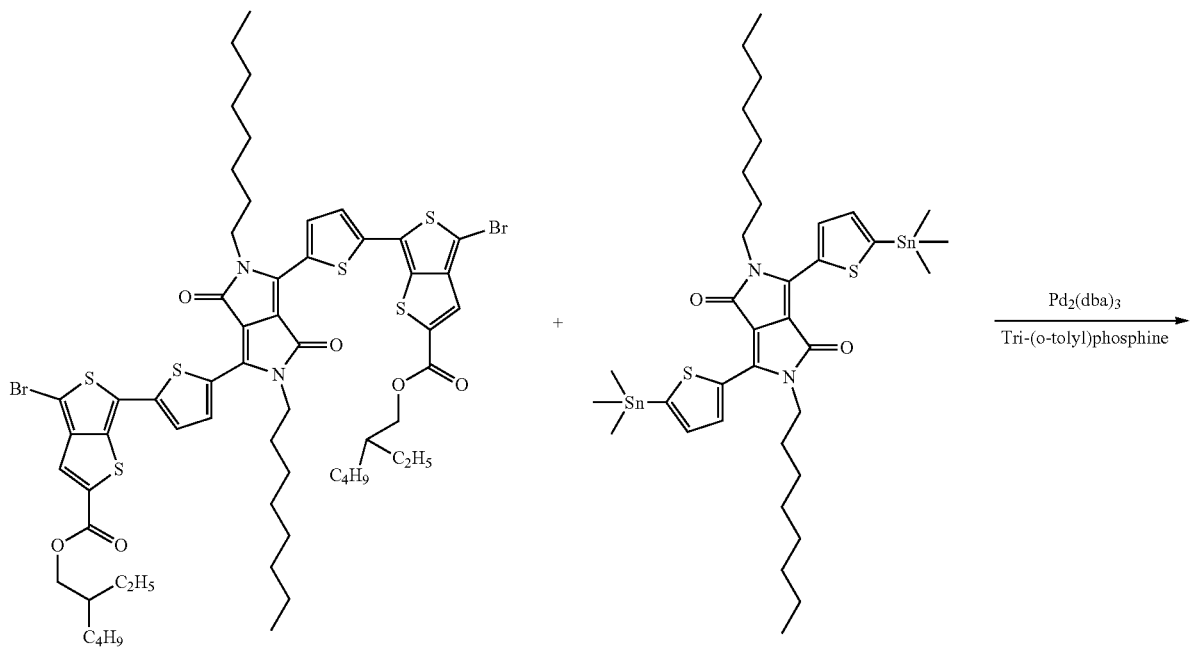

6-b

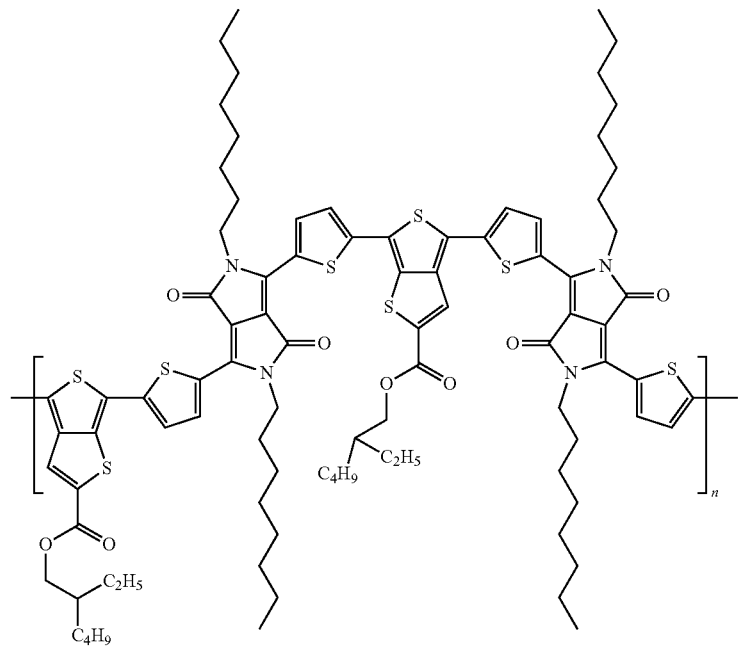

18 ml of chlorobenzene, a compound (0.700 g, 0.5505 mmol) prepared in the same manner as in Example 1 except that the compound of Chemical Formula 6-b was used instead of 2,6-Bis(trimethyltin)-4,8-bis(2-ethylhexyloxy) benzo[1,2-b:4,5-b']dithiophene in the (7) preparation method of Chemical Formula 1-i in Example 1, the compound of Chemical Formula 6-b (0.4681 g, 0.5505 mmol), tris(dibenzylideneacetone)dipalladium(0) (Pd$_2$(dba)$_3$, 10 mg), and tri-(o-tolyl) phosphine (28 mg) were placed in a microwave reactor vial, and the mixture was reacted for 1 hour under a condition of 170° C. The mixture was cooled to room temperature, poured into methanol, and solids were filtered. The filtered solids were Soxhlet extracted with acetone, hexane, methylene chloride and chloroform, and solids were filtered by precipating the chloroform part again in methanol.

Yield: 41%
Number Average Molecular Weight: 40,800 g/mol
PDI: 1.7

Preparation Example 4. Synthesis of Chemical Formula 1-1-4

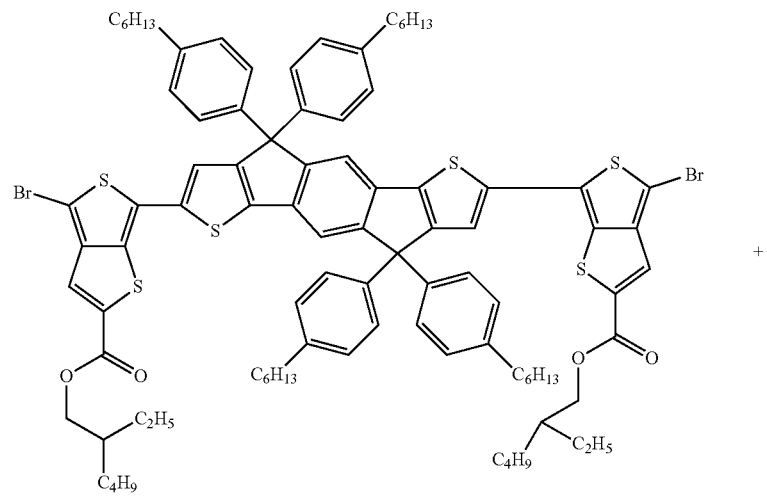

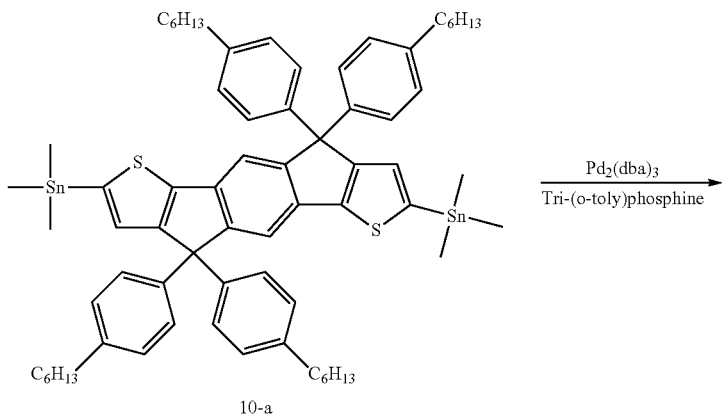

10-a

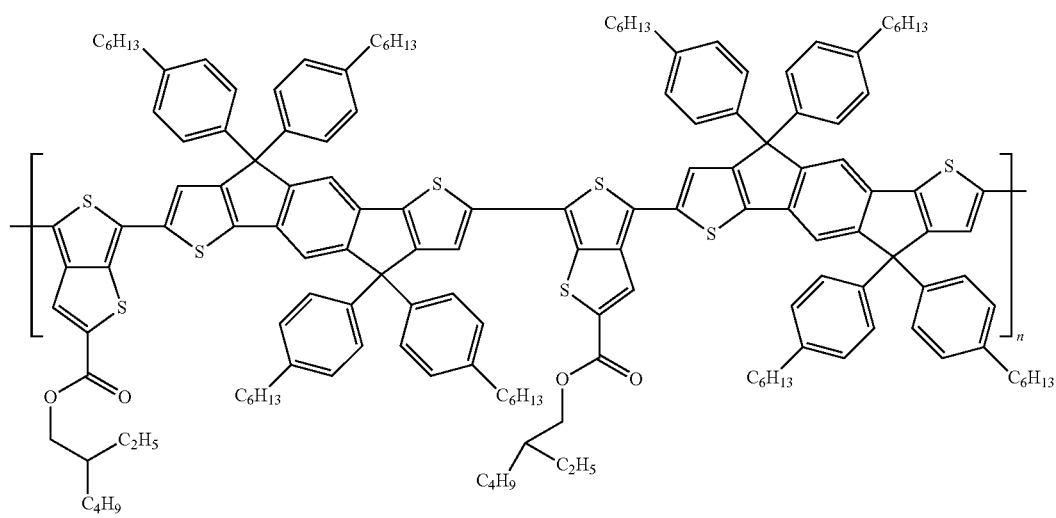

18 ml of chlorobenzene, a compound (0.700 g, 0.4232 mmol) prepared in the same manner as in Example 1 except that the compound of Chemical Formula 10-a was used instead of 2,6-bis(trimethyltin)-4,8-bis(2-ethylhexyloxy) benzo[1,2-b:4,5-b']dithiophene in the (7) preparation method of Chemical Formula 1-i in Example 1, the compound of Chemical Formula 10-a (0.5217 g, 0.4232 mmol), tris(dibenzylideneacetone)dipalladium(0) ($Pd_2(dba)_3$, 10 mg), and tri-(o-tolyl) phosphine (28 mg) were placed in a microwave reactor vial, and the mixture was reacted for 1 hour under a condition of 170° C. The mixture was cooled to room temperature, poured into methanol, and solids were filtered. The filtered solids were Soxhlet extracted with acetone, hexane, methylene chloride and chloroform, and solids were filtered by precipating the chloroform part again in methanol.

Yield: 46%
Number Average Molecular Weight: 57,000 g/mol
PDI: 1.4

Preparation Example 5. Synthesis of Chemical Formula 1-1-5
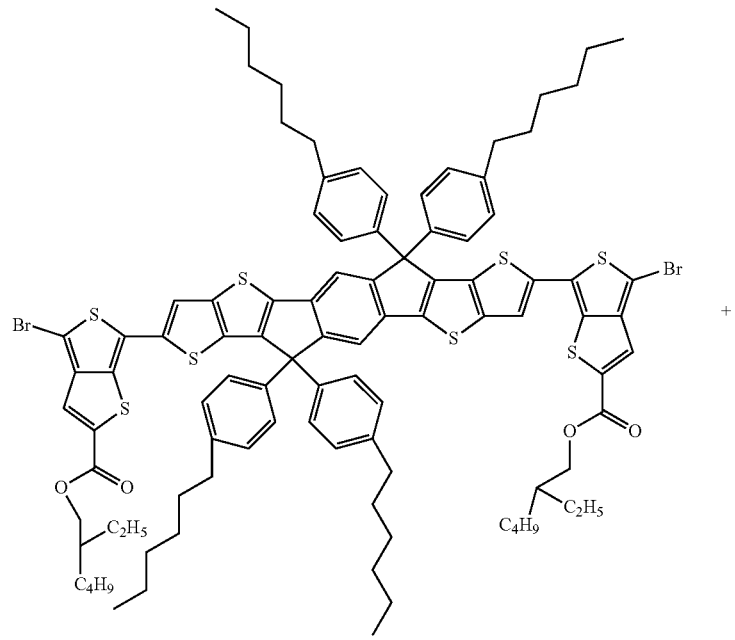
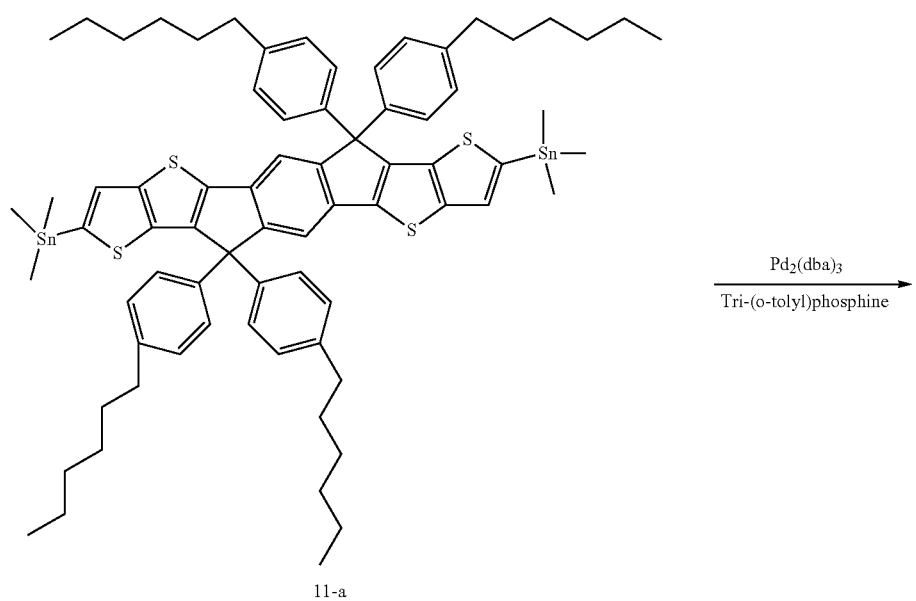
11-a -continued

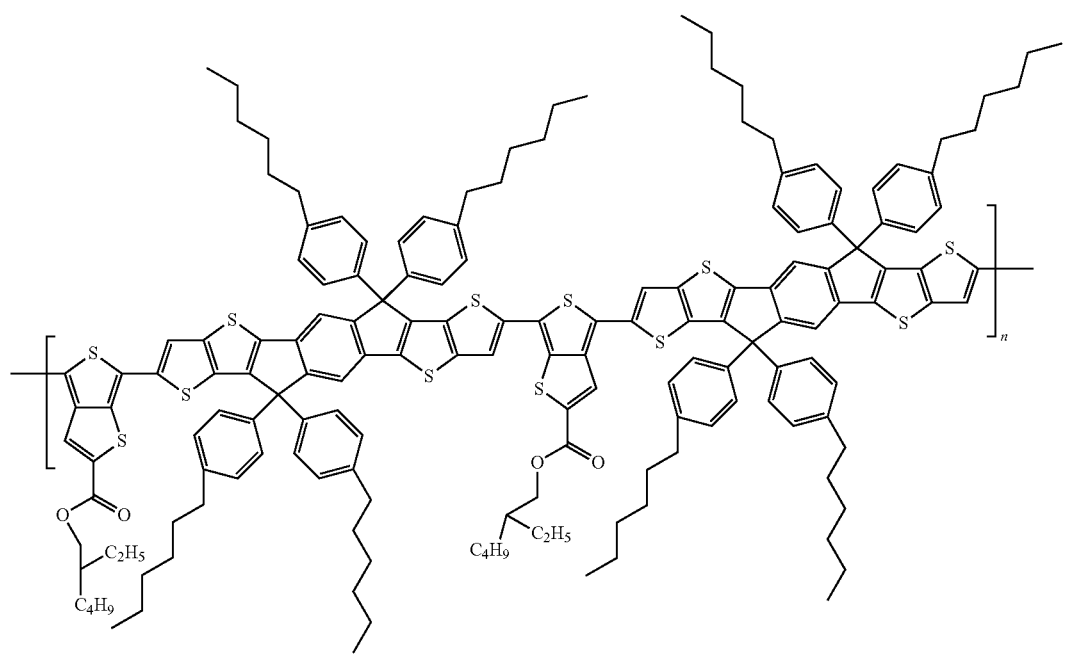

18 ml of chlorobenzene, a compound (0.700 g, 0.3954 mmol) prepared in the same manner as in Example 1 except that the compound of Chemical Formula 11-a was used instead of 2,6-bis(trimethyltin)-4,8-bis(2-ethylhexyloxy) benzo[1,2-b:4,5-b′]dithiophene in the (7) preparation method of Chemical Formula 1-i in Example 1, the compound of Chemical Formula 11-a (0.5319 g, 0.3954 mmol), tris(dibenzylideneacetone)dipalladium(0) (Pd$_2$(dba)$_3$, 10 mg), and tri-(o-tolyl) phosphine (28 mg) were placed in a microwave reactor vial, and the mixture was reacted for 1 hour under a condition of 170° C. The mixture was cooled to room temperature, poured into methanol, and solids were filtered. The filtered solids were Soxhlet extracted with acetone, hexane, methylene chloride and chloroform, and solids were filtered by precipating the chloroform part again in methanol.

Yield: 45%
Number Average Molecular Weight: 52,800 g/mol
PDI: 1.5

Preparation Example 6. Synthesis of Chemical Formula 1-1-6

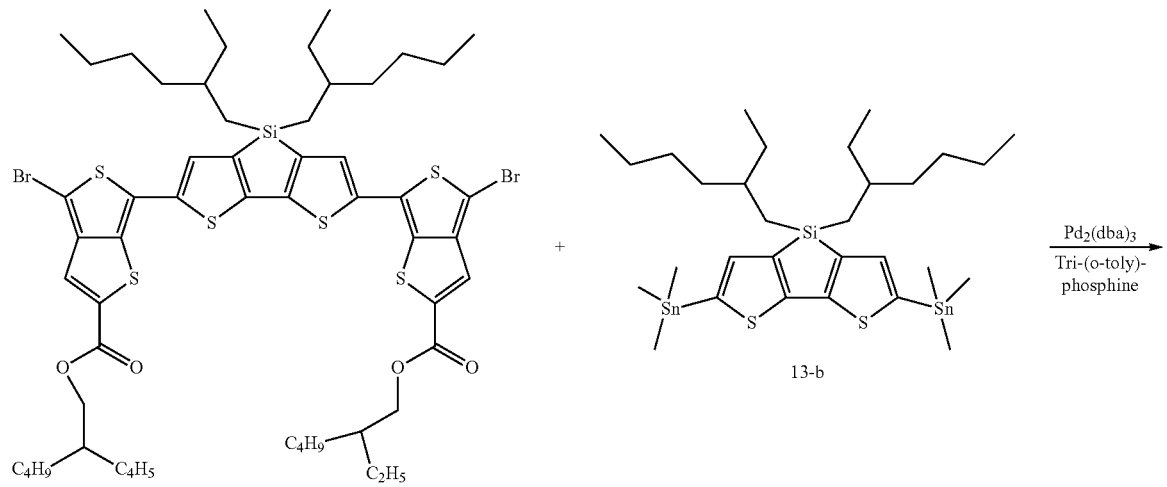

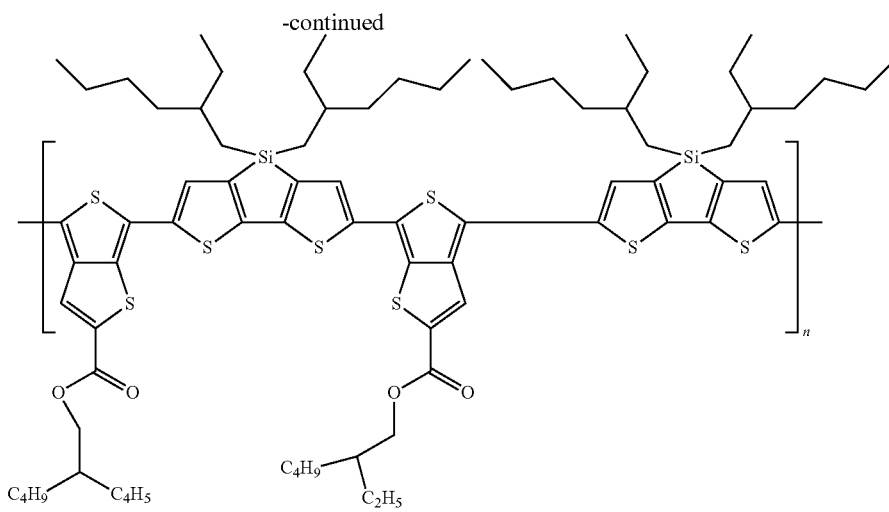

18 ml of chlorobenzene, a compound (0.700 g, 0.6006 mmol) prepared in the same manner as in Example 1 except that the compound of Chemical Formula 13-b was used instead of 2,6-bis(trimethyltin)-4,8-bis(2-ethylhexyloxy) benzo[1,2-b:4,5-b']dithiophene in the (7) preparation method of Chemical Formula 1-i in Example 1, the compound of Chemical Formula 13-b (0.4470 g, 0.6006 mmol), tris(dibenzylideneacetone)dipalladium (0) (Pd$_2$(dba)$_3$, 10 mg), and tri-(o-tolyl) phosphine (28 mg) were placed in a microwave reactor vial, and the mixture was reacted for 1 hour under a condition of 170° C. The mixture was cooled to room temperature, poured into methanol, and solids were filtered. The filtered solids were Soxhlet extracted with acetone, hexane, methylene chloride and chloroform, and solids were filtered by precipating the chloroform part again in methanol.

Yield: 49%

Number Average Molecular Weight: 41,100 g/mol

PDI: 1.9

Preparation Example 7. Synthesis of Chemical Formula 1-1-7

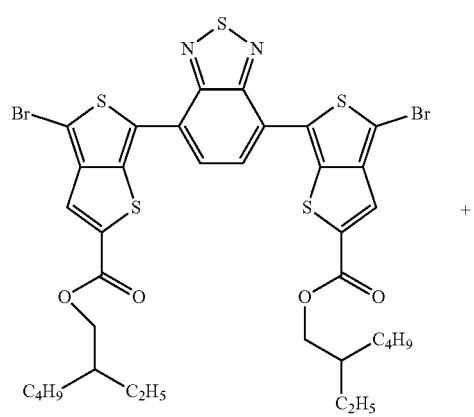

+

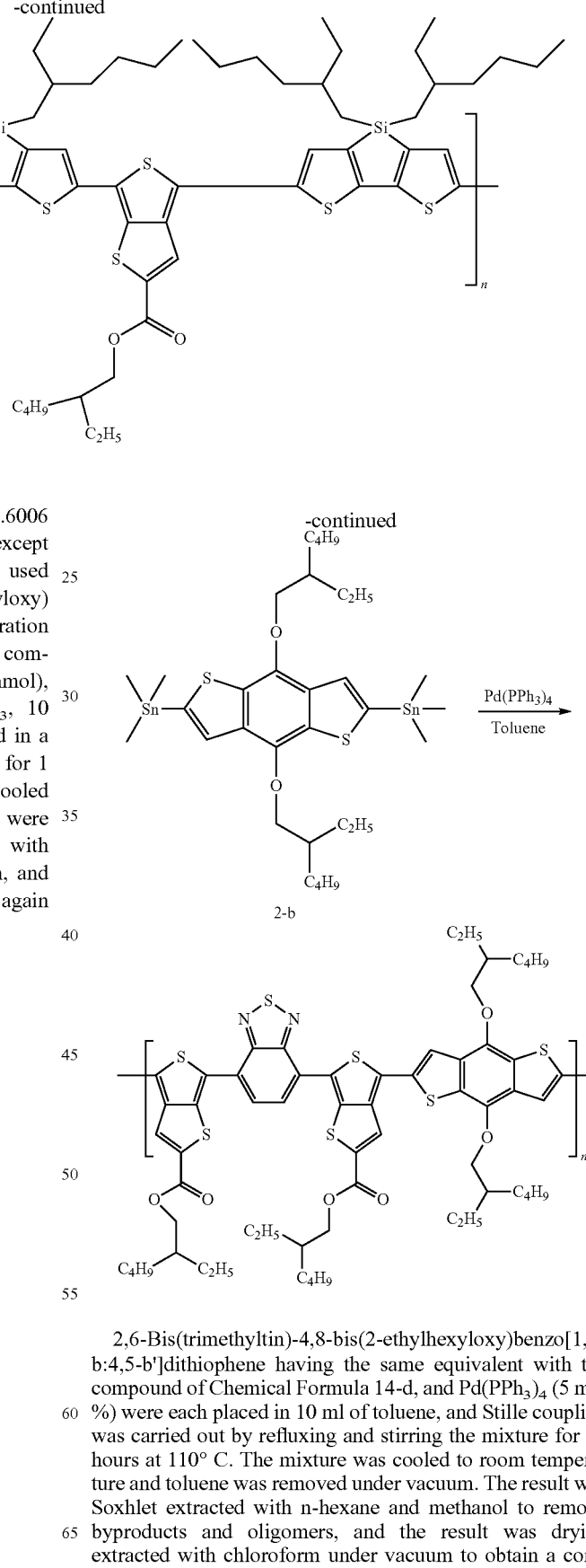

2,6-Bis(trimethyltin)-4,8-bis(2-ethylhexyloxy)benzo[1,2-b:4,5-b']dithiophene having the same equivalent with the compound of Chemical Formula 14-d, and Pd(PPh$_3$)$_4$ (5 mol %) were each placed in 10 ml of toluene, and Stille coupling was carried out by refluxing and stirring the mixture for 24 hours at 110° C. The mixture was cooled to room temperature and toluene was removed under vacuum. The result was Soxhlet extracted with n-hexane and methanol to remove byproducts and oligomers, and the result was drying extracted with chloroform under vacuum to obtain a compound of Chemical Formula 1-1-7.

Preparation Example 8. Synthesis of Chemical Formula 1-1-8

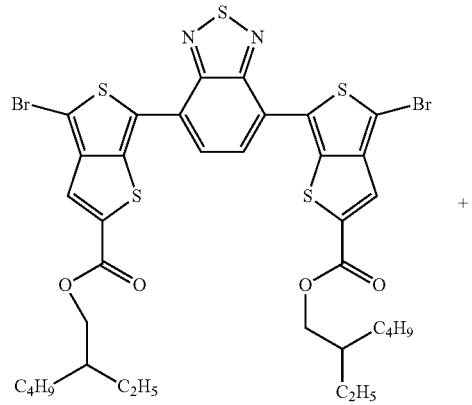

+

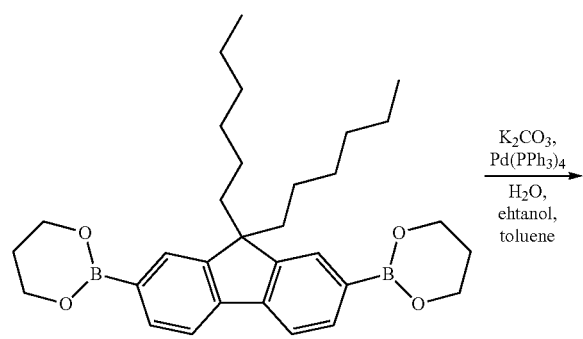

9,9-Dihexylfluorene-2,7-diboronic acid bis(1,3-propanediol)ester having the same equivalent with the compound of Chemical Formula 14-d, Pd(PPh$_3$)$_4$ (5 mol %) were each placed in 10 ml of toluene, and suzuki coupling was carried out. An aqueous sodium carbonate solution (5 ml) and ethanol (5 ml) were placed in a round flask, and the result was refluxed and stirred under a nitrogen atmosphere for 24 hours at 110° C.

The mixture was cooled to room temperature, deionized (DI) water was poured thereto, and the result was extracted with chloroform. The solvent was removed under vacuum, and the result was dried using anhydrous sodium sulfate. The result was Soxhlet extracted with n-hexane and methanol to remove byproducts and oligomers, and the result was drying extracted with chloroform under vacuum to obtain a compound of Chemical Formula 1-1-8.

Preparation Example 9. Synthesis of Chemical Formula 1-1-9

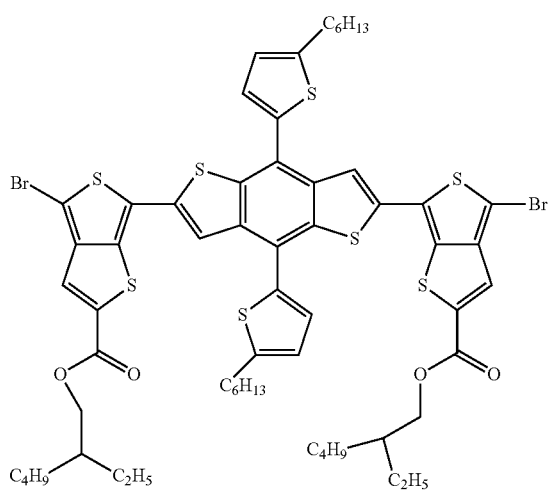

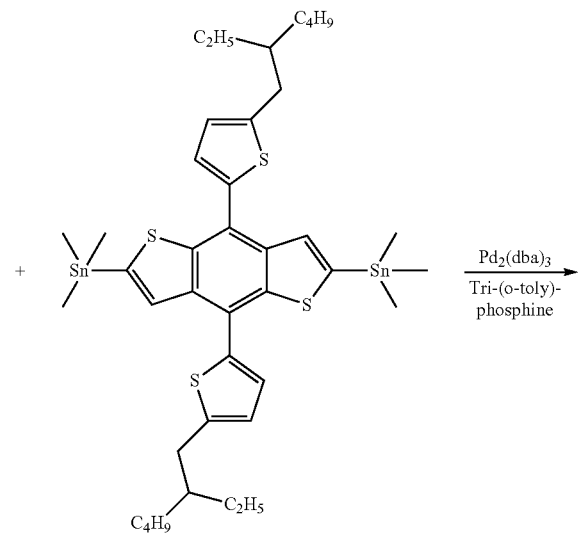

9-b

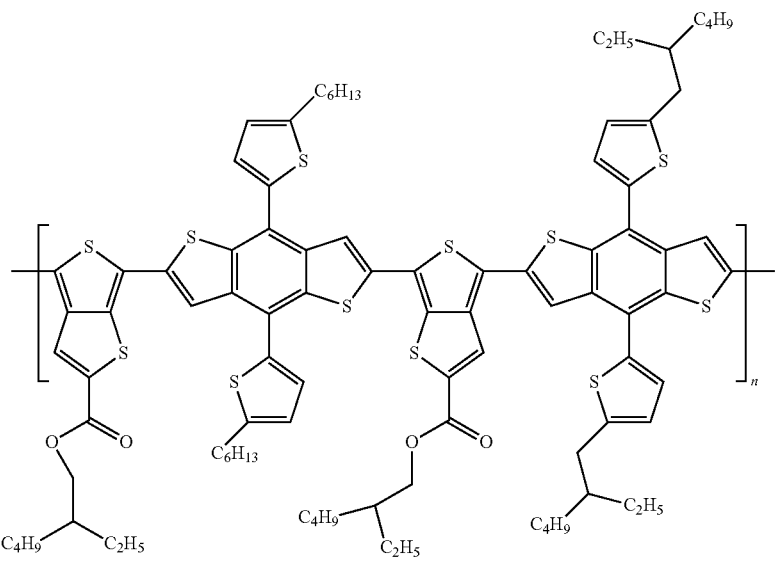

18 ml of chlorobenzene, a compound (0.700 g, 0.5514 mmol) prepared in the same manner as in Example 1 except that the compound of Chemical Formula 9-b was used instead of 2,6-bis(trimethyltin)-4,8-bis(2-ethylhexyloxy) benzo[1,2-b:4,5-b']dithiophene in the (7) preparation method of Chemical Formula 1-i in Example 1, the compound of Chemical Formula 9-b (0.4987 g, 0.5514 mmol), tris(dibenzylideneacetone)dipalladium(0) (Pd$_2$(dba)$_3$, 10 mg), and tri-(o-tolyl) phosphine (28 mg) were placed in a microwave reactor vial, and the mixture was reacted for 1 hour under a condition of 170° C. The mixture was cooled to room temperature, poured into methanol, and solids were filtered. The filtered solids were Soxhlet extracted with acetone, hexane, methylene chloride and chloroform, and solids were filtered by precipating the chloroform part again in methanol.

Yield: 46%
Number Average Molecular Weight: 32,000 g/mol
PDI: 2.0

Preparation Example 10. Synthesis of Chemical Formula 1-1-10

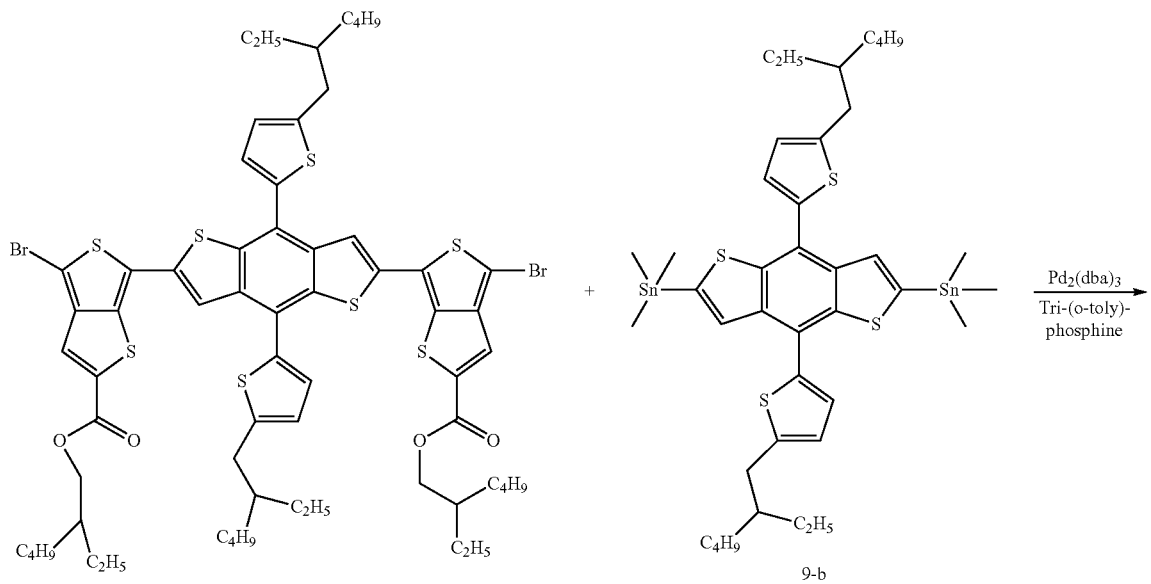

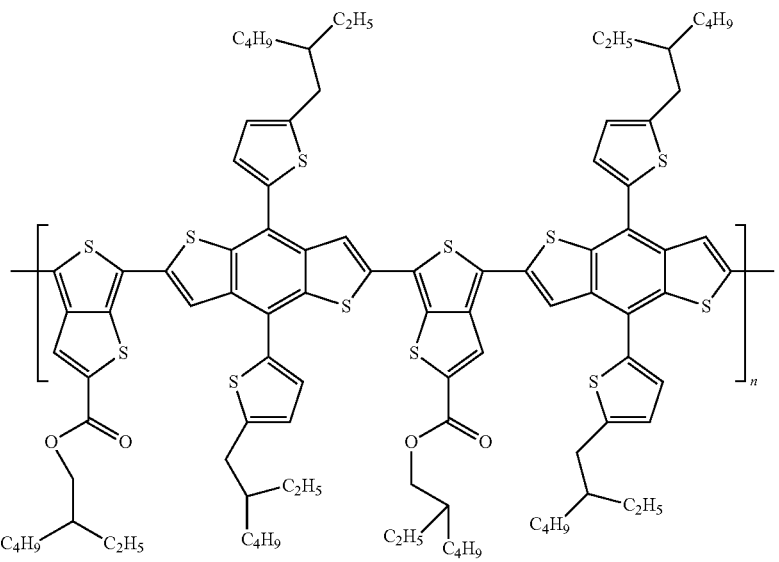

18 ml of chlorobenzene, a compound (0.700 g, 0.5280 mmol) prepared in the same manner as in Example 1 except that the compound of Chemical Formula 9-b was used instead of 2,6-bis(trimethyltin)-4,8-bis(2-ethylhexyloxy) benzo[1,2-b:4,5-b']dithiophene in the (7) preparation method of Chemical Formula 1-i in Example 1, the compound of Chemical Formula 9-b (0.4776 g, 0.5280 mmol), tris(dibenzylideneacetone)dipalladium(0) (Pd$_2$ (dba)$_3$, 10 mg), and tri-(o-tolyl) phosphine (28 mg) were placed in a microwave reactor vial, and the mixture was reacted for 1 hour under a condition of 170° C. The mixture was cooled to room temperature, poured into methanol, and solids were filtered. The filtered solids were Soxhlet extracted with acetone, hexane, methylene chloride and chloroform, and solids were filtered by precipating the chloroform part again in methanol.

Yield: 48%
Number Average Molecular Weight: 54,000 g/mol
PDI: 1.8

Preparation Example 11. Synthesis of Chemical Formula 1-1-11

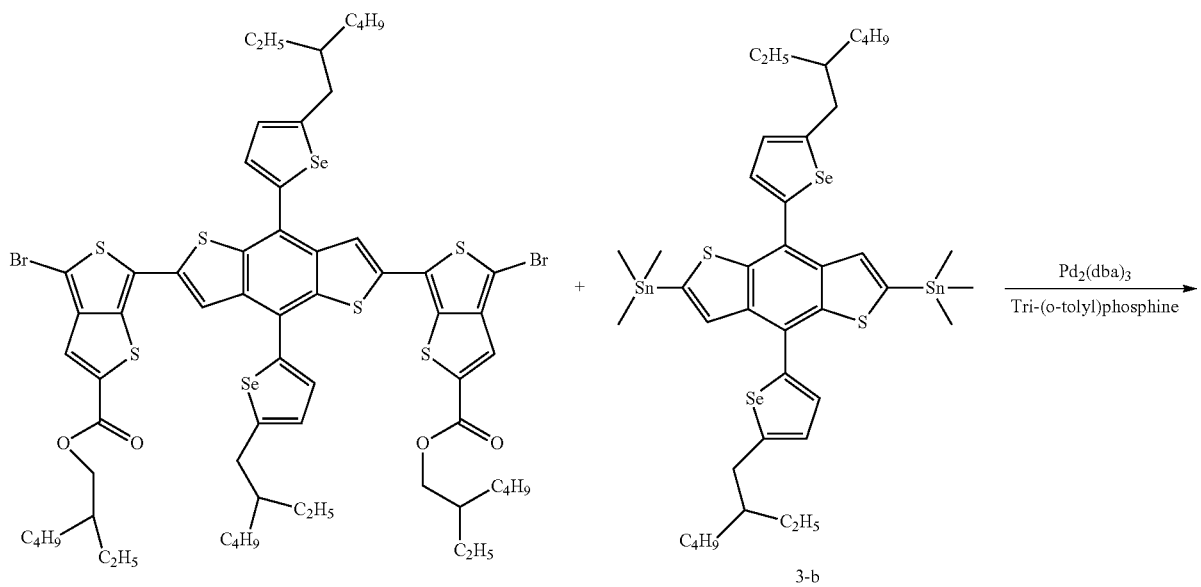

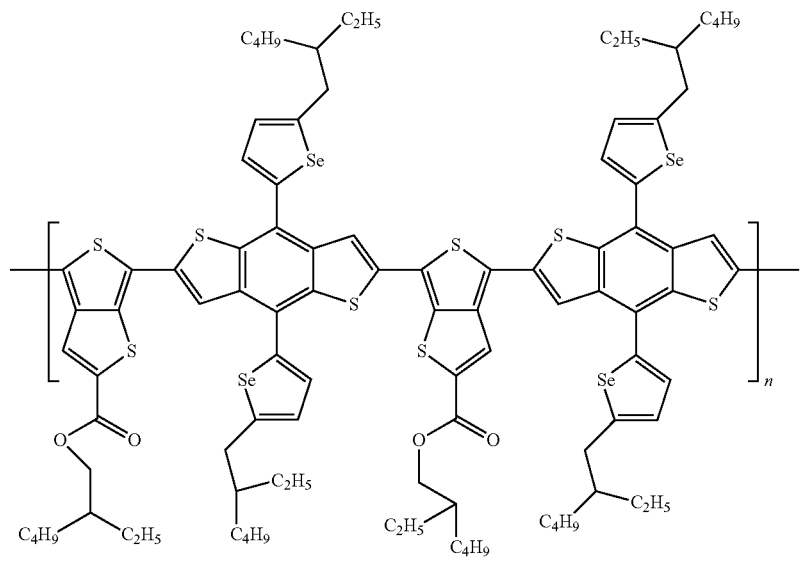

18 ml of chlorobenzene, a compound (0.700 g, 0.4932 mmol) prepared in the same manner as in Example 1 except that the compound of Chemical Formula 3-b was used instead of 2,6-bis(trimethyltin)-4,8-bis(2-ethylhexyloxy) benzo[1,2-b:4,5-b']dithiophene in the (7) preparation method of Chemical Formula 1-i in Example 1, the compound of Chemical Formula 3-b (0.4923 g, 0.4932 mmol), tris(dibenzylideneacetone)dipalladium(0) (Pd$_2$(dba)$_3$, 10 mg), and tri-(o-tolyl) phosphine (28 mg) were placed in a microwave reactor vial, and the mixture was reacted for 1 hour under a condition of 170° C. The mixture was cooled to room temperature, poured into methanol, and solids were filtered. The filtered solids were Soxhlet extracted with acetone, hexane, methylene chloride and chloroform, and solids were filtered by precipating the chloroform part again in methanol.

Yield: 48%
Number Average Molecular Weight: 54,000 g/mol
PDI: 1.8

Preparation Example 12. Synthesis of Chemical Formula 1-1-12

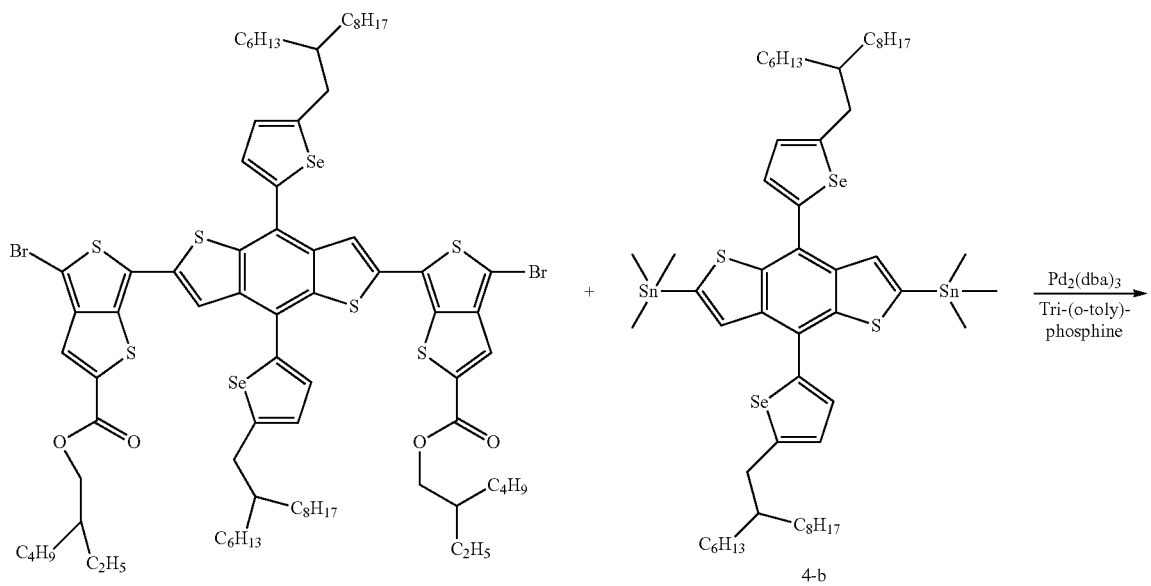

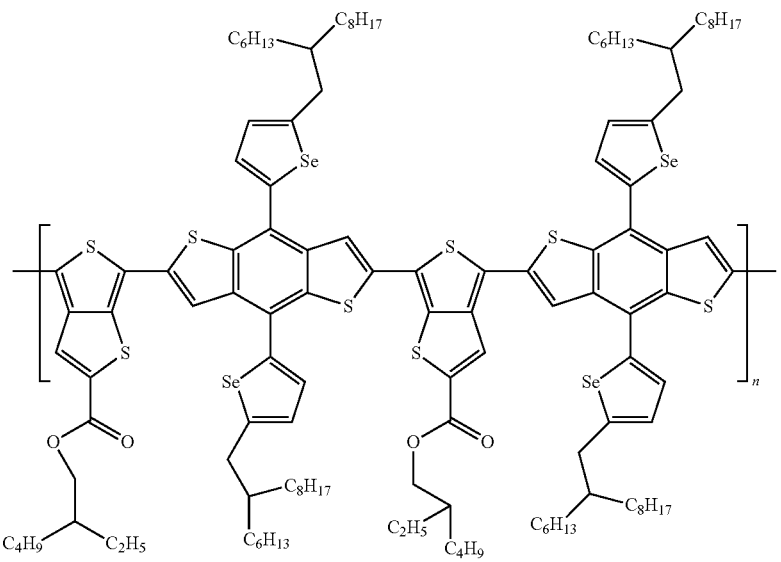

18 ml of chlorobenzene, a compound (0.700 g, 0.4258 mmol) prepared in the same manner as in Example 1 except that the compound of Chemical Formula 4-b was used instead of 2,6-bis(trimethyltin)-4,8-bis(2-ethylhexyloxy)benzo[1,2-b:4,5-b']dithiophene in the (7) preparation method of Chemical Formula 1-i in Example 1, the compound of Chemical Formula 4-b (0.5206 g, 0.4258 mmol), tris(dibenzylideneacetone)dipalladium(0) (Pd$_2$(dba)$_3$, 10 mg), and tri-(o-tolyl) phosphine (28 mg) were placed in a microwave reactor vial, and the mixture was reacted for 1 hour under a condition of 170° C. The mixture was cooled to room temperature, poured into methanol, and solids were filtered. The filtered solids were Soxhlet extracted with acetone, hexane, methylene chloride and chloroform, and solids were filtered by precipating the chloroform part again in methanol.

Yield: 47%
Number Average Molecular Weight: 61,000 g/mol
PDI: 1.6

Preparation Example 13. Synthesis of Chemical Formula 1-1-13

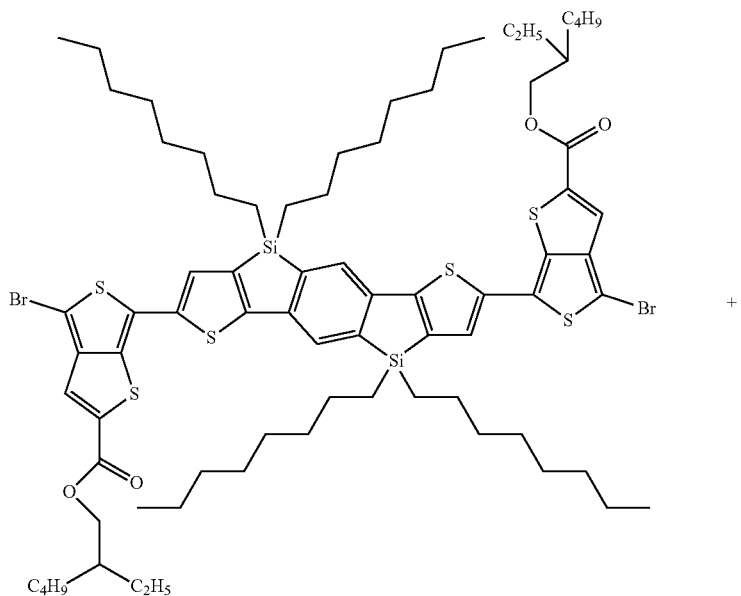

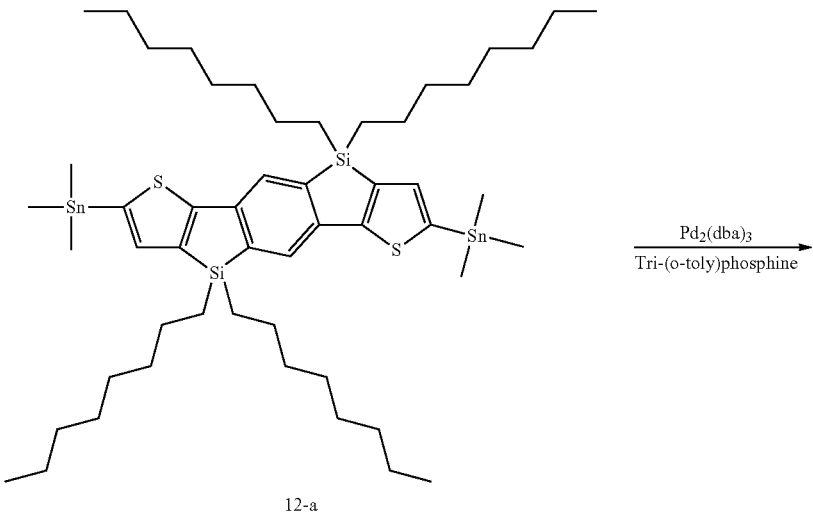

12-a

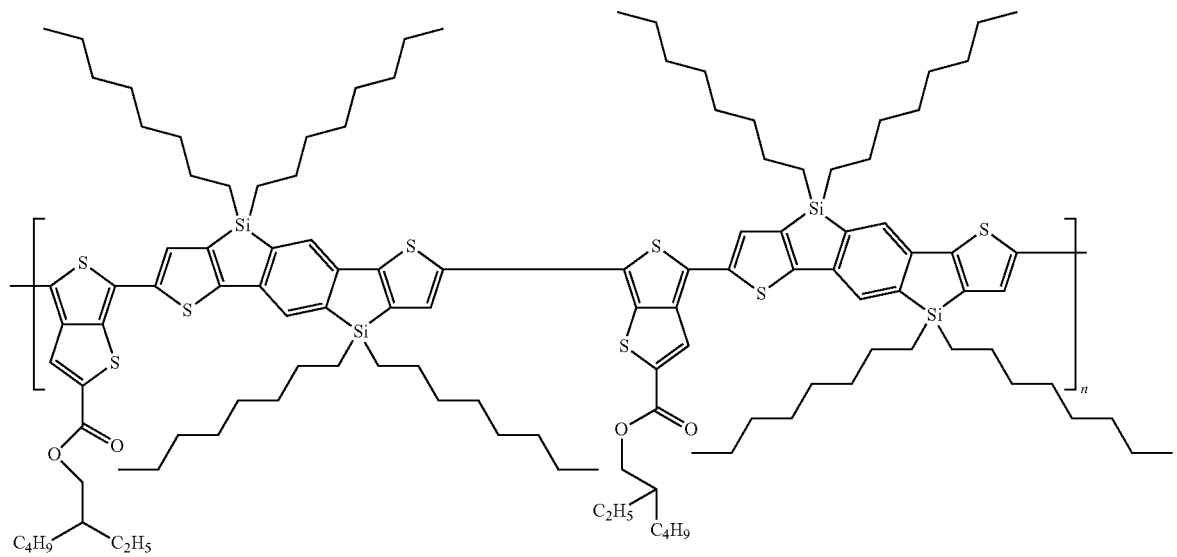

18 ml of chlorobenzene, a compound (0.700 g, 0.4685 mmol) prepared in the same manner as in Example 1 except that the compound of Chemical Formula 12-a was used instead of 2,6-bis(trimethyltin)-4,8-bis(2-ethylhexyloxy)benzol[1,2-b:4,5-b']dithiophene in the (7) preparation method of Chemical Formula 1-i in Example 1, the compound of Chemical Formula 12-a (0.5027 g, 0.4685 mmol), tris(dibenzylideneacetone)dipalladium(0) (Pd$_2$ (dba)$_3$, 10 mg), and tri-(o-tolyl) phosphine (28 mg) were placed in a microwave reactor vial, and the mixture was reacted for 1 hour under a condition of 170° C. The mixture was cooled to room temperature, poured into methanol, and solids were filtered. The filtered solids were Soxhlet extracted with acetone, hexane, methylene chloride and chloroform, and solids were filtered by precipating the chloroform part again in methanol.

Yield: 32%

Number Average Molecular Weight: 21,000 g/mol

PDI: 2.3

Preparation Example 14. Synthesis of Chemical Formula 1-1-14

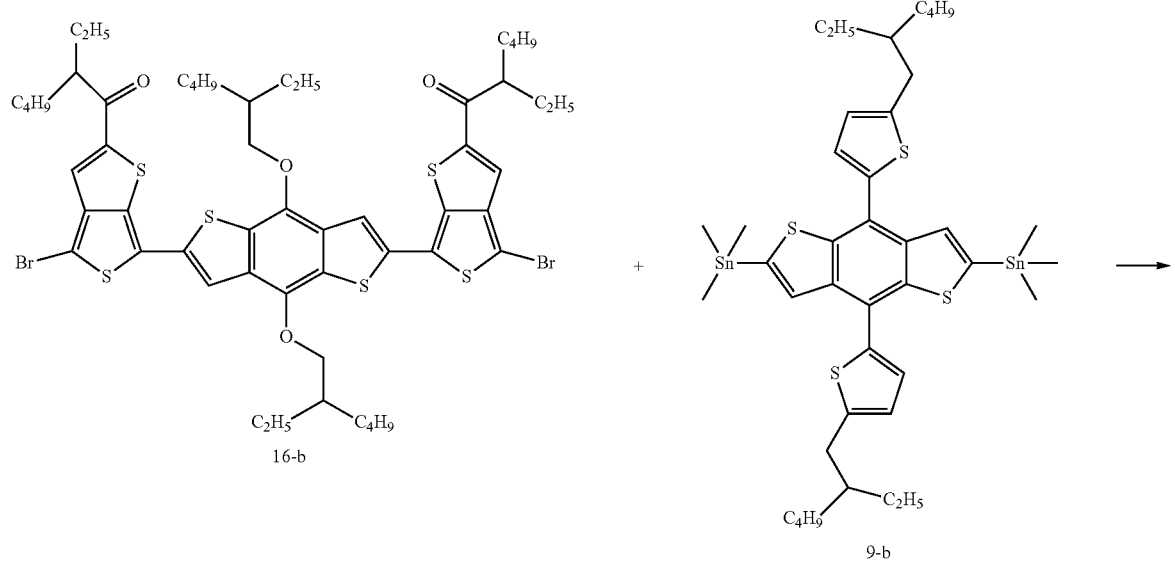

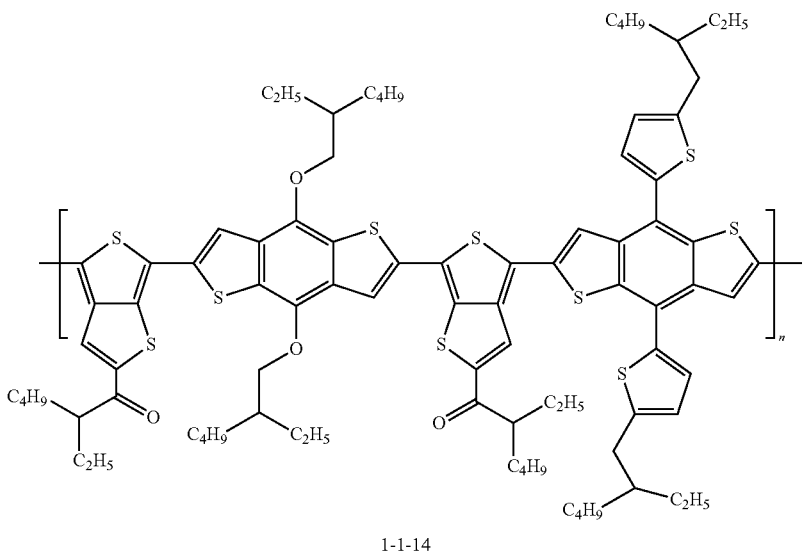

12 ml of chlorobenzene, 16-b (0.700 g, 0.6194 mmol), the compound of Chemical Formula 9-b (0.560 g, 0.6194 mmol), tris(dibenzylideneacetone)dipalladium(0) ($Pd_2(dba)_3$, 10 mg), and tri-(o-tolyl) phosphine (28 mg) were placed in a microwave reactor vial, and the mixture was reacted for 1 hour under a condition of 170° C.

The mixture was cooled to room temperature, poured into methanol, and solids were filtered. The filtered solids were Soxhlet extracted with acetone, hexane, methylene chloride and chloroform, and solids were filtered by precipating the chloroform part again in methanol.

Yield: 43%
Number Average Molecular Weight: 38,000 g/mol
PDI: 1.9

FIG. 36 is a diagram showing a UV-Vis absorption spectrum of Chemical Formula 1-1-14 in a solution state.

FIG. 37 is a diagram showing a UV-Vis absorption spectrum of Chemical Formula 1-1-14 in a film state.

FIG. 38 shows an electrochemical (cyclic voltammetry) measurement result of Chemical Formula 1-1-14.

FIG. 39 is a diagram showing a thermogravimetric analysis (TGA) result of Chemical Formula 1-1-14.

Preparation Example 15. Synthesis of Chemical Formula 1-1-15

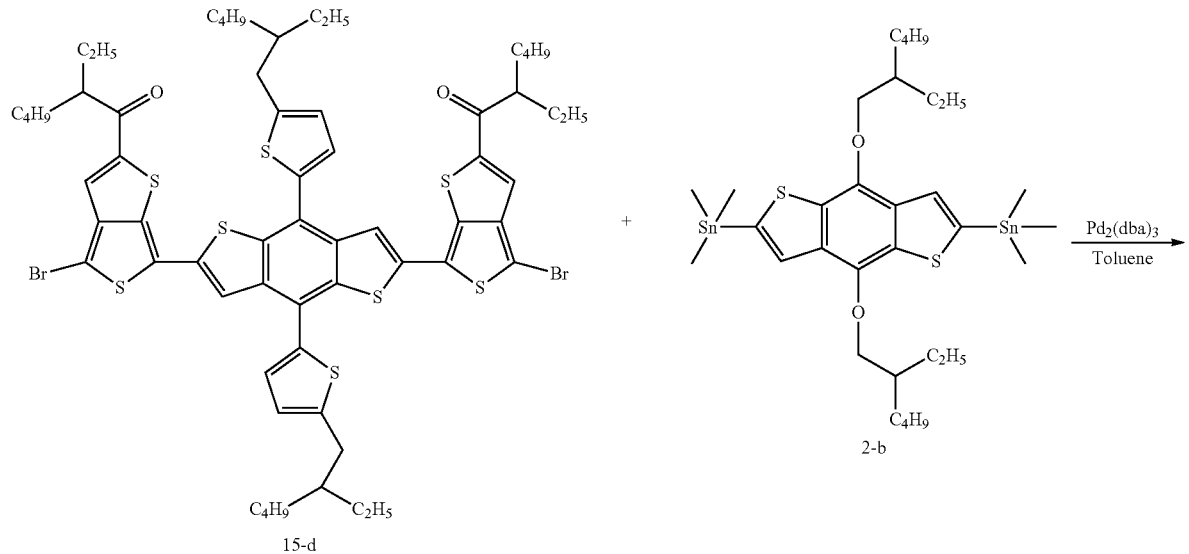

8 ml of chlorobenzene, 15-d (0.500 g, 0.3955 mmol), the compound of Chemical Formula 2-b (0.3053 g, 0.3966 mmol), tris(dibenzylideneacetone)dipalladium (0) (Pd$_2$(dba)$_3$, 10 mg), and tri-(o-tolyl) phosphine (28 mg) were placed in a microwave reactor vial, and the mixture was reacted for 1 hour under a condition of 170° C. The mixture was cooled to room temperature, poured into methanol, and solids were filtered. The filtered solids were Soxhlet extracted with acetone, hexane, methylene chloride and chloroform, and solids were filtered by precipating the chloroform part again in methanol.

Yield: 47%

Number Average Molecular Weight: 41,000 g/mol

PDI: 2.1

FIG. 40 is a diagram showing a UV-Vis absorption spectrum of Chemical Formula 1-1-15 in a solution state.

FIG. 41 is a diagram showing a UV-Vis absorption spectrum of Chemical Formula 1-1-15 in a film state.

FIG. 42 shows an electrochemical (cyclic voltammetry) measurement result of Chemical Formula 1-1-15.

FIG. 43 is a diagram showing a thermogravimetric analysis (TGA) result of Chemical Formula 1-1-15.

Preparation Example 16. Synthesis of Chemical Formula 1-1-16

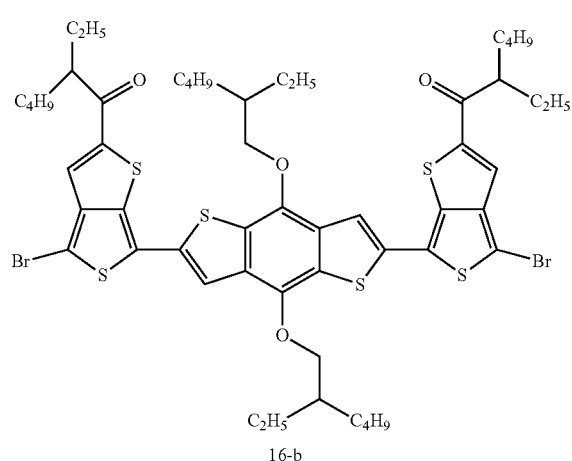

16-b

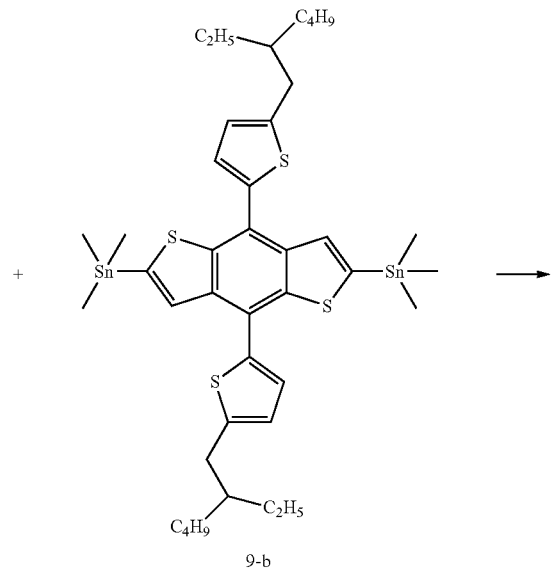

9-b

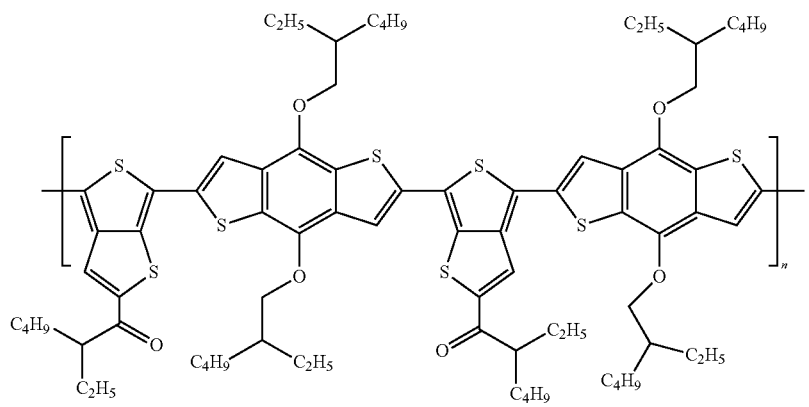

1-1-16

8 ml of chlorobenzene, 16-b (0.500 g, 0.4416 mmol), the compound of Chemical Formula 2-b (0.3409 g, 0.4416 mmol), tris(dibenzylideneacetone)dipalladium (0) (Pd$_2$(dba)$_3$, 10 mg), and tri-(o-tolyl) phosphine (28 mg) were placed in a microwave reactor vial, and the mixture was reacted for 1 hour under a condition of 170° C. The mixture was cooled to room temperature, poured into methanol, and solids were filtered. The filtered solids were Soxhlet extracted with acetone, hexane, methylene chloride and chloroform, and solids were filtered by precipating the chloroform part again in methanol.

Yield: 44%
Number Average Molecular Weight: 47,000 g/mol
PDI: 1.8

FIG. 44 is a diagram showing a UV-Vis absorption spectrum of Chemical Formula 1-1-16 in a solution state.

FIG. 45 is a diagram showing a UV-Vis absorption spectrum of Chemical Formula 1-1-16 in a film state.

FIG. 46 shows an electrochemical (cyclic voltammetry) measurement result of Chemical Formula 1-1-16.

FIG. 47 is a diagram showing a thermogravimetric analysis (TGA) result of Chemical Formula 1-1-16.

Preparation Example 17. Synthesis of Chemical Formula 1-1-17

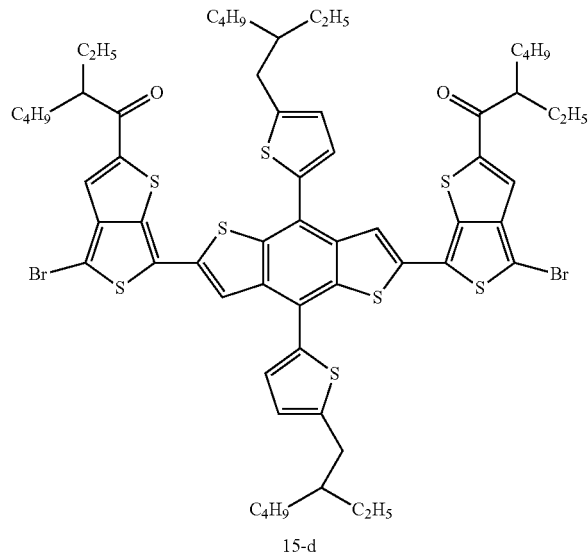

15-d

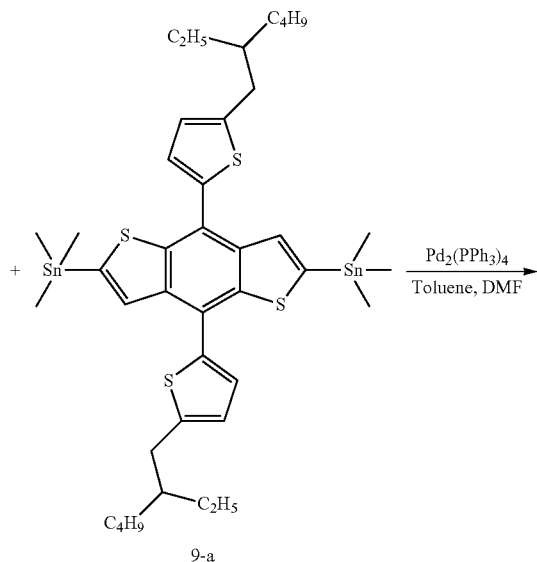

9-a

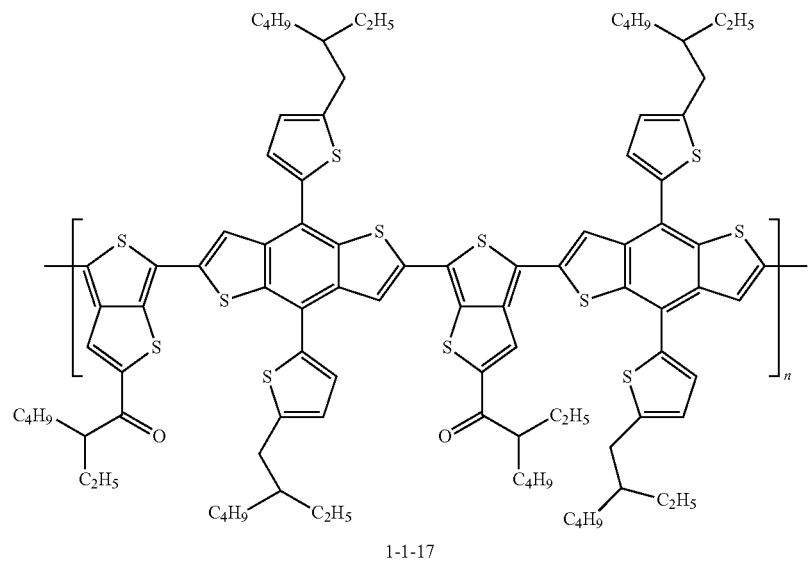

1-1-17

8 ml of chlorobenzene, 15-d (0.500 g, 0.3955 mmol), the compound of Chemical Formula 9-b (0.3583 g, 0.3955 mmol), tris(dibenzylideneacetone)dipalladium (0) ($Pd_2$(dba)$_3$, 10 mg), and tri-(o-tolyl) phosphine (28 mg) were placed in a microwave reactor vial, and the mixture was reacted for 1 hour under a condition of 170° C. The mixture was cooled to room temperature, poured into methanol, and solids were filtered. The filtered solids were Soxhlet extracted with acetone, hexane, methylene chloride and chloroform, and solids were filtered by precipating the chloroform part again in methanol.

Yield: 39%
Number Average Molecular Weight: 49,000 g/mol
PDI: 1.9

FIG. 48 is a diagram showing a UV-Vis absorption spectrum of Chemical Formula 1-1-17 in a solution state.

FIG. 49 is a diagram showing a UV-Vis absorption spectrum of Chemical Formula 1-1-17 in a film state.

FIG. 50 shows an electrochemical (cyclic voltammetry) measurement result of Chemical Formula 1-1-17.

FIG. 51 is a diagram showing a thermogravimetric analysis (TGA) result of Chemical Formula 1-1-17.

FIG. 52 is a diagram showing UV-Vis absorption spectra of Chemical Formulae 1-1-14 to 1-1-17 in a solution state.

FIG. 53 is a diagram showing UV-Vis absorption spectra of Chemical Formulae 1-1-14 to 1-1-17 in a film state.

FIG. 54 shows electrochemical measurement results (cyclic voltammetry) of Chemical Formulae 1-1-14 to 1-1-17.

FIG. 55 is a diagram showing thermogravimetric analysis (TGA) results of Chemical Formulae 1-1-14 to 1-1-17.

Physical properties of Chemical Formulae 1-1-14 to 1-1-17 prepared in Preparation Examples 14 to 17 measured by the UV-Vis absorption spectra, the electrochemical measurements and the thermos gravimetric analyses (TGA) are as shown in the following Table 1.

TABLE 1

| Chemical Formula | $\Lambda_{onset}$ (film) [nm] | $E_g^{opt}$ [eV] | HOMO [eV] | LUMO [eV] | $T_d$ [° C.] |
|---|---|---|---|---|---|
| 1-1-14 | 825 | 1.50 | −5.16 | −3.62 | 333 |
| 1-1-15 | 815 | 1.52 | −5.15 | −3.64 | 347 |
| 1-1-16 | 768 | 1.61 | −5.18 | −3.62 | 330 |
| 1-1-17 | 800 | 1.55 | −5.28 | −3.61 | 422 |

In Table 1, $\Lambda_{onset}$ represents absorbance in a film state, $E_g^{opt}$ represents a band gap, and $T_d$ represents a thermal decomposition temperature.

The UV-Vis absorption spectra of FIGS. 36, 40, 44 and 48 were obtained by analyzing a sample dissolving Chemical Formula 1-1-14, 1-1-15, 1-1-16 or 1-1-17 in chlorobenzene to have a concentration of 1 wt % using a UV-Vis absorption spectrometer.

The UV-Vis absorption spectra of FIGS. 37, 41, 45 and 49 were obtained by dropping a solution dissolving Chemical Formula 1-1-14, 1-1-15, 1-1-16 or 1-1-17 in chlorobenzene to have a concentration of 1 wt % on a glass substrate, spin coating the solution for 60 seconds at 1000 rpm to prepare a sample, heat treating the sample at 80° C., and analyzing the sample using a UV-Vis absorption spectrometer.

The electrochemical (cyclic voltammetry) measurements of FIGS. 38, 42, 46 and 50 were analyzed by a three-electrode system in which a glassy carbon working electrode, an Ag/Agcl reference electrode, and a Pt electrode were put in an electrolyte solution dissolving $Bu_4NBF_4$ in acetonitrile to have a concentration of 0.1 M. Chemical Formula 1-1-14, 1-1-15, 1-1-16 or 1-1-17 was coated on the working electrode using a drop casting method.

FIGS. 39, 43, 47 and 51 are diagrams showing thermogravimetric analysis results of Chemical Formulae 1-1-14 to Chemical Formula 1-1-17, and the temperatures described in FIGS. 39, 43, 47 and 51 each mean a temperature at which the weight of Chemical Formula 1-1-14, 1-1-15, 1-1-16 or 1-1-17 is lost by 5% based on the weight of 100% at the beginning of the analysis, that is, a thermal decomposition temperature ($T_d$).

Experimental Example 1. Fabrication of Organic Solar Cell

A composite solution was prepared by dissolving the compound of Preparation Examples 2 to 6, 9 and 10 as an electron donor and $PC_{60}BM$ as an electron acceptor in chlorobenzene (CB) in a mixing ratio of 7:3 (w/w ratio). Herein, the concentration was adjusted to 4.0 wt %, and the organic solar cell employed an ITO/PEDOT:PSS/photoactive layer/LiF/Al structure. The glass substrate coated with ITO was ultrasonic cleaned using distilled water, acetone and 2-propanol, and after the ITO surface was ozone treated for 10 minutes, the surface was spin-coated with PEDOT:PSS (baytrom P) to a thickness of 45 nm, and then heat treated for 10 minutes at 120° C. In order to coat the photoactive layer, the compound-PCBM composite solution was filtered using a PP syringe filter of 0.45 μm, then spin-coated, and deposited with Al to a thickness of 200 nm using a thermal evaporator under a vacuum of $3 \times 10^{-8}$ torr, and as a result, the organic solar cell was fabricated.

TABLE 2

| | Active Layer | $V_{oc}$ (V) | $J_{sc}$ (mA/cm$^2$) | FF (%) | PCE (%) |
|---|---|---|---|---|---|
| Experimental Example 1 | Chemical Formula 1-1-2: $PC_{60}BM$ | 0.627 | 9.45 | 0.624 | 3.68 |
| Experimental Example 2 | Chemical Formula 1-1-3: $PC_{60}BM$ | 0.808 | 5.863 | 0.433 | 2.05 |
| Experimental Example 3 | Chemical Formula 1-1-4: $PC_{60}BM$ | 0.616 | 11.65 | 0.556 | 4.00 |
| Experimental Example 4 | Chemical Formula 1-1-5: $PC_{60}BM$ | 0.618 | 11.56 | 0.573 | 4.10 |
| Experimental Example 5 | Chemical Formula 1-1-6: $PC_{60}BM$ | 0.628 | 9.52 | 0.615 | 3.67 |
| Experimental Example 6 | Chemical Formula 1-1-9: $PC_{60}BM$ | 0.822 | 10.57 | 0.575 | 4.99 |
| Experimental Example 7 | Chemical Formula 1-1-10: $PC_{60}BM$ | 0.824 | 11.41 | 0.671 | 6.30 |
| Experimental Example 8 | Chemical Formula 1-1-11: $PC_{60}BM$ | 0.814 | 10.45 | 0.592 | 5.04 |
| Experimental Example 9 | Chemical Formula 1-1-12: $PC_{60}BM$ | 0.800 | 11.97 | 0.620 | 5.94 |
| Experimental Example 10 | Chemical Formula 1-1-13: $PC_{60}BM$ | 0.838 | 7.99 | 0.356 | 2.38 |

In Table 2, $V_{oc}$ means an open voltage, $J_{sc}$ means a short-circuit current, FF means a fill factor, and PCE means energy conversion efficiency. The open voltage and the short-circuit current are each an x-axis and a y-axis intercept in the four quadrants of a voltage-current density curve, and as these two values increase, solar cell efficiency is preferably enhanced. In addition, the fill factor is a value dividing the rectangle area that may be drawn inside the curve by the product of the short-circuit current and the open voltage. The energy conversion efficiency may be obtained when these three values are divided by the irradiated light, and it is preferable as the value is higher.

FIG. 25 is a diagram showing current density depending on the voltage of the organic solar cell according to Experimental Example 1.

FIG. 26 is a diagram showing current density depending on the voltage of the organic solar cell according to Experimental Example 2.

FIG. 27 is a diagram showing current density depending on the voltage of the organic solar cell according to Experimental Example 3.

FIG. 28 is a diagram showing current density depending on the voltage of the organic solar cell according to Experimental Example 4.

FIG. 29 is a diagram showing current density depending on the voltage of the organic solar cell according to Experimental Example 5.

FIG. 30 is a diagram showing current density depending on the voltage of the organic solar cell according to Experimental Example 6.

FIG. 31 is a diagram showing current density depending on the voltage of the organic solar cell according to Experimental Example 7.

FIG. 32 is a diagram showing current density depending on the voltage of the organic solar cell according to Experimental Example 8.

FIG. 33 is a diagram showing current density depending on the voltage of the organic solar cell according to Experimental Example 9.

FIG. 34 is a diagram showing current density depending on the voltage of the organic solar cell according to Experimental Example 10.

Experimental Example 2. Fabrication of Organic Solar Cell

A composite solution was prepared by dissolving the compound of Preparation Examples 14 to 17 as an electron donor and $PC_{71}BM$ as an electron acceptor in chlorobenzene (CB) in a mixing ratio shown in the following Table 3. Herein, diiodooctane (DIO), an additive, was added in 3 v/v %. The organic solar cell employed an ITO/ZnO(sol-gel)/photoactive layer/$MoO_3$/Ag structure. The glass substrate coated with ITO was ultrasonic cleaned using distilled water, acetone and 2-propanol, and after the ITO surface was ozone treated for 10 minutes, the surface was spin-coated with a mixture, in which 1 g of zinc acetate dehydrate and 0.28 g of ethanolamine were added to 2-methoxyethanol, to a thickness of 40 nm for 40 seconds at 2000 rpm, and annealed for 1 hour at 200° C. In order to coat the photoactive layer, the compound-PCBM composite solution was filtered using a PP syringe filter of 0.45 μm, then spin-coated for 40 seconds at 800 rpm, and deposited with $MoO_3$ to a thickness of 10 nm at 0.2 Å/s and Ag to a thickness of 100 nm at 1 Å/s under a vacuum of $2\times10^{-6}$ torr, and as a result, the organic solar cell was fabricated.

TABLE 3

| | Active Layer | Active Layer Thickness (nm) | $V_{oc}$ (V) | $J_{sc}$ (mA/cm$^2$) | FF (%) | PCE (%) |
|---|---|---|---|---|---|---|
| Experimental Example 11 | Chemical Folmula 1-1-14:$PC_{71}BM$ = 1:2 | 90 | 0.72 | 16.24 | 63.56 | 7.44 |
| Experimental Example 12 | Chemical Formula 1-1-15:$PC_{71}BM$ = 1:2 | 90 | 0.73 | 14.97 | 59.47 | 6.47 |
| Experimental Example 13 | Chemical Formula 1-1-16:$PC_{71}BM$ = 1:1.5 | 80 | 0.71 | 15.49 | 60.54 | 6.64 |
| Experimental Example 14 | Chemical Formula 1-1-17:$PC_{71}BM$ = 1:1.5 | 80 | 0.75 | 15.81 | 63.30 | 7.54 |

In table 3, $V_{oc}$ means an open voltage, $J_{sc}$ means a short-circuit current, FF means a fill factor, and PCE means energy conversion efficiency. The open voltage and the short-circuit current are each an x-axis and a y-axis intercept in the four quadrants of a voltage-current density curve, and as these two values increase, solar cell efficiency is preferably enhanced. In addition, the fill factor is a value dividing the rectangle area that may be drawn inside the curve by the product of the short-circuit current and the open voltage. The energy conversion efficiency may be obtained when these three values are divided by the irradiated light, and it is preferable as the value is higher.

FIG. 35 is a diagram showing current density depending on the voltage of the organic solar cell according to Experimental Examples 11 to 14.

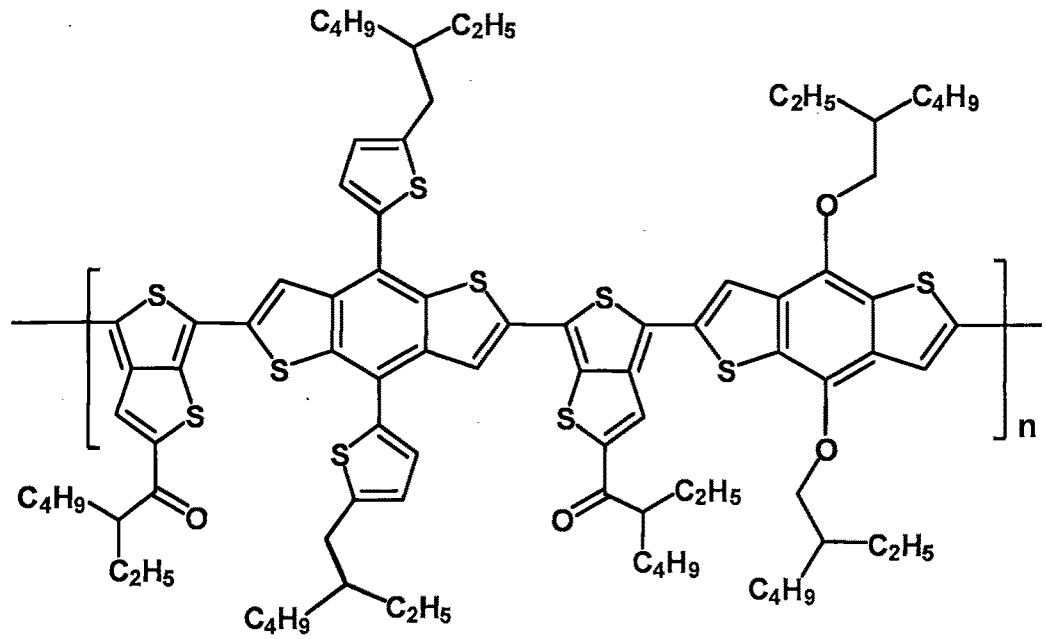

The invention claimed is:

1. A copolymer comprising a unit of Chemical Formula 1:

[Chemical Formula 1]

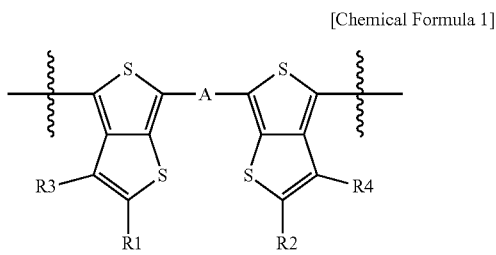

Wherein:

R1 and R2 are the same as or different from each other, and each is independently hydrogen, a halogen group, a nitro group, a cyano group, a carboxyl group, a hydroxyl group, a substituted or unsubstituted carbonyl group, a substituted or unsubstituted alkyl group, a substituted or unsubstituted allyl group, a substituted or unsubstituted alkoxy group, a substituted or unsubstituted cycloalkyl group, a substituted or unsubstituted alkenyl group, a substituted or unsubstituted ester group, a substituted or unsubstituted amide group, a substituted or unsubstituted ether group, a substituted or unsubstituted sulfonyl group, a substituted or unsubstituted sulfoxy group, a substituted or unsubstituted arylalkyl group, a substituted or unsubstituted aryl group, or a substituted or unsubstituted heterocyclic group including one or more of N, O, S and Se atoms;

R3 and R4 are the same as or different from each other, and each is independently hydrogen, or an electron withdrawing group; and A comprises one, two or more of the following chemical formulae:

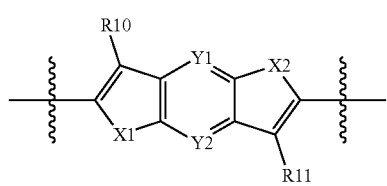

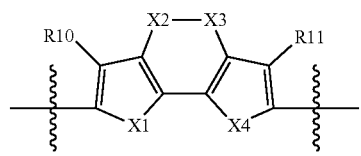

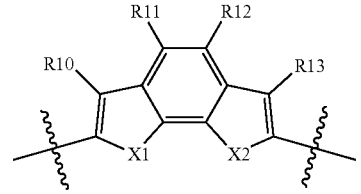

-continued

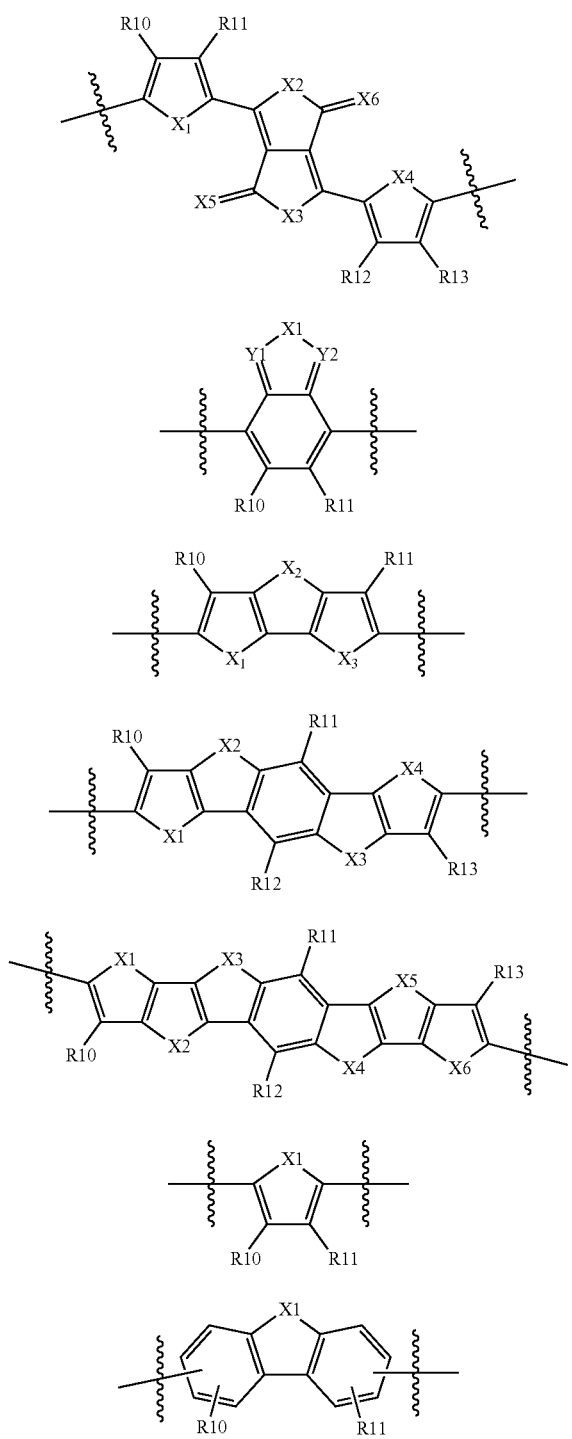

wherein X1 to X6 are the same as or different from each other, and each is independently CRR', NR, O, SiRR', PR, S, GeRR', Se or Te, Y1 and Y2 are the same as or different from each other, and each is independently CR", N, SiR", P or GeR", and R, R', R", and R10 to R13 are the same as or different from each other, and each is independently hydrogen, a halogen group, a nitro group, a cyano group, a carboxyl group, a hydroxyl group, a substituted or unsubstituted carbonyl group, a substituted or unsubstituted alkyl group, a substituted or unsubstituted allyl group, a substituted or unsubstituted alkoxy group, a substituted or unsubstituted cycloalkyl group, a substituted or unsubstituted alkenyl group, a substituted or unsubstituted ester group, a substituted or unsubstituted amide group, a substituted or unsubstituted ether group, a substituted or unsubstituted sulfonyl group, a substituted or unsubstituted sulfoxy group, a substituted or unsubstituted arylalkyl group, a substituted or unsubstituted aryl group, or a substituted or unsubstituted heterocyclic group including one or more of N, O, S and Se atoms.

2. The copolymer of claim 1, wherein the unit of Chemical Formula 1 is a unit of Chemical Formula 2:

[Chemical Formula 2]

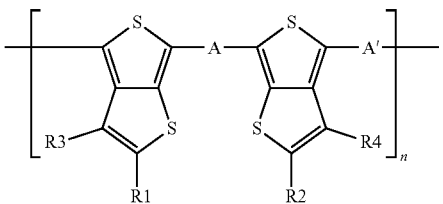

Wherein:

n is an integer of 1 to 10,000;

R1 and R2 are the same as or different from each other, and each is independently hydrogen, a halogen group, a nitro group, a cyano group, a carboxyl group, a hydroxyl group, a substituted or unsubstituted carbonyl group, a substituted or unsubstituted alkyl group, a substituted or unsubstituted allyl group, a substituted or unsubstituted alkoxy group, a substituted or unsubstituted cycloalkyl group, a substituted or unsubstituted alkenyl group, a substituted or unsubstituted ester group, a substituted or unsubstituted amide group, a substituted or unsubstituted ether group, a substituted or unsubstituted sulfonyl group, a substituted or unsubstituted sulfoxy group, a substituted or unsubstituted arylalkyl group, a substituted or unsubstituted aryl group, or a substituted or unsubstituted heterocyclic group including one or more of N, O, S and Se atoms;

R3 and R4 are the same as or different from each other, and each is independently hydrogen, or an electron withdrawing group; and A and A' are the same as or different from each other, A is as defined in claim 1, and A' is a substituted or unsubstituted monocyclic or multicyclic aryl group or a substituted or unsubstituted monocyclic or multicyclic heterocyclic group including one or more of N, O, S and Se atoms.

3. The copolymer of claim 1, wherein A functions as an electron donor or an electron acceptor.

4. The copolymer of claim 1, wherein the unit of Chemical Formula 1 is a unit of any one of the following Chemical Formulae 3 to 10:

[Chemical Formula 3]
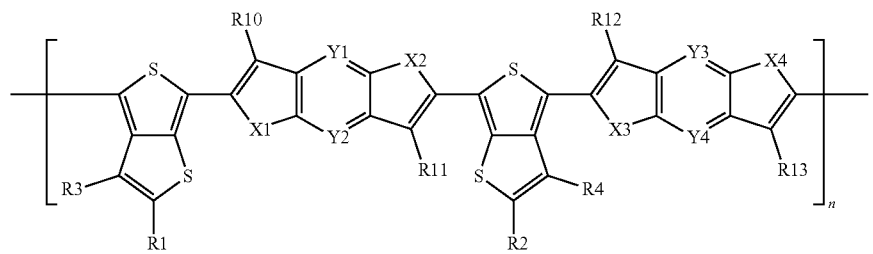
[Chemical Formula 4]
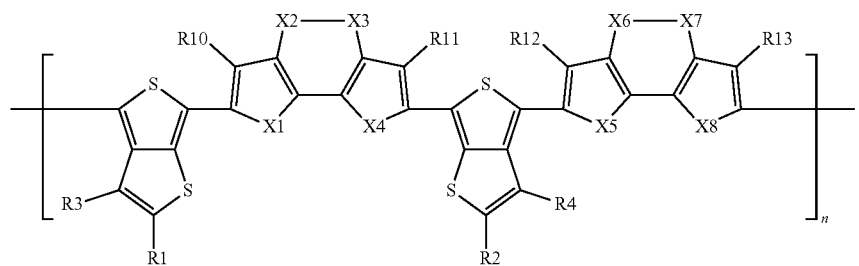
[Chemical Formula 5]
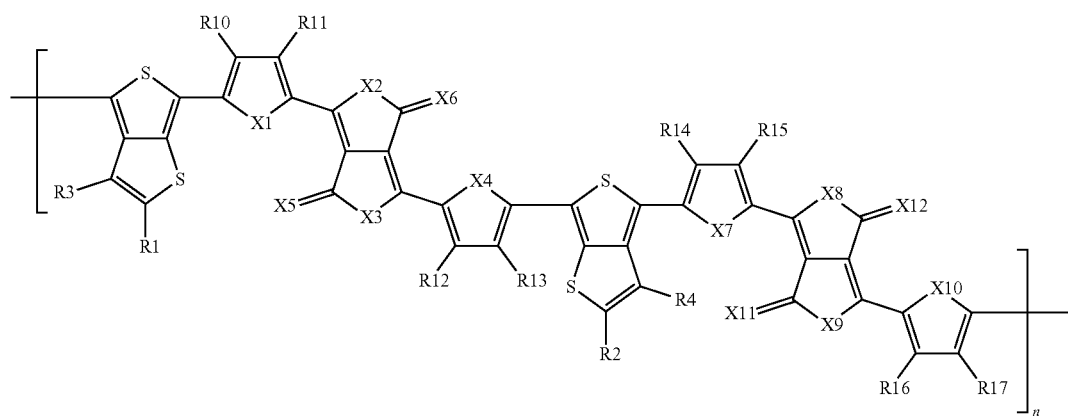
[Chemical Formula 6]
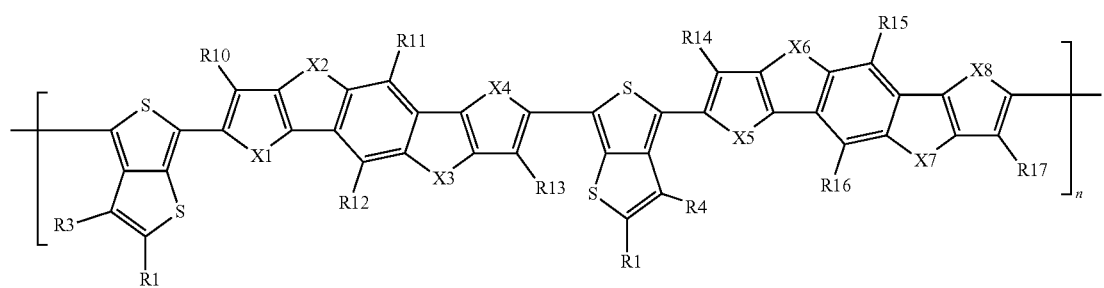
[Chemical Formula 7]
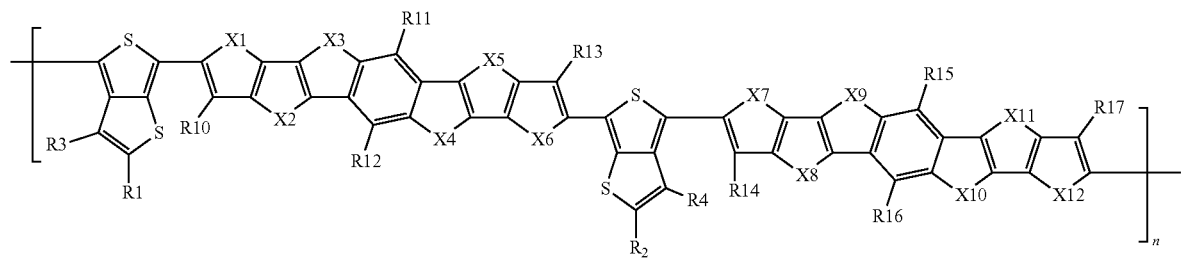

-continued

[Chemical Formula 8]

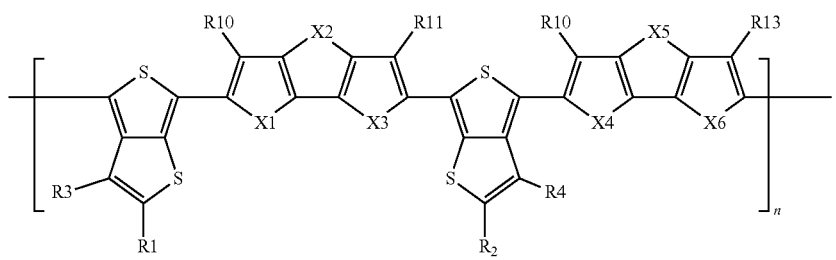

[Chemical Formula 9]

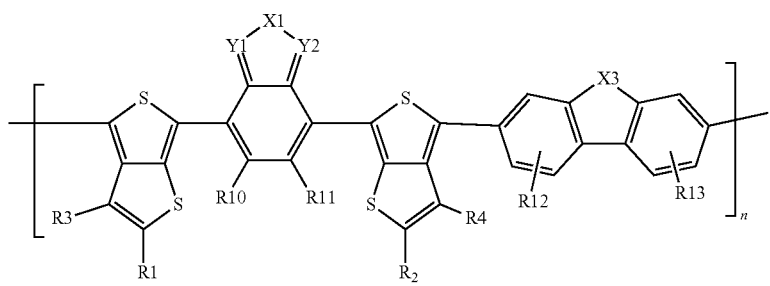

[Chemical Formula 10]

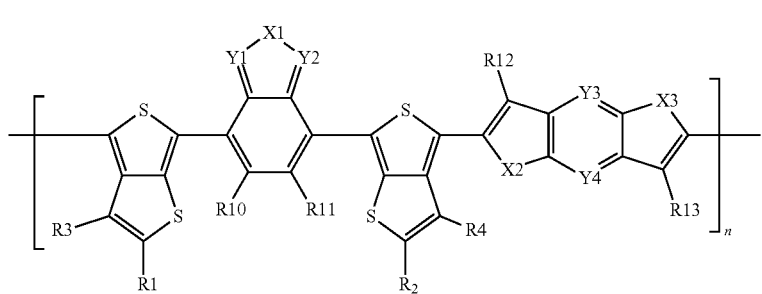

Wherein:

n is an integer of 1 to 10,000;

X1 to X12 are the same as or different from each other, and each is independently CRR', NR, O, SiRR', PR, S, GeRR', Se or Te;

Y1 to Y4 are the same as or different from each other, and each is independently CR", N, SiR", P or GeR";

R, R', R", R1, R2, and R10 to R17 are the same as or different from each other, and each is independently hydrogen, a halogen group, a nitro group, a cyano group, a carboxyl group, a hydroxyl group, a substituted or unsubstituted carbonyl group, a substituted or unsubstituted alkyl group, a substituted or unsubstituted allyl group, a substituted or unsubstituted alkoxy group, a substituted or unsubstituted cycloalkyl group, a substituted or unsubstituted alkenyl group, a substituted or unsubstituted ester group, a substituted or unsubstituted amide group, a substituted or unsubstituted ether group, a substituted or unsubstituted sulfonyl group, a substituted or unsubstituted sulfoxy group, a substituted or unsubstituted arylalkyl group, a substituted or unsubstituted aryl group, or a substituted or unsubstituted heterocyclic group including one or more of N, O, S and Se atoms; and R3 and R4 are the same as or different from each other, and each is independently hydrogen, or an electron withdrawing group.

5. The copolymer of claim 1, wherein the unit of Chemical Formula 1 is a unit of any one of the following Chemical Formula 1-1-1 to Chemical Formula 1-1-17:

[Chemical Formula 1-1-1]
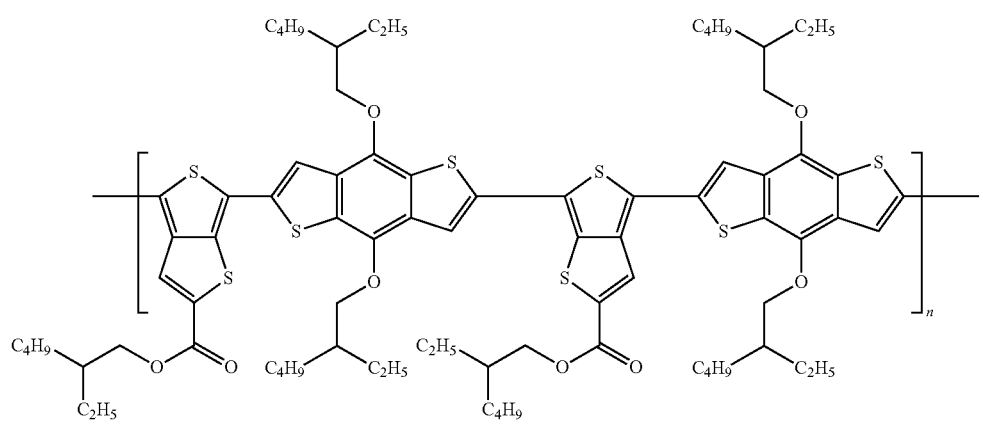
[Chemical Formula 1-1-2]
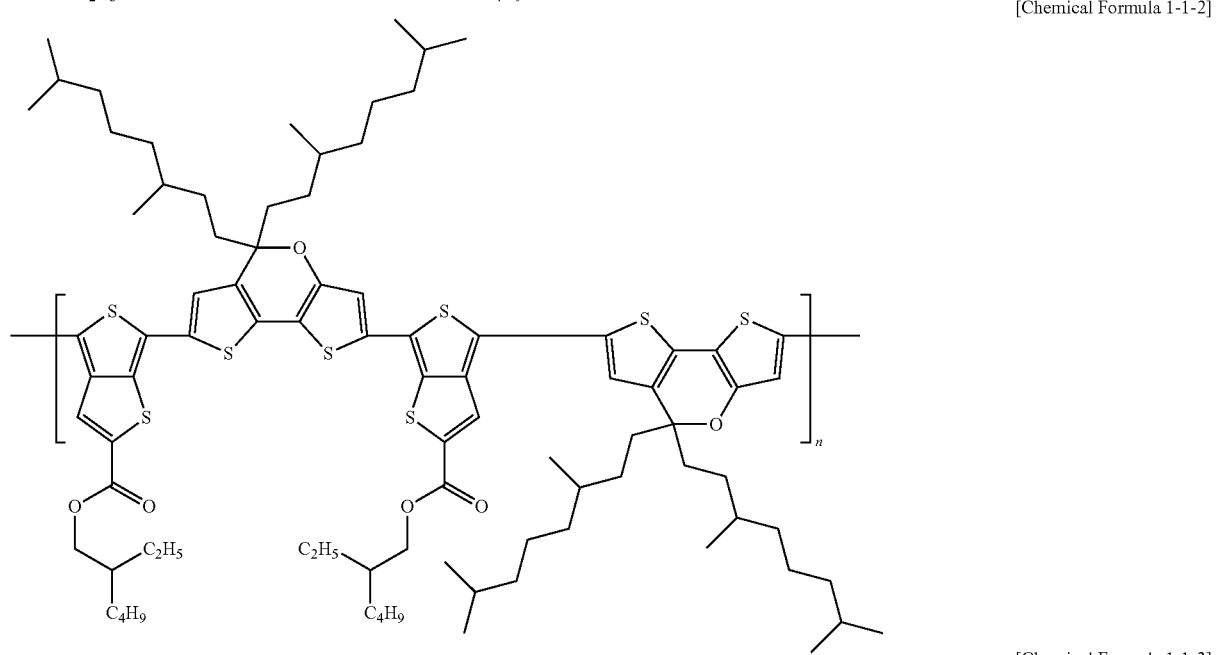
[Chemical Formula 1-1-3]
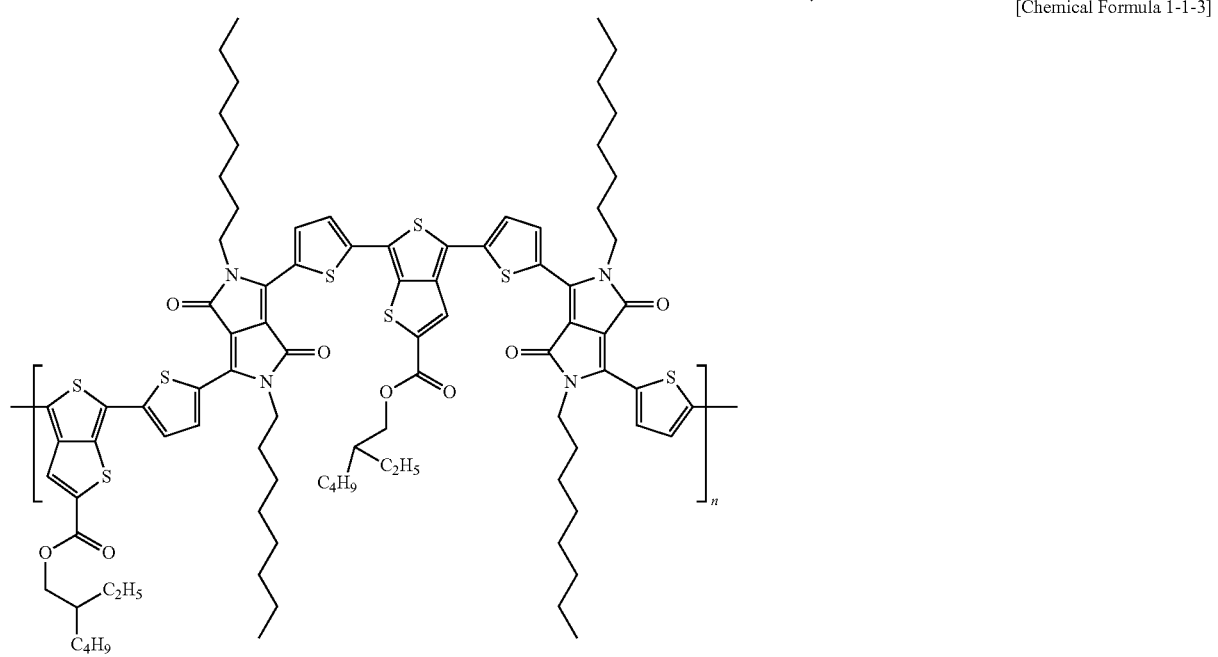

[Chemical Formula 1-1-4]
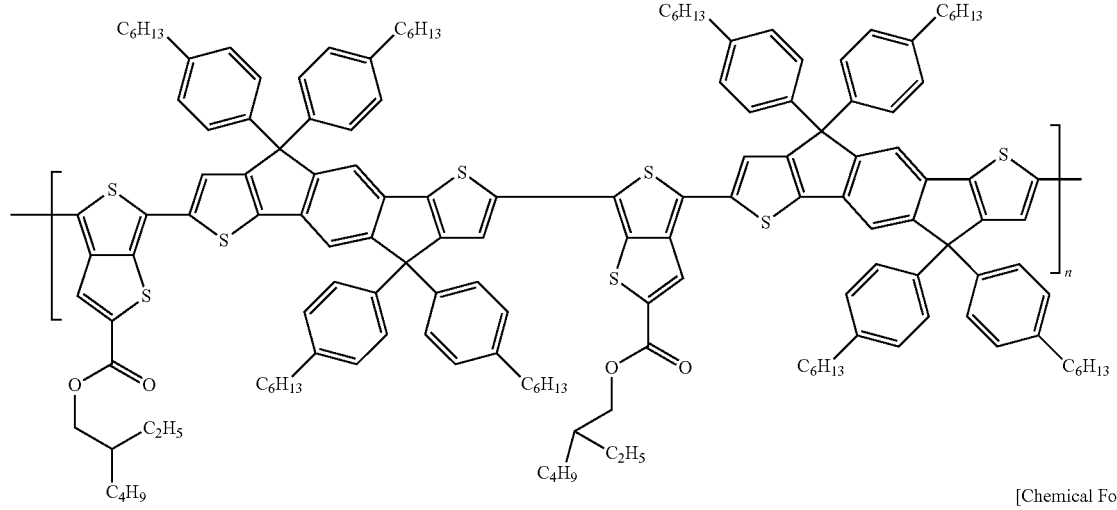
[Chemical Formula 1-1-5]
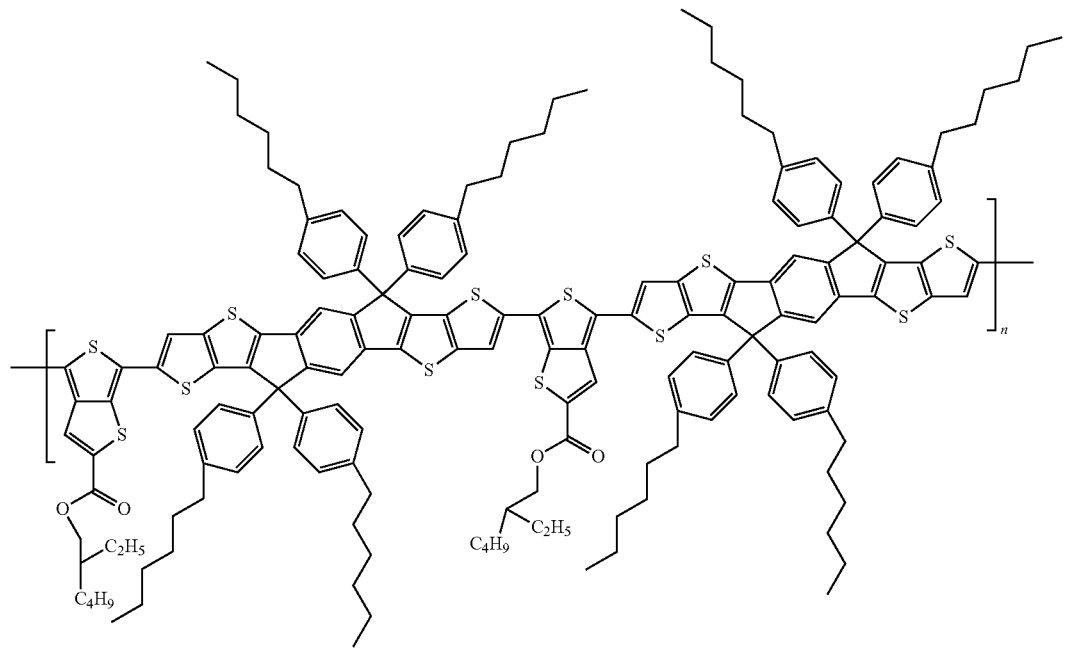
[Chemical Formula 1-1-6]
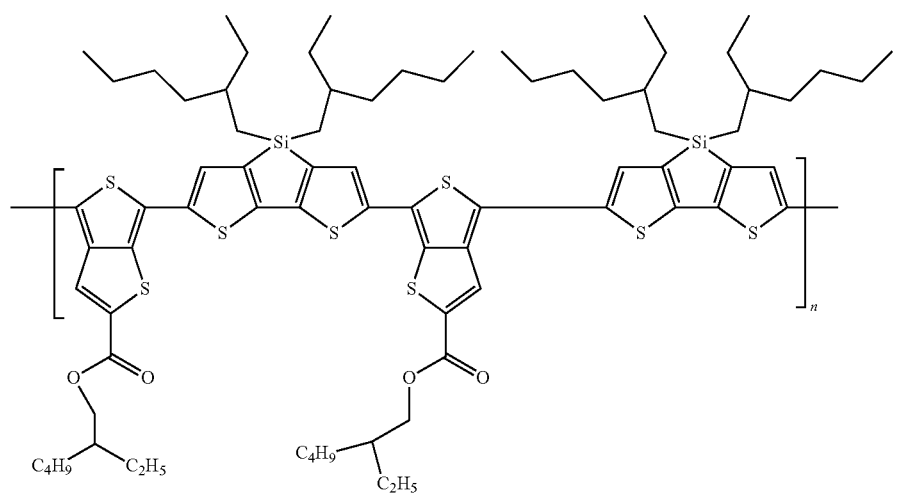

[Chemical Formula 1-1-7]
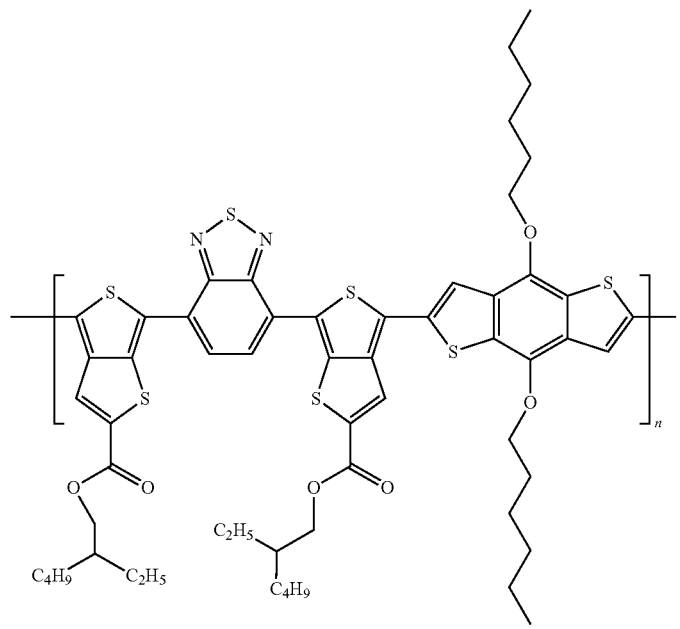
[Chemical Formula 1-1-8]
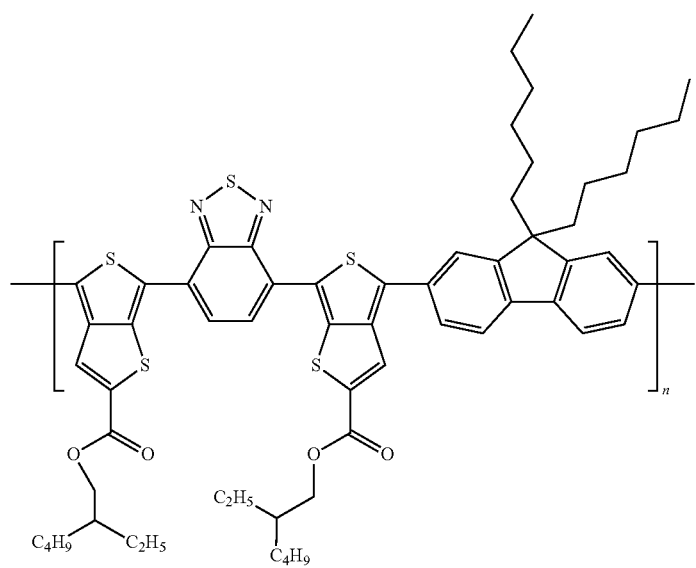

[Chemical Formula 1-1-9]
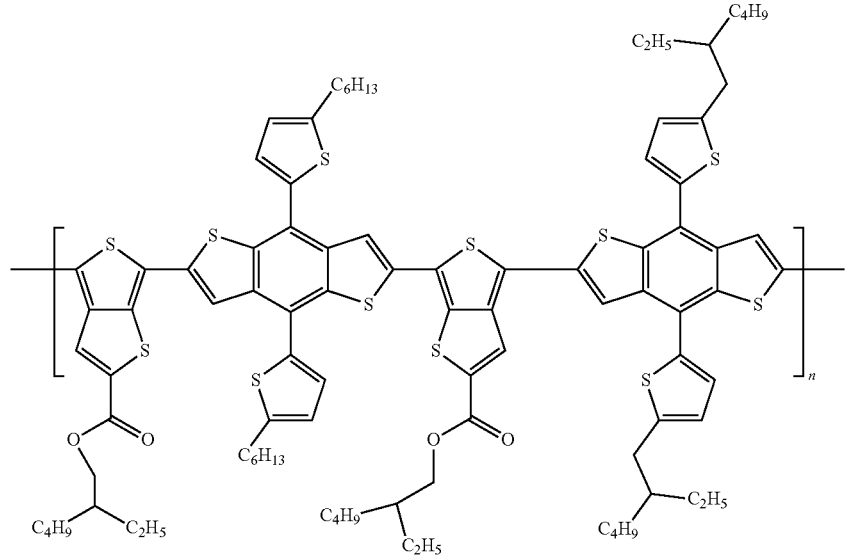
[Chemical Formula 1-1-10]
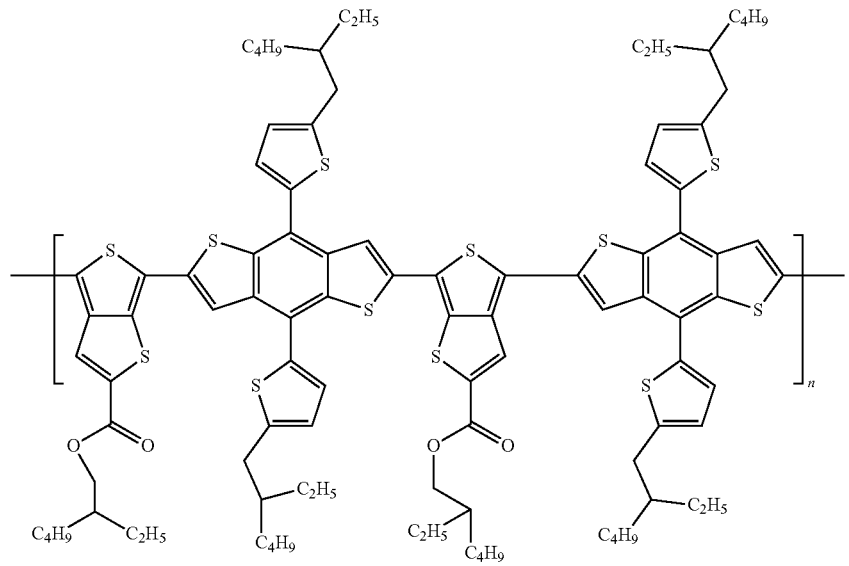
[Chemical Formula 1-1-11]
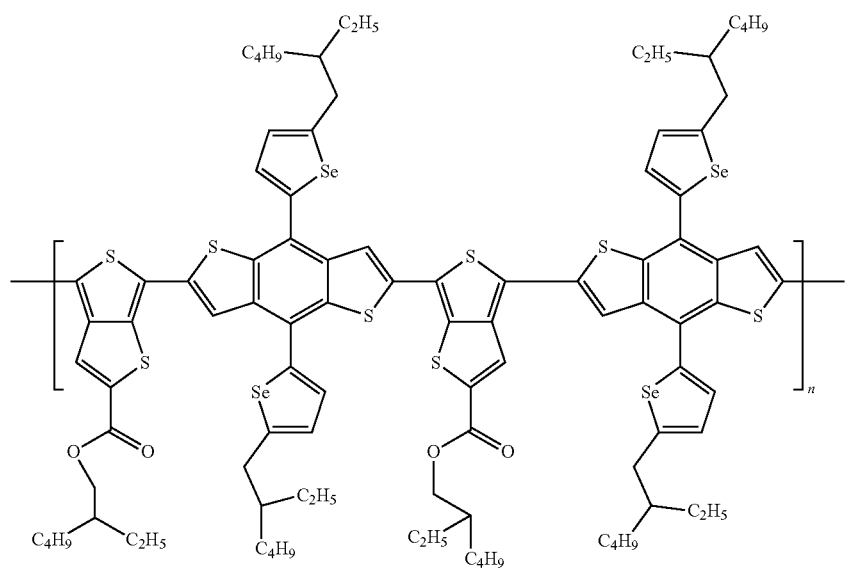

[Chemical Formula 1-1-12]
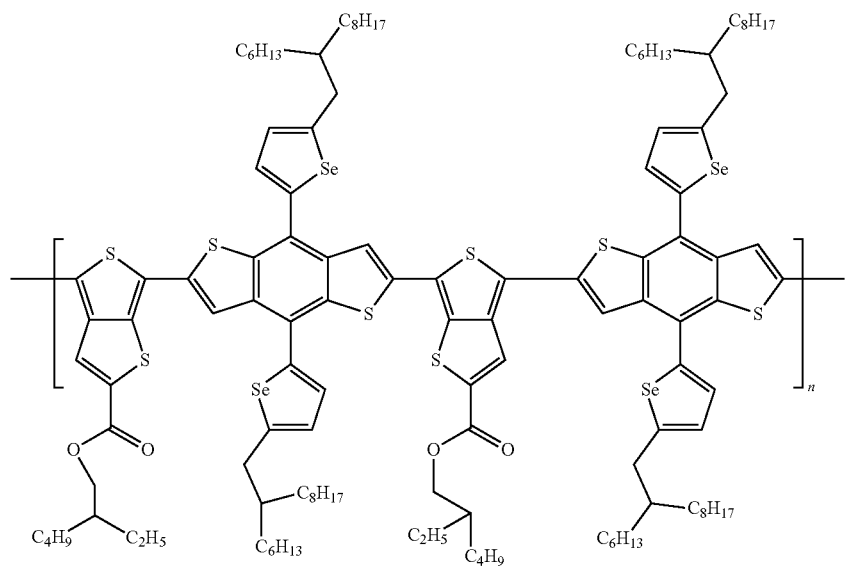
[Chemical Formula 1-1-13]
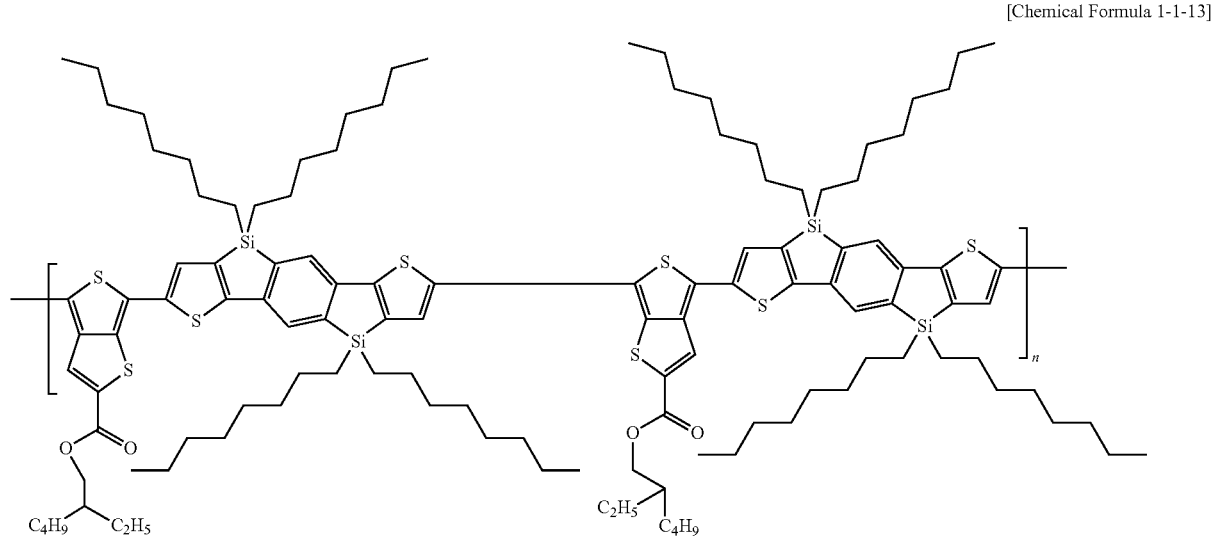
[Chemical Formula 1-1-14]
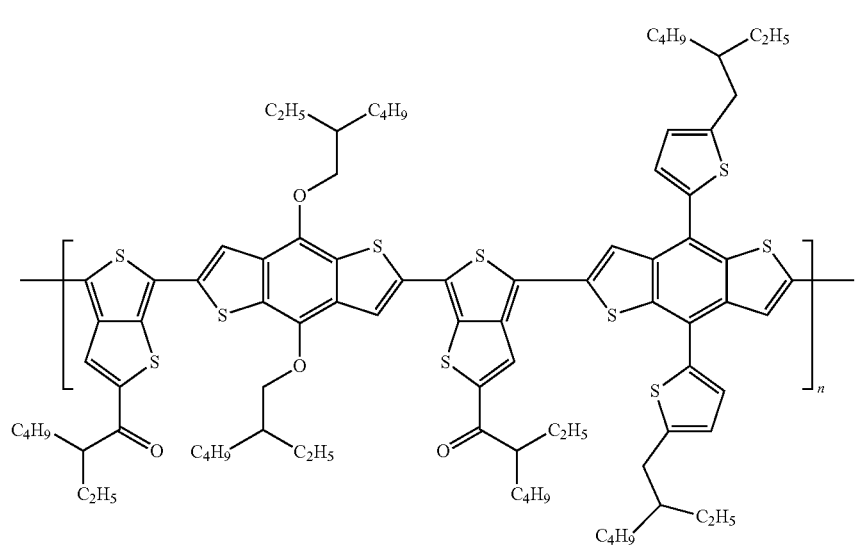

[Chemical Formula 1-1-15]
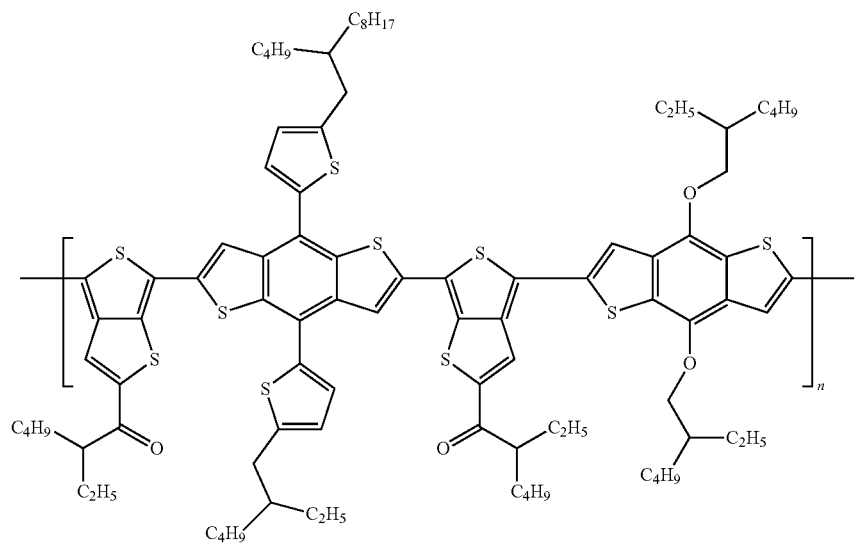
[Chemical Formula 1-1-16]
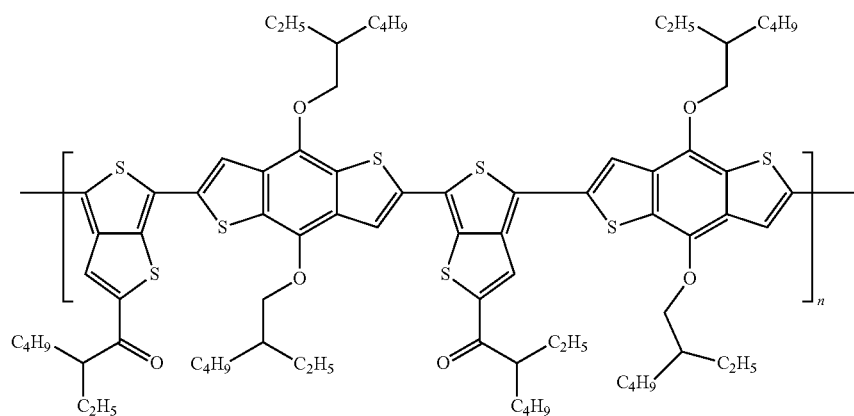
[Chemical Formula 1-1-17]
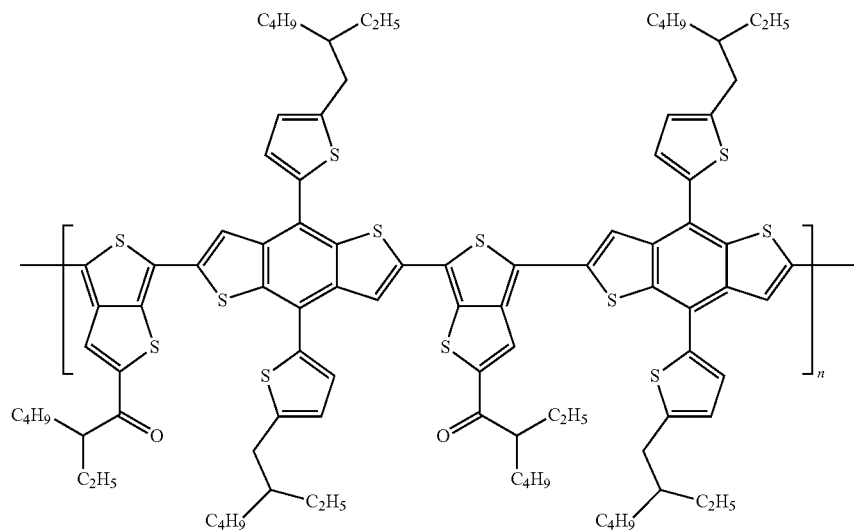
wherein, n is an integer of 1 to 10,000.
6. The copolymer of claim 1, wherein the copolymer has a number average molecular weight of 500 g/mol to 1,000,000 g/mol.
7. The copolymer of claim 1, wherein the copolymer has a molecular weight distribution of 1 to 100.
8. The copolymer of claim 1, wherein the unit of Chemical Formula 1 is a unit of Chemical Formula 1-1:

[Chemical Formula 1-1]

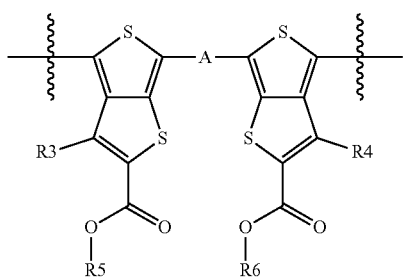

wherein A, R3 and R4 are the same as those defined in Chemical Formula 1, and wherein R5 and R6 are the same as or different from each other, and each is independently hydrogen, a halogen group, a nitro group, a cyano group, a carboxyl group, a hydroxyl group, a substituted or unsubstituted carbonyl group, a substituted or unsubstituted alkyl group, a substituted or unsubstituted allyl group, a substituted or unsubstituted alkoxy group, a substituted or unsubstituted cycloalkyl group, a substituted or unsubstituted alkenyl group, a substituted or unsubstituted ester group, a substituted or unsubstituted amide group, a substituted or unsubstituted ether group, a substituted or unsubstituted sulfonyl group, a substituted or unsubstituted sulfoxy group, a substituted or unsubstituted arylalkyl group, a substituted or unsubstituted aryl group, or a substituted or unsubstituted heterocyclic group including one or more of N, O, S and Se atoms.

9. The copolymer of claim 1, wherein the unit of Chemical Formula 1 is a unit of Chemical Formula 1-2:

[Chemical Formula 1-2]

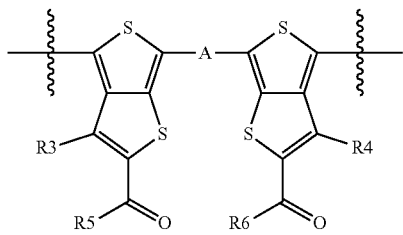

wherein A, R3 and R4 are the same as those defined in Chemical Formula 1, and wherein R5 and R6 are the same as or different from each other, and each is independently hydrogen, a halogen group, a nitro group, a cyano group, a carboxyl group, a hydroxyl group, a substituted or unsubstituted carbonyl group, a substituted or unsubstituted alkyl group, a substituted or unsubstituted allyl group, a substituted or unsubstituted alkoxy group, a substituted or unsubstituted cycloalkyl group, a substituted or unsubstituted alkenyl group, a substituted or unsubstituted ester group, a substituted or unsubstituted amide group, a substituted or unsubstituted ether group, a substituted or unsubstituted sulfonyl group, a substituted or unsubstituted sulfoxy group, a substituted or unsubstituted arylalkyl group, a substituted or unsubstituted aryl group, or a substituted or unsubstituted heterocyclic group including one or more of N, O, S and Se atoms.

10. An organic solar cell comprising:
a first electrode;
a second electrode provided opposite to the first electrode; and
one or more organic material layers provided between the first electrode and the second electrode, and including a photoactive layer,
wherein the one or more layers of the organic material layers include the copolymer of claim 1.

11. The organic solar cell of claim 10, wherein the organic material layer includes a hole transfer layer, a hole injection layer, or a layer carrying out hole transfer and hole injection at the same time, and the hole transfer layer, the hole injection layer, or the layer carrying out hole transfer and hole injection at the same time includes the copolymer.

12. The organic solar cell of claim 10, wherein the organic material layer includes an electron injection layer, an electron transfer layer, or a layer carrying out electron injection and electron transfer at the same time, and the electron injection layer, the electron transfer layer, or the layer carrying out electron injection and electron transfer at the same time includes the copolymer.

13. The organic solar cell of claim 10, wherein the photoactive layer includes one, two or more selected from the group consisting of an electron donor and an electron acceptor, and the electron donor includes the copolymer.

14. The organic solar cell of claim 13, wherein the electron acceptor is selected from the group consisting of fullerene, fullerene derivatives, carbon nanotubes, carbon nanotube derivatives, bathocuproine, semiconductor elements, semiconductor compounds, and combinations thereof.

15. The organic solar cell of claim 13, wherein the electron donor and the electron acceptor form a bulk heterojunction (BHJ).

16. The organic solar cell of claim 10, wherein the photoactive layer has a bilayer structure including an n-type organic material layer and a p-type organic material layer, and the p-type organic material layer includes the copolymer.

* * * * *

UNITED STATES PATENT AND TRADEMARK OFFICE
CERTIFICATE OF CORRECTION

PATENT NO. : 10,355,214 B2
APPLICATION NO. : 15/125961
DATED : July 16, 2019
INVENTOR(S) : Cho et al.

It is certified that error appears in the above-identified patent and that said Letters Patent is hereby corrected as shown below:

In the Claims

Column 100, Claim 4, Formula 6: Please delete Formula 6 and replace with:

[Chemical Formula 6]

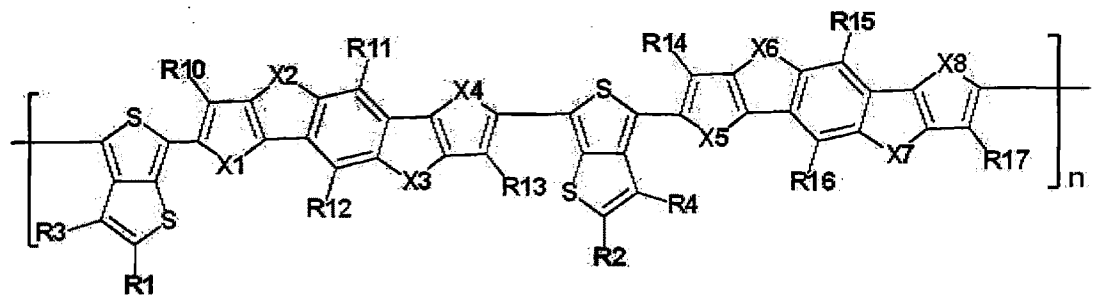

Column 101, Claim 4, Formula 8: Please delete Formula 8 and replace with:

[Chemical Formula 8]

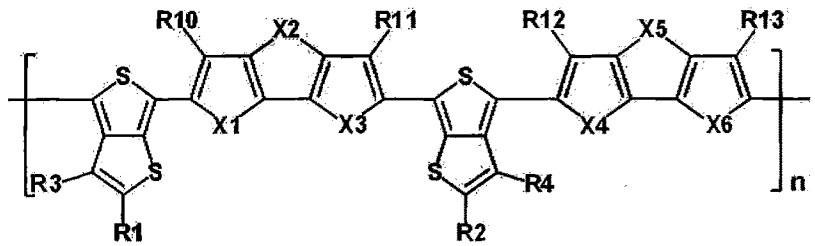

Signed and Sealed this
Tenth Day of December, 2019

Andrei Iancu
*Director of the United States Patent and Trademark Office*

CERTIFICATE OF CORRECTION (continued)
U.S. Pat. No. 10,355,214 B2

Column 113, Claim 5, Formula 1-1-15: Please delete Formula 1-1-15 and replace with:

[Chemical Formula 1-1-15]